United States Patent
Niori

(10) Patent No.: US 10,158,088 B2
(45) Date of Patent: Dec. 18, 2018

(54) ORGANIC SEMICONDUCTOR LIQUID COMPOSITION, ORGANIC SEMICONDUCTOR ELEMENT, AND METHOD FOR PREPARING ORGANIC SEMICONDUCTOR ELEMENT

(71) Applicant: FUJIFILM CORPORATION, Minato-ku, Tokyo (JP)

(72) Inventor: Teruki Niori, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 15/646,103

(22) Filed: Jul. 11, 2017

(65) Prior Publication Data
US 2017/0309836 A1 Oct. 26, 2017

Related U.S. Application Data

(63) Continuation of application No. PCT/JP2016/057098, filed on Mar. 8, 2016.

(30) Foreign Application Priority Data

Mar. 11, 2015 (JP) .................. 2015-048518

(51) Int. Cl.
*H01L 51/00* (2006.01)
*C07F 7/08* (2006.01)
(Continued)

(52) U.S. Cl.
CPC ............ *H01L 51/0076* (2013.01); *C07F 7/08* (2013.01); *H01L 29/786* (2013.01);
(Continued)

(58) Field of Classification Search
None
See application file for complete search history.

(56) References Cited

FOREIGN PATENT DOCUMENTS

| JP | 2004-031458 A | 1/2004 |
| JP | 2009-267372 A | 11/2009 |

(Continued)

OTHER PUBLICATIONS

Extended European Search Report dated Dec. 22, 2017, issued in corresponding EP Patent Application No. 16761742.2.
(Continued)

*Primary Examiner* — Reema Patel
(74) *Attorney, Agent, or Firm* — SOLARIS Intellectual Property Group, PLLC

(57) ABSTRACT

An object of the present invention is to provide an organic semiconductor liquid composition making it possible to obtain an organic semiconductor film having high mobility, an organic semiconductor element prepared using the organic semiconductor liquid composition, and a method for preparing the organic semiconductor element.
The organic semiconductor liquid composition of the present invention contains an organic semiconductor, a liquid crystal compound, and an organic insulating polymer. It is preferable that the organic insulating polymer includes a resin having a constitutional unit represented by Formula 1a and/or a constitutional unit represented by Formula 1b. In the formulae, R's each independently represents a linear or branched alkyl group having 1 to 20 carbon atoms.

(1a)

(Continued)

-continued

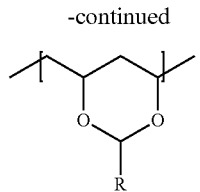

(1b)

17 Claims, 2 Drawing Sheets

(51) Int. Cl.
    *H01L 29/786*     (2006.01)
    *H01L 51/05*     (2006.01)

(52) U.S. Cl.
    CPC ........ *H01L 51/004* (2013.01); *H01L 51/0074* (2013.01); *H01L 51/0094* (2013.01); *H01L 51/0003* (2013.01); *H01L 51/0026* (2013.01); *H01L 51/0055* (2013.01); *H01L 51/0545* (2013.01); *H01L 51/0558* (2013.01)

(56) References Cited

FOREIGN PATENT DOCUMENTS

JP     2009-289783 A     12/2009
JP     2004-006754 A     1/2014

OTHER PUBLICATIONS

Communication pursuant to Article 94(c) EPC dated Jul. 11, 2018, issued in corresponding EP Patent Application No. 16761742.2.
Lee Jiyoul et al: "Enhanced electrical stability of organic thin-film transistors with polymer semiconductor-insulator blended active layers", Appl. Phys. Lett.i 2012, 100, 83302-1-83302-5, (XP012157167, DOI: 10.1063/1.3688177).
Jeremy Smith et al: "Solution-processed organic transistors based on semiconducting blends", J. Mater. Chem., 2010, 20, 2562, (XP055029242, DOI: 10.1039/b921674j).

ORGANIC SEMICONDUCTOR LIQUID COMPOSITION, ORGANIC SEMICONDUCTOR ELEMENT, AND METHOD FOR PREPARING ORGANIC SEMICONDUCTOR ELEMENT

CROSS-REFERENCE TO RELATED APPLICATIONS

This application is a Continuation of International Application No. PCT/JP2016/057098 filed on Mar. 8, 2016, which claims priority to Japanese Patent Application No. 2015-048518 filed on Mar. 11, 2015. The entire contents of these applications are incorporated herein by reference.

BACKGROUND OF THE INVENTION

1. Field of the Invention

The present invention relates to an organic semiconductor liquid composition, an organic semiconductor element, and a method for preparing the organic semiconductor element.

2. Description of the Related Art

An organic transistor having an organic semiconductor film (organic semiconductor layer) is used in a field effect transistor (FET) used in a liquid crystal display or an organic electroluminescence (EL) display, a radio frequency identifier (RFID, RF tag), and the like, because the use of the organic transistor makes it possible to achieve weight lightening, cost reduction, and flexibilization.

As the method for preparing an organic semiconductor film, various methods are suggested.

For example, as the composition forming an organic semiconductor film, the compositions described in JP2009-267372A and JP2004-6754A are known.

JP2009-267372A describes an organic semiconductor liquid composition containing a low-molecular weight compound and a polymer compound having carrier transport properties, in which a difference in a solubility parameter between the polymer compound and the low-molecular weight compound is equal to or greater than 0.6 and equal to or less than 1.5. JP2004-6754A describes an organic semiconductor material containing a polymer compound and a low-molecular weight compound, in which the polymer compound has a skeleton structure formed of π electron rings selected from the group consisting of L 6 π electron-based rings, M 8 π electron-based rings, N 10 π electron-based rings, O 12 π electron-based rings, P 14 π electron-based rings, Q 16 π electron-based rings, R 18 π electron-based rings, S 20 π electron-based rings, T 22 π electron-based rings, U 24 π electron-based rings, and V 26 π electron-based rings (here, L, M, N, O, P, Q, R, S, T, U, and V each represent an integer of 0 to 6, and L+M+N+O+P+Q+R+S+T+U+V=1 to 6) on a portion of a side chain, and the low-molecular weight compound has a skeleton structure formed of π electron-based rings selected from the aforementioned group of π electron rings and has a terminal group expressing liquid crystallinity on at least one of both terminals.

As an organic semiconductor film and a method for preparing the same, the film described in JP2009-289783A or the method described in JP2004-31458A is known.

JP2009-289783A describes an organic semiconductor laminated film having an organic semiconductor layer, which contains at least carbon nanotubes and a liquid crystal organic semiconductor, and an alignment layer contacting the organic semiconductor layer.

JP2004-31458A describes a method for preparing a semiconductor device, including a step of coating a substrate with a liquid material obtained by dissolving an organic semiconductor material in a solvent and a step of removing the solvent, in which a liquid crystal material is used as the solvent.

SUMMARY OF THE INVENTION

An object of the present invention is to provide an organic semiconductor liquid composition making it possible to obtain an organic semiconductor film having high mobility, an organic semiconductor element prepared using the organic semiconductor liquid composition, and a method for preparing the organic semiconductor element.

The object of the present invention was achieved by means described below in <1>, <8>, or <10>. Preferred embodiments are also described below in <2> to <7>, <9>, <11>, and <12>.

<1> An organic semiconductor liquid composition comprising an organic semiconductor, a liquid crystal compound, and an organic insulating polymer.

<2> The organic semiconductor liquid composition described in <1>, in which the organic insulating polymer includes a resin having a constitutional unit represented by the following Formula 1a and/or a constitutional unit represented by the following Formula 1b.

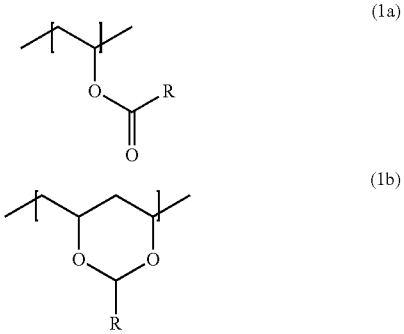

In the formulae, R's each independently represent a linear or branched alkyl group having 1 to 20 carbon atoms.

<3> The organic semiconductor liquid composition described in <1> or <2>, in which the organic insulating polymer is polyvinyl carboxylate or polyvinyl acetal.

<4> The organic semiconductor liquid composition described in <3>, in which the organic insulating polymer is polyvinyl carboxylate or polyvinyl butyral.

<5> The organic semiconductor liquid composition described in any one of <1> to <4>, in which the liquid crystal compound includes a liquid crystal compound having a polymerizable group.

<6> The organic semiconductor liquid composition described in <5>, in which the liquid crystal compound includes a liquid crystal compound having an ethylenically unsaturated group.

<7> The organic semiconductor liquid composition described in <5> or <6>, further comprising a polymerization initiator.

<8> A method for preparing an organic semiconductor element, comprising a film forming step of forming a film through coating by using the organic semiconductor liquid composition described in any one of <1> to <7>, a melting step of melting the film by heating, and a phase separation step of causing phase separation by cooling the melted film so as to form a laminated structure in which an organic insulating polymer layer, an organic semiconductor layer, and a liquid crystal compound layer are laminated in this order.

<9> The method for preparing an organic semiconductor element described in <8>, further comprising a polymerization step of polymerizing the liquid crystal compound having a polymerizable group after the phase separation step, in which the liquid crystal compound includes a liquid crystal compound having a polymerizable group.

<10> An organic semiconductor element prepared by the method described in <8> or <9>.

<11> The organic semiconductor element described in <10> that is an organic thin film transistor.

<12> The organic semiconductor element described in <11> that is a bottom contact-type organic thin film transistor.

According to the present invention, it is possible to provide an organic semiconductor liquid composition making it possible to obtain an organic semiconductor film having high mobility, an organic semiconductor element prepared using the organic semiconductor liquid composition, and a method for preparing the organic semiconductor element.

DESCRIPTION OF THE PREFERRED EMBODIMENTS

Figure 1:
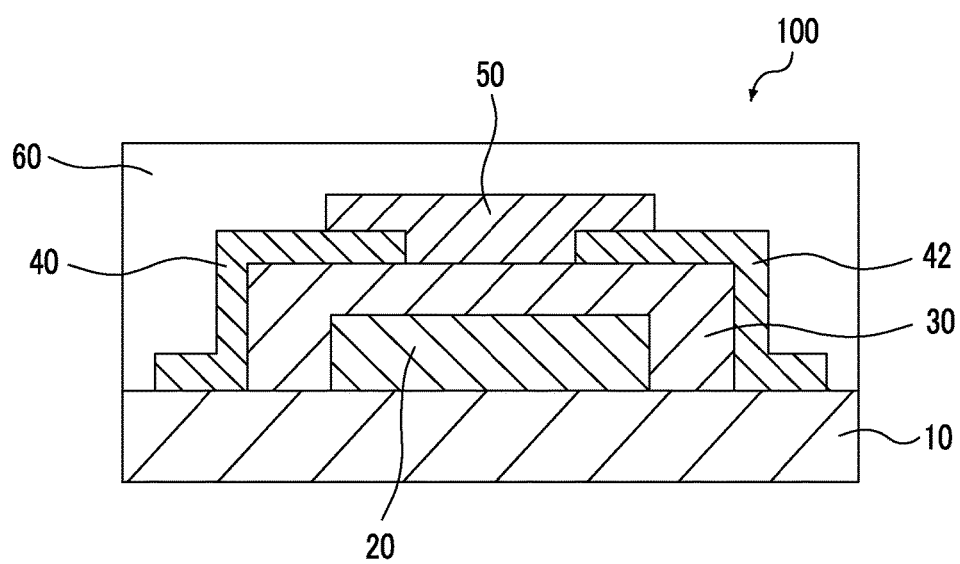
FIG. 1 is a schematic cross-sectional view of an aspect of an organic semiconductor element of the present invention.

Hereinafter, the contents of the present invention will be specifically described. The constituents in the following description will be explained based on typical embodiments of the present invention, but the present invention is not limited to the embodiments. In the specification of the present application, "to" is used to mean that the numerical values listed before and after "to" are a lower limit and an upper limit respectively. Furthermore, in the present invention, an organic EL element refers to an organic electroluminescence element.

In the present specification, in a case where there is no description regarding whether a group (atomic group) is substituted or unsubstituted, the group includes both of a group having a substituent and a group not having a substituent. For example, an "alkyl group" includes not only an alkyl group not having a substituent (unsubstituted alkyl group) but also an alkyl group having a substituent (substituted alkyl group).

In the present specification, in some cases, a chemical structural formula is described as a simplified structural formula in which a hydrogen atom is omitted.

In the present invention, the description of "mobility" refers to carrier mobility and means either or both of electron mobility and hole mobility.

In the present invention, "% by mass" and "% by weight" have the same definition, and "part by mass" and "part by weight" have the same definition.

In the present invention, a combination of two or more preferred aspects is a more preferred aspect.

(Organic Semiconductor Liquid Composition)

An organic semiconductor liquid composition (hereinafter, simply referred to as "composition" as well) of the present invention contains an organic semiconductor, a liquid crystal compound, and an organic insulating polymer.

In the present invention, the organic insulating polymer is an organic polymer which has an electric resistivity of equal to or higher than $1 \times 10^7$ Ω·m at 20° C.

As a result of repeating thorough examination, the inventors of the present invention found that in a case where the composition contains an organic semiconductor, a liquid crystal compound, and an organic insulating polymer, it is possible to obtain an organic semiconductor film having high mobility. Based on what they had found, the inventors accomplished the present invention.

The detail of the mechanism that brings about the aforementioned effect is unclear. However, presumably, because the three components of the organic semiconductor, the liquid crystal compound, and the organic insulating polymer may act cooperatively with each other, and the formation of a laminated structure in which an organic insulating polymer layer, an organic semiconductor layer, and a liquid crystal compound layer are laminated in this order may exert an effect, the organic semiconductor film having high mobility can be obtained.

<Organic Semiconductor>

The organic semiconductor liquid composition of the present invention contains an organic semiconductor.

The organic semiconductor may be a low-molecular weight compound or a polymer, but is preferably a low-molecular weight compound.

The low-molecular weight compound used as the organic semiconductor is preferably a compound having a molecular weight of less than 1,000.

Furthermore, the low-molecular weight compound used as the organic semiconductor is preferably a condensed polycyclic aromatic compound. The condensed polycyclic aromatic compound has a strong effect of improving carrier mobility and durability and also has a better effect of reducing threshold voltage.

Examples of the condensed polycyclic aromatic compound include acene such as naphthacene, pentacene (2,3,6,7-dibenzoanthracene), hexacene, heptacene, dibenzopentacene, or tetrabenzopentacene, anthradithiophene, pyrene, benzopyrene, dibenzopyrene, chrysene, perylene, coronene, terylene, ovalene, quoterylene, circumanthracene, derivatives obtained by substituting some of the carbon atoms of the above compounds with an atom of N, S, O, and the like, derivatives obtained by substituting at least one hydrogen atom bonded to the carbon atoms with a functional group such as a carbonyl group (a dioxaanthanthrene-based compound containing peri-xanthenoxanthene and a derivative thereof, triphenodioxanzine, triphenodithiazine, hexacene-6,15-quinone, and the like), derivatives obtained by substituting the hydrogen atom with other functional groups, and the like.

Examples of the organic semiconductor include metal phthalocyanine represented by copper phthalocyanine, tetrathiapentalene and a derivative thereof, ring-fused tetracarboxylic acid diimide like naphthalene carboxylic acid diimide such as naphthalene-1,4,5,8-tetracarboxylic acid diimide, N,N'-bis(4-trifluoromethylbenzyl)naphthalene-1,4,5,8-tetracarboxylic acid diimide, N,N'-bis(1H, 1H-perfluorooctyl), N,N'-bis(1H, 1H-perfluorobutyl), a N,N'-dioctyl-naphthalene-1,4,5,8-tetracarboxylic acid diimide derivative, or naphthalene-2,3,6,7-tetracarboxylic acid diimide and anthracene tetracarboxylic acid diimide such as anthracene-2,3,6,7-tetracarboxylic acid diimide, fullerene such as C60, C70, C76, C78, or C84 and a derivative thereof, carbon nanotubes such as single-wall carbon nanotube (SWNT), a dye such as a merocyanine dye or a hemicyanine dye and a derivative thereof, and the like.

Examples of the organic semiconductor also include polyanthracene, triphenylene, and quinacridone.

Examples of the organic semiconductor also include 4,4'-biphenyldithiol (BPDT), 4,4'-diisocyanobiphenyl, 4,4'-diisocyano-p-terphenyl, 2,5-bis(5'-thioacetyl-2'-thiophenyl)thiophene, 2,5-bis(5'-thioacetoxyl-2'-thiophenyl)thiophene, 4,4'-diisocyanophenyl, benzidine(biphenyl-4,4'-diamine), tetracyanoquinodimethane (TCNQ), tetrathiafulvalene (TTF) and a derivative thereof, a charge transfer complex represented by a tetrathiafulvalene (TTF)-TCNQ complex, a bisethylenetetrathiafluvalene (BEDTTTF)-perchloric acid complex, a BEDTTTF-iodine complex, or a TCNQ-iodine complex, biphenyl-4,4'-dicarboxylic acid, 1,4-di(4-thiophenylacetylenyl)-2-ethylbenzene, 1,4-di(4-isocyanophenylacetylenyl)-2-ethylbenzene, 1,4-di(4-thiophenylethynyl)-2-ethylbenzene, 2,2"-dihydroxy-1,1':4',1"-terphenyl, 4,4'-biphenyldiethanol, 4,4'-biphenyldiole, 4,4'-biphenyldiisocyanate, 1,4-diacetynylbenzene, diethylbiphenyl-4,4'-dicarboxylate, benzo[1,2-c;3,4-c';5,6-c"]tris[1,2]dithiol-1,4,7-trithione, α-sexithiophene, tetrathiatetracene, tetraselenotetracene, tetratellurutetracene, poly(3-alkylthiophene), poly(3-thiophene-β-ethane sulfonic acid), poly(N-alkylpyrrole)poly(3-alkylpyrrole), poly(3,4-dialkylpyrrole), poly(2,2'-thienylpyrrole), and poly(dibenzothiophenesulfide).

As the condensed polycyclic aromatic compound, a compound represented by Formula (1), acene represented by any of Formulae (A1) to (A4), and a compound represented by any of the following Formulae (C) to (H), (J) to (N), and (P) to (T) that will be described later are preferable, and a compound represented by any of the following Formulae (C) to (H), (J) to (N), and (P) to (T) is more preferable because this compound is easily localized together with the insulating polymer.

The condensed polycyclic aromatic compound is preferably a compound represented by Formula (1).

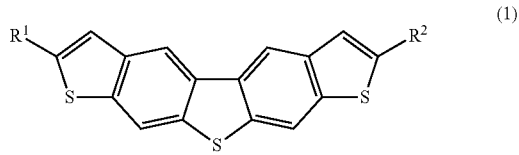

(1)

In Formula (1), $R^1$ and $R^2$ each independently represent an unsubstituted linear alkyl group having an even number of carbon atoms within a range of 8 to 10 carbon atoms, an unsubstituted linear alkyl group having an odd number of carbon atoms within a range of 3 to 15 carbon atoms, a substituted linear alkyl group having 3 to 15 carbon atoms, or a substituted or unsubstituted branched alkyl group having 3 to 18 carbon atoms. The aromatic portion in Formula (1) may be substituted with a halogen atom.

First, a preferred aspect of the structure of the compound represented by Formula (1) will be described.

The unsubstituted linear alkyl group having an even number of carbon atoms within a range of 8 to 10 carbon atoms that is represented by $R^1$ and $R^2$ is preferably a linear alkyl group having 8 or 10 carbon atoms, and particularly preferably a linear alkyl group having 10 carbon atoms. It is preferable that the alkyl group is preferably a long-chain alkyl group having carbon atoms within the above range and particularly preferably a long-chain linear alkyl group, because then the linearity of the molecule is improved, and the carrier mobility can be improved.

The unsubstituted linear alkyl group having an odd number of carbon atoms within a range of 3 to 15 carbon atoms that is represented by $R^1$ and $R^2$ is preferably an unsubstituted linear alkyl group having an odd number of carbon atoms within a range of 5 to 15 carbon atoms, more preferably an unsubstituted linear alkyl group having an odd number of carbon atoms within a range of 7 to 13 carbon atoms, and particularly preferably an unsubstituted linear alkyl group having 9 or 11 carbon atoms.

It is preferable that $R^1$ and $R^2$ preferably each represent a linear alkyl group, because then the linearity of the molecule is improved, and the carrier mobility can be improved. In contrast, from the viewpoint of improving the solubility of the compound in an organic solvent, $R^1$ and $R^2$ may each represent a branched alkyl group.

In a case where $R^1$ and $R^2$ each represent a substituted alkyl group having 3 to 15 carbon atoms or a substituted branched alkyl group having 3 to 18 carbon atoms, the substituent is not particularly limited. Examples of the substituent include a halogen atom, an alkenyl group (including an ethenyl group, a 1-pentenyl group, a 1-heptanyl group, a cycloalkenyl group, a bicycloalkenyl group, and the like), an alkynyl group (including a 1-pentynyl group, a trimethylsilyl ethenyl group, a triethylsilyl ethenyl group, a tri-i-propylsilyl ethenyl group, a 2-p-propylphenyl ethenyl group, and the like), an aryl group (including an aryl group having 6 to 20 carbon atoms such as a phenyl group, a naphthyl group, a p-pentylphenyl group, a 3,4-dipentylphenyl group, a p-heptoxyphenyl group, or a 3,4-diheptoxyphenyl group, and the like), a heterocyclic group (may be referred to as a hetero ring group, including a 2-hexylfuranyl group and the like), a cyano group, a hydroxyl group, a nitro group, an acyl group (including a hexanoyl group, a benzoyl group, and the like), an alkoxy group (including a butoxy group and the like), an aryloxy group (including a phenoxy group and the like), a silyloxy group, a heterocyclic oxy group, an acyloxy group, a carbamoyloxy group, an amino group (including an anilino group), an acylamino group, an aminocarbonyl amino group (including a ureido group), an alkoxy- and aryloxycarbonylamino group, an alkyl- and arylsulfonylamino group, a mercapto group, an alkyl- and arylthio group (including a methylthio group, an octylthio group, and the like), a heterocyclic thio group, a sulfamoyl group, a sulfo group, an alkyl- and arylsulfinyl group, an alkyl- and arylsulfonyl group, an alkyl- and aryloxycarbonyl group, a carbamoyl group, an aryl- and heterocyclic azo group, an imide group, a phosphino group, a phosphinyl group, a phosphinyloxy group, a phosphinylamino group, a phosphono group, a silyl group (such s ditrimethylsiloxymethyl butoxy group), a hydrazino group, a ureido group, a boronic acid group (—B(OH)$_2$), a phosphato group (—OPO(OH)$_2$), a sulfato group (—OSO$_3$H), and other known substituents.

These substituents may further have the above substituents.

Among these, as adoptable substituents, a halogen atom, an aryl group, an alkenyl group, an alkynyl group, a heterocyclic group, an alkoxy group, an alkylthio group, and an aryloxy group are preferable, and a fluorine atom, an aryl group having 6 to 20 carbon atoms, an alkenyl group having 2 to 12 carbon atoms (preferably a 1-alkenyl group), an alkynyl group having 2 to 12 carbon atoms, an alkoxy group having 1 to 11 carbon atoms, a heterocyclic group having 5 to 12 carbon atoms, and an alkylthio group having 1 to 12 carbon atoms are more preferable.

In a case where $R^1$ and $R^2$ each represent an alkyl group substituted with a fluorine atom, some of the hydrogen atoms of the alkyl group may be substituted with a fluorine atom, or all of the hydrogen atoms may be substituted such that a perfluoroalkyl group is formed.

Here, $R^1$ and $R^2$ preferably each independently represent an unsubstituted linear alkyl group or a branched alkyl group.

In a case where $R^1$ and $R^2$ each represent a substituted linear alkyl group having 3 to 15 carbon atoms, the alkyl group is preferably a substituted linear alkyl group having 3 to 13 carbon atoms, more preferably a substituted linear alkyl group having 3 to 11 carbon atoms, even more preferably a substituted linear alkyl group having 5 to 11 carbon atoms, and particularly preferably a substituted linear alkyl group having 7 to 11 carbon atoms.

In a case where $R^1$ and $R^2$ each represent a substituted branched alkyl group having 3 to 18 carbon atoms, the alkyl group is preferably a substituted branched alkyl group having 3 to 15 carbon atoms, more preferably a substituted branched alkyl group having 3 to 13 carbon atoms, even more preferably a substituted branched alkyl group having 3 to 11 carbon atoms, and particularly preferably a substituted branched alkyl group having 7 to 11 carbon atoms.

In a case where $R^1$ and $R^2$ each represent a linear or branched alkyl group having a substituent, —CH$_2$— groups in the linear alkyl group that are not adjacent to each other, —CH$_2$— groups in the branched alkyl group that are not adjacent to each other, a trivalent tertiary carbon atom linking group, or a tetravalent quaternary carbon atom linking group may be each independently substituted with other atomic linking groups. In this case, examples of other atomic linking groups include —O—, —S—, —CO—, —COO—, —OCO—, —COS—, —SCO—, —NRCO—, —CONR— (R represents a hydrogen atom or an alkyl group having 1 to 6 carbon atoms), and the like.

Here, it is preferable that, in $R^1$ and $R^2$, —CH$_2$— groups in the linear alkyl group that are not adjacent to each other, —CH$_2$— groups in the branched alkyl group that are not adjacent to each other, a trivalent tertiary carbon atom linking group, or a tetravalent quaternary carbon atom linking group is not substituted with other atomic linking groups.

The total number of carbon atoms that $R^1$ and $R^2$ each independently have is, including the number of carbon atoms in the substituent, preferably 3 to 30, more preferably 7 to 20, even more preferably 7 to 15, particularly preferably 7 to 11, and most preferably 9 to 11. In a case where the total number of carbon atoms that $R^1$ and $R^2$ each independently have is equal to or greater than the lower limit of the above range, the carrier mobility is improved. In a case where the total number of carbon atoms in $R^1$ and $R^2$ is equal to or less than the upper limit of the above range, the solubility of the compound in an organic solvent is improved.

The aromatic portion in Formula (1) may be substituted with a halogen atom. The halogen atom is preferably a fluorine atom.

The number of halogen atoms substituting the aromatic portion in Formula (1) is preferably 0 to 6, more preferably 0 to 4, even more preferably 0 to 2, and particularly preferably 0.

Specific examples of the compound represented by Formula (1) include the following compounds (1) to (18), but the compound represented by Formula (1) that can be used in the present invention is not limited to the specific examples.

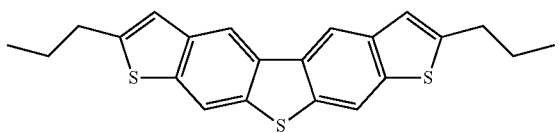

(1)

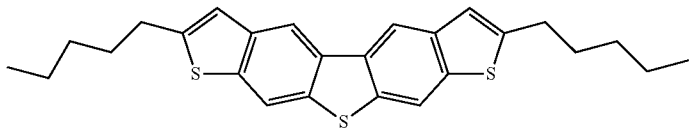

(2)

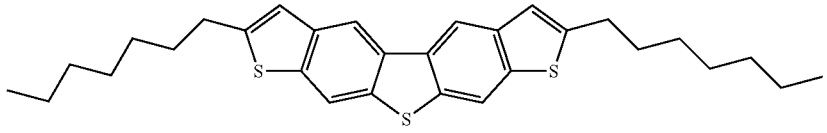

(3)

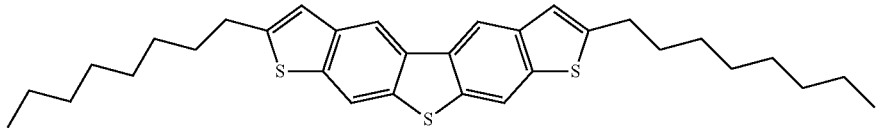

(4)

-continued
(5)
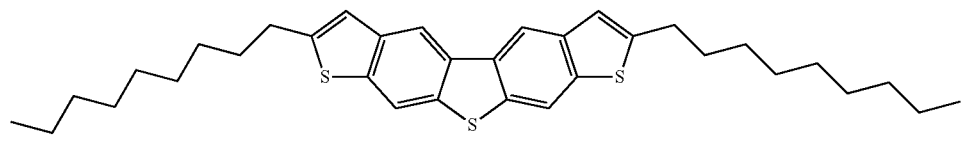
(6)
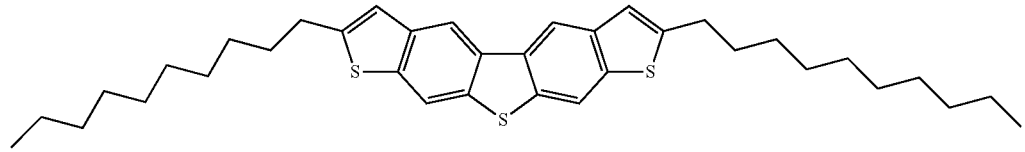
(7)
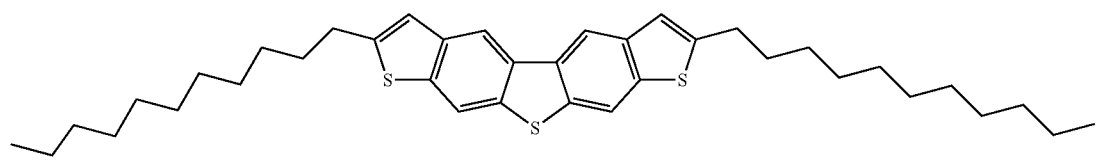
(8)
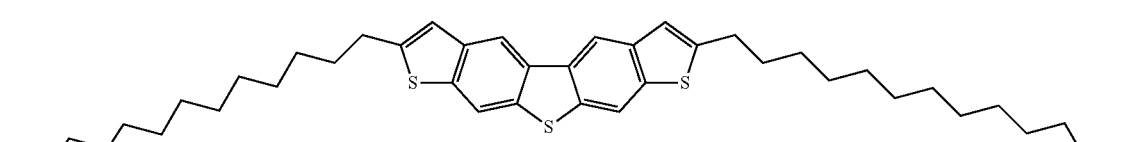
(9)
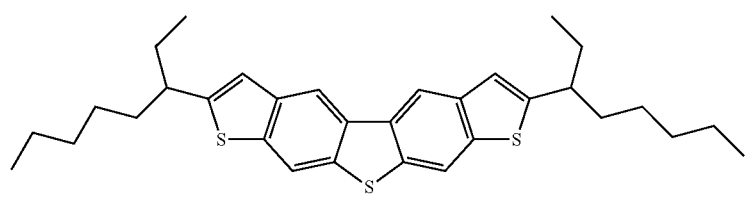
(10)
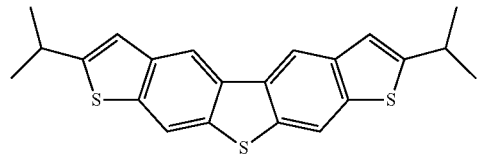
(11)
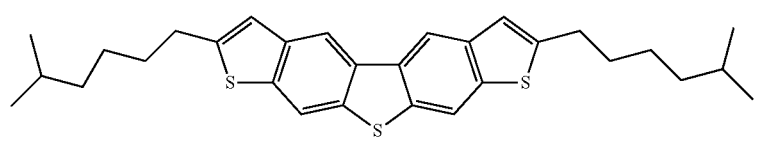
(12)
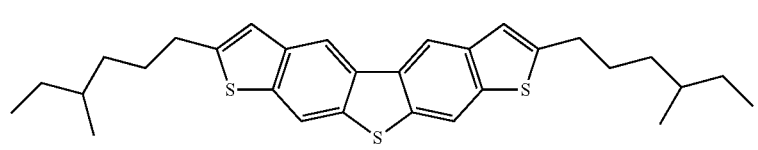
(13)
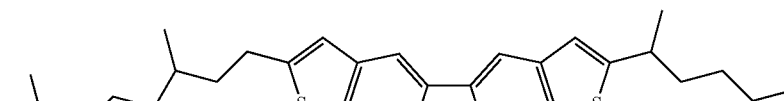
(14)
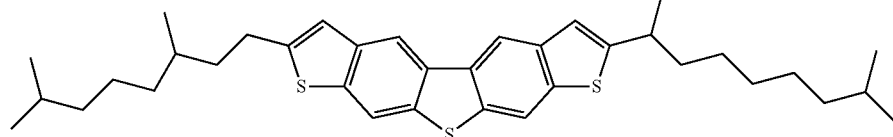
(15)
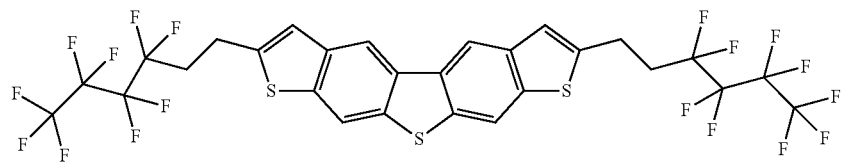

-continued
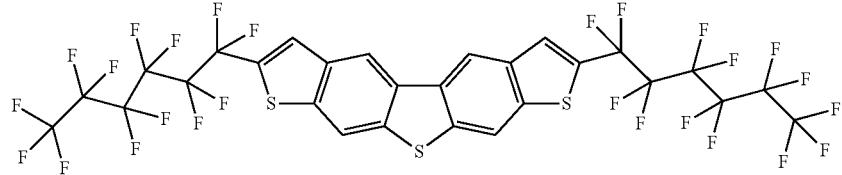
(16)
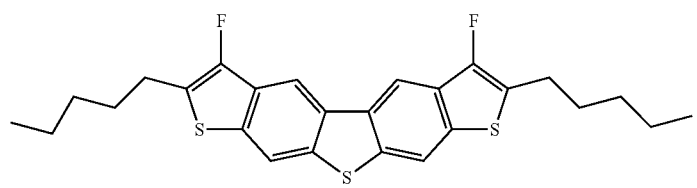
(17)
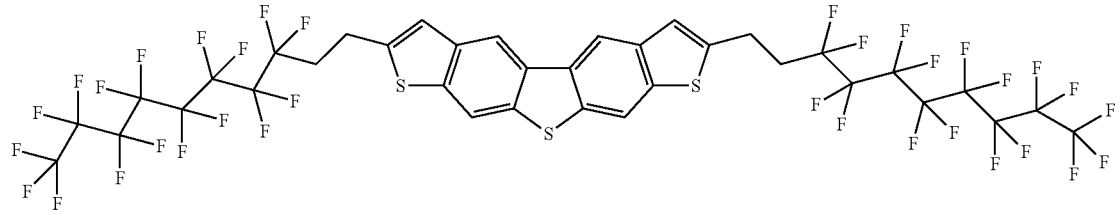
(18)
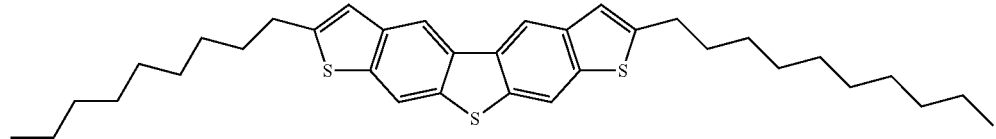
(19)
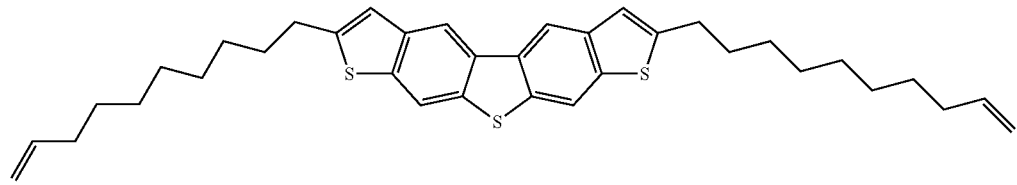
(20)
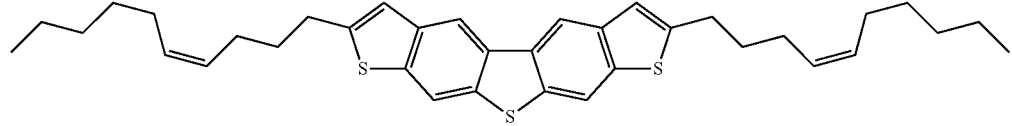
(21)
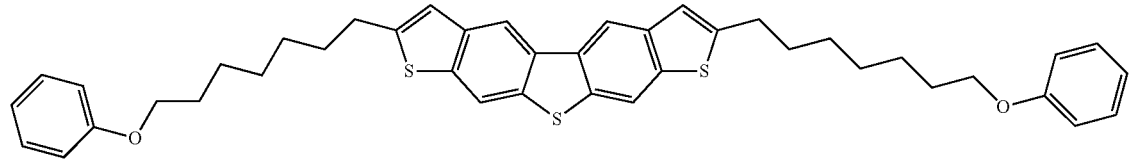
(22)

Examples of the condensed polycyclic aromatic compound preferably include an acene compound.

As the acene compound, a compound represented by the following Formula (A1) or (A2) is preferable.

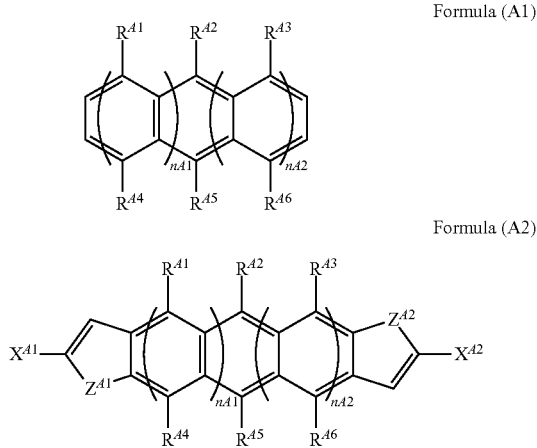

In the formulae, $R^{41}$ to $R^{46}$, $X^{41}$, and $X^{42}$ each independently represent a hydrogen atom or a substituent, $Z^{41}$ and $Z^{42}$ each independently represent S, O, Se, or Te, and nA1 and nA2 each independently represent an integer of 0 to 3. Here, nA1 and nA2 do not simultaneously represent 0.

The substituent represented by each of $R^{41}$ to $R^{46}$, $X^{41}$, and $X^{42}$ is not particularly limited, and examples thereof include an alkyl group (for example, methyl, ethyl, propyl, isopropyl, tert-butyl, pentyl, tert-pentyl, hexyl, octyl, tert-octyl, dodecyl, tridecyl, tetradecyl, or pentadecyl), a cycloalkyl group (for example, cyclopentyl or cyclohexyl), an alkenyl group (for example, vinyl, allyl, 1-propenyl, 2-butenyl, 1,3-butadienyl, 2-pentenyl, or isopropenyl), an alkynyl group (for example, ethynyl or propargyl), an aromatic hydrocarbon group (referred to as an aromatic carbon ring group or an aryl group as well, for example, phenyl, p-chlorophenyl, mesityl, tolyl, xylyl, naphthyl, anthryl, azulenyl, acenaphthenyl, fluorenyl, phenanthryl, indenyl, pyrenyl, or biphenylyl), an aromatic heterocyclic group (referred to as a heteroaryl group as well, for example, a pyridyl group, a pyrimidinyl group, a furyl group, a pyrrolyl group, an imidazolyl group, an benzimidazolyl group, a pyrazolyl group, a pyrazinyl group, a triazolyl group (for example, a 1,2,4-triazol-1-yl group or a 1,2,3-triazol-1-yl group), an oxazolyl group, a benzoxazolyl group, a thiazolyl group, an isoxazolyl group, an isothiazolyl group, a furazanyl group, a thienyl group, a quinolyl group, a benzofuryl group, a dibenzofuryl group, a benzothienyl group, a dibenzothienyl group, an indolyl group, a carbazolyl group, a carbolinyl group, a diazacarbazolyl group (a group obtained by substituting one of the carbon atoms constituting a carboline ring of a carbolinyl group with a nitrogen atom), a quinoxalinyl group, a pyridazinyl group, a triazinyl group, a quinazolyl group, an phthalazinyl group, and the like), a heterocyclic group (refers to a heteroaryl ring group or the like as well, for example, a pyrrolidyl group, an imidazolidyl group, a morpholyl group, or an oxazolidyl group), an alkoxy group (for example, methoxy, ethoxy, propyloxy, pentyloxy, hexyloxy, octyloxy, or dodecyloxy), a cycloalkoxy group (for example, cyclopentyloxy or cyclohexyloxy), an aryloxy group (for example, phenoxy or napthyloxy), an alkylthio group (for example, methylthio, ethylthio, propylthio, pentylthio, hexylthio, octylthio, or dodecylthio), a cycloalkylthio group (for example, cyclopentylthio or cyclohexylthio), an arylthio group (for example, phenylthio or naphthylthio), an alkoxycarbonyl group (for example, methylocycarbonyl, ethyloxycarbonyl, butyloxycarbonyl, octyloxycarbonyl, or dodecyloxycarbonyl), an aryloxycarbonyl group (for example, phenyloxycarbonyl or naphthyloxycarbonyl), a sulfamoyl group (for example, aminosulfonyl, methylaminosulfonyl, dimethylaminosulfonyl, butylaminosulfonyl, hexylaminosulfonyl, cyclohexylaminosulfonyl, octylaminosulfonyl, dodecylaminosulfonyl, phenylaminosulfonyl, naphthylaminosulfonyl, or 2-pyridylaminosulfonyl), an acyl group (for example, acetyl, ethylcarbonyl, propylcarbonyl, pentylcarbonyl, cyclohexylcarbonyl, octylcarbonyl, 2-ethylhexylcarbonyl, dodecylcarbonyl, phenylcarbonyl, naphthylcarbonyl, or pyridylcarbonyl), an acyloxy group (for example, acetyloxy, ethylcarbonyloxy, butylcarbonyloxy, octylcarbonyloxy, dodecylcarbonyloxy, or phenylcarbonyloxy), an amide group (for example, methylcarbonylamino, ethylcarbonylamino, dimethylcarbonylamino, propylcarbonylamino, pentylcarbonylamino, cyclohexyl carbonylamino, 2-ethylhexyl carbonylamino, octylcarbonylamino, dodecylcarbonylamino, phenylcarbonylamino, or naphthylcarbonylamino), a carbamoyl group (for example, aminocarbonyl, methylaminocarbonyl, dimethylaminocarbonyl, propylaminocarbonyl, pentylaminocarbonyl, cyclohexylaminocarbonyl, octylaminocarbonyl, 2-ethylhexylaminocarbonyl, dodecylaminocarbonyl, phenylaminocarbonyl, naphthylaminocarbonyl, or 2-pyridylaminocarbonyl), a ureido group (for example, methylureido, ethylureido, pentylureido, cyclohexylureido, octylureido, dodecylureido, phenylureido, naphthylureido, or 2-pyridylaminouredo), a sulfinyl group (for example, methylsulfinyl, ethylsulfinyl, butylsulfinyl, cyclohexylsulfinyl, 2-ethylhexylsulfinyl, dodecylsulfinyl, phenylsulfinyl, naphthylsulfinyl, or 2-pyridylsulfinyl), an alkylsulfonyl group (for example, methylsulfonyl, ethylsufonyl, butylsulfonyl, cyclohexylsulfonyl, 2-ethylhexylsulfonyl, or dodecylsulfonyl), an arylsulfonyl group (phenylsulfonyl, naphthylsulfonyl, or 2-pyridylsulfonyl), an amino group (for example, amino, ethylamino, dimethylamino, butylamino, cyclopentylamino, 2-ethylhexylamino, dodecylamino, anilino, naphthylamino, or 2-pyridylamino), a halogen atom (for example, a fluorine atom, a chlorine atom, or a bromine atom), a fluorohydrocarbon group (for example, fluoromethyl, trifluoromethyl, pentafluoroethyl, or pentafluorophenyl), a cyano group, a nitro group, a hydroxy group, a mercapto group, a silyl group (for example, trimethylsilyl, triisopropylsilyl, triphenylsilyl, or phenyldiethylsilyl), a group represented by the following Formula (SG1) (here, $X^A$ represents Ge or Sn), and the like.

These substituents may further have a plurality of substituents. Examples of the plurality of substituents that the above substituents may have include substituents represented by $R^{41}$ to $R^{46}$, $X^{41}$, and $X^{42}$ described above.

It is preferable that $X^{41}$ and $X^{42}$ each independently represent a hydrogen atom, an alkyl group, or an alkoxy group.

$Z^{41}$ and $Z^{42}$ are preferably S.

Among the above acene compounds, a compound represented by the following Formula (A3) or (A4) is more preferable.

Formula (A3)

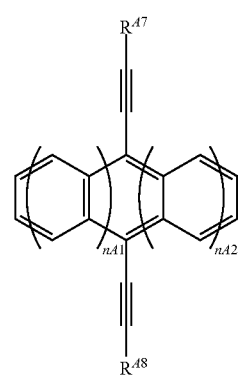

Formula (A4)

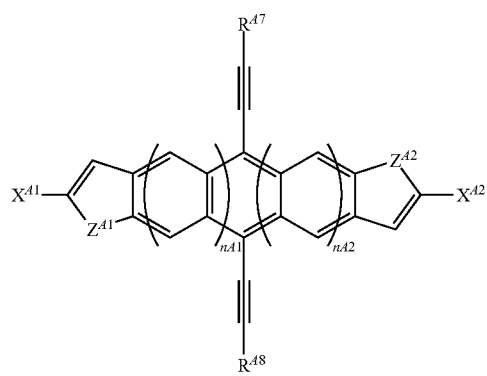

In the formulae, $R^{A7}$, $R^{A8}$, $X^{A1}$, and $X^{A2}$ each independently represent a hydrogen atom or a substituent, $Z^{A1}$ and $Z^{A2}$ each independently represent S, O, Se, or Te, and nA1 and nA2 each independently represent an integer of 0 to 3. Here, nA1 and nA2 do not simultaneously represent 0.

The substituents represented by $R^{A7}$ and $R^{A8}$ are preferably the substituents exemplified above as substituents which can be adopted as $R^{A1}$ to $R^{A6}$ in Formulae (A1) and (A2).

It is preferable that $X^{A1}$ and $X^{A2}$ each independently represent a hydrogen atom, an alkyl group, or an alkoxy group.

$Z^{A1}$ and $Z^{A2}$ are preferably S.

$R^{A7}$ and $R^{A8}$ in Formula (A3) or (A4) are preferably represented by the following Formula (SG1).

Formula (SG1)

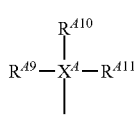

In the formula, $R^{A9}$ to $R^{A11}$ each independently represent a substituent, and $X^A$ represents Si, Ge, or Sn.

The substituents represented by $R^{A9}$ to $R^{A11}$ are preferably the substituents exemplified above as substituents which can be adopted as $R^{A1}$ to $R^{A6}$ in Formulae (A1) and (A2).

$R^{A9}$ to $R^{A11}$ preferably each independently represent an alkyl group having 1 to 8 carbon atoms, and more preferably each independently represent an alkyl group having 2 or 3 carbon atoms.

$X^A$ is preferably Si.

Specific examples of the compounds represented by Formulae (A1) to (A4) will be shown below, but the present invention is not limited thereto.

Compound A1

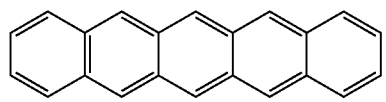

Compound A2

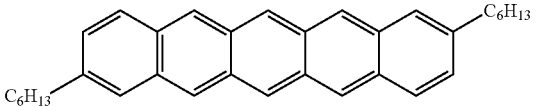

Compound A3

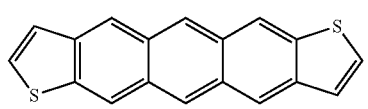

Compound A4

Compound A5
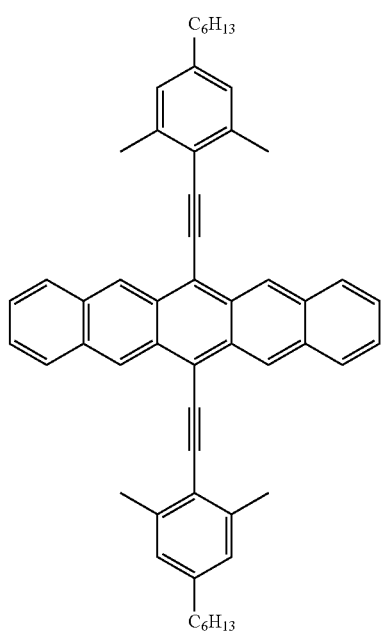
Compound A8
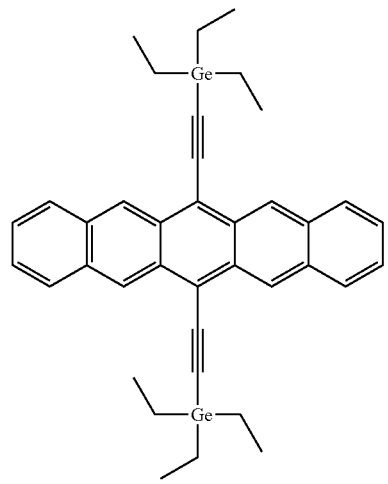
Compound A6
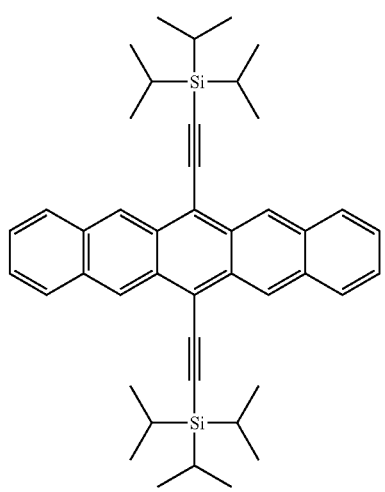
Compound A9
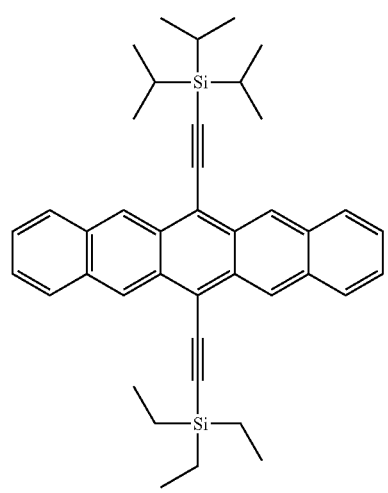
Compound A7
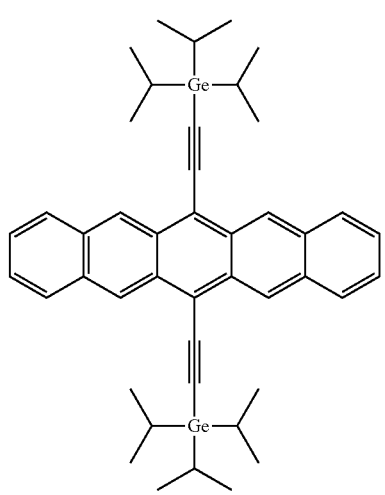
Compound A10
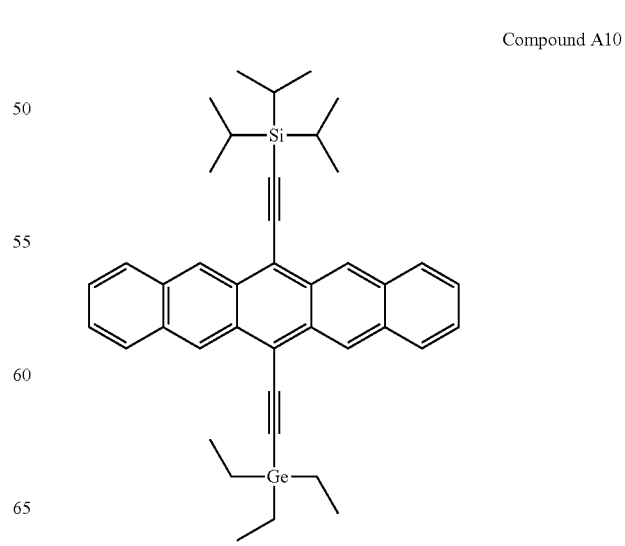

Compound A11
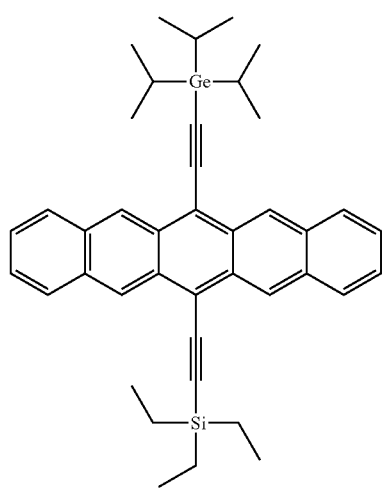
Compound A12
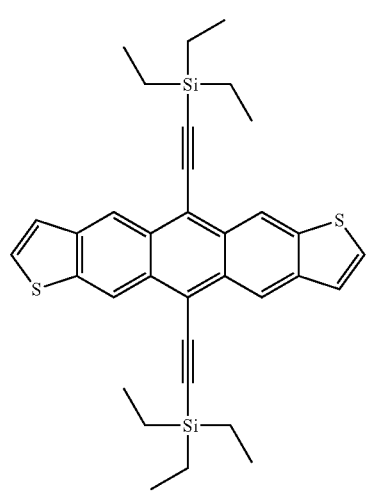
Compound A13
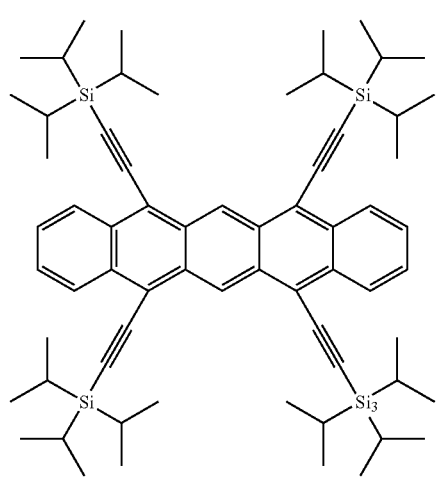
Compound A14
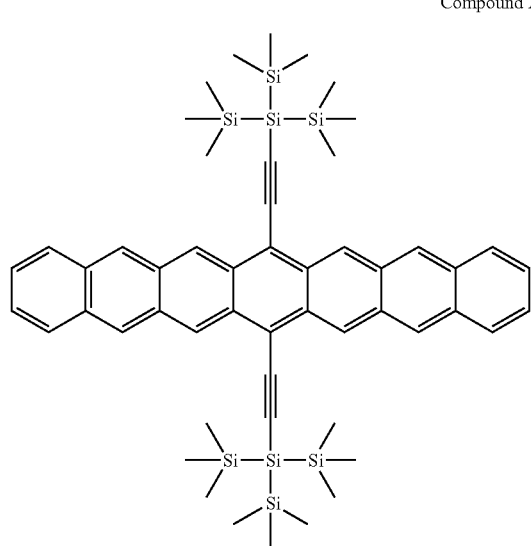
Compound A15
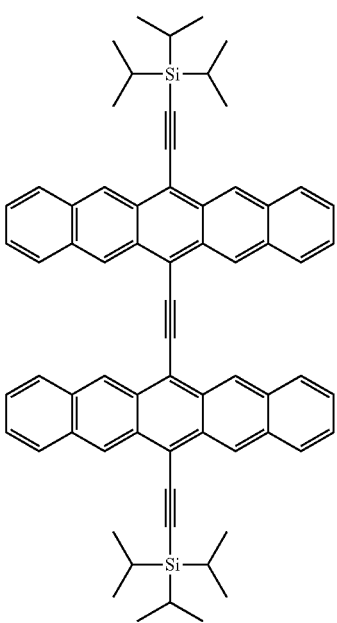

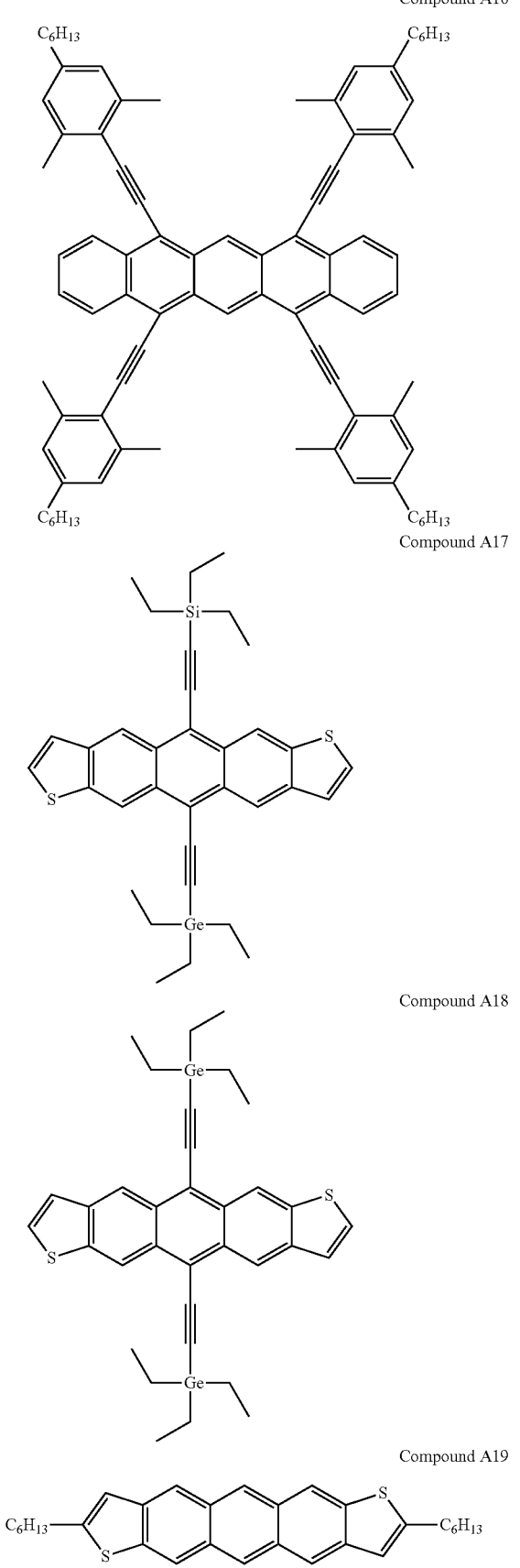
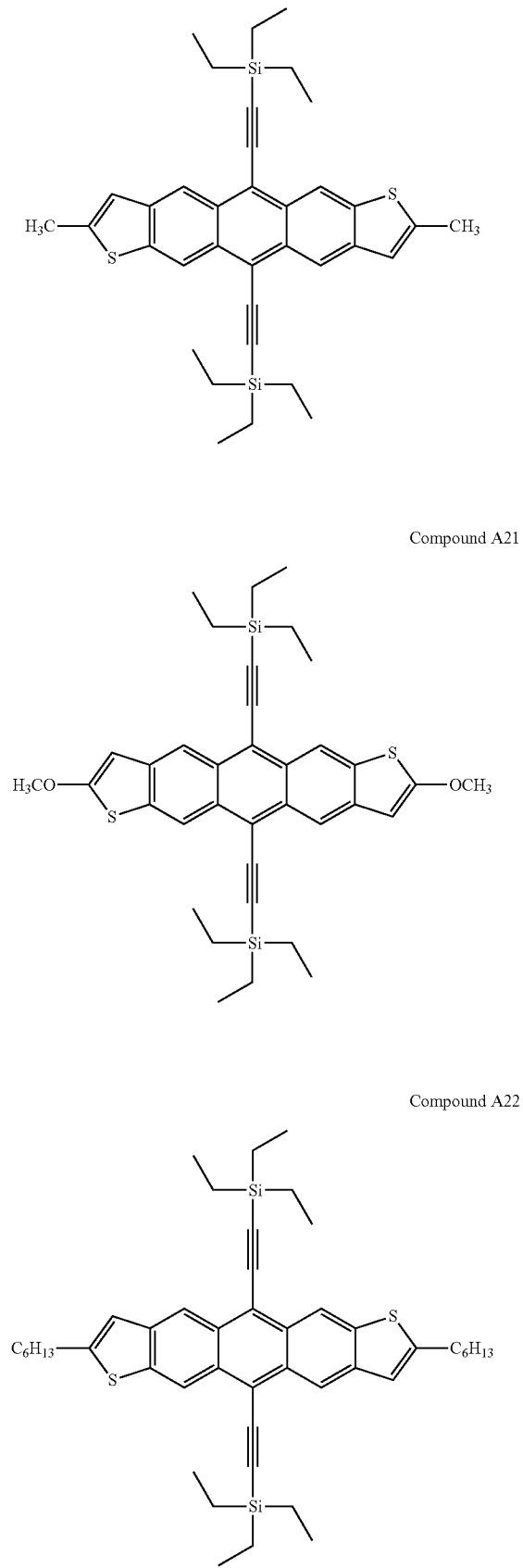

Compound A23
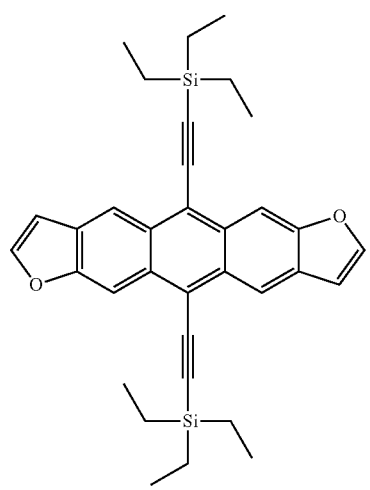
Compound A24
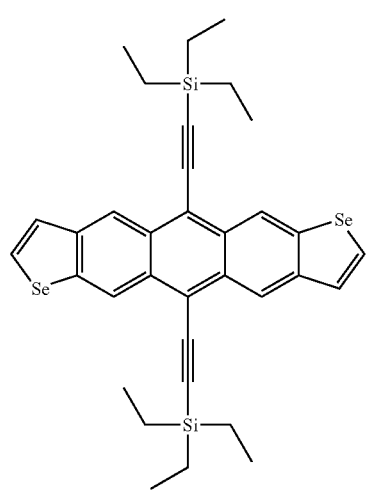
Compound A25
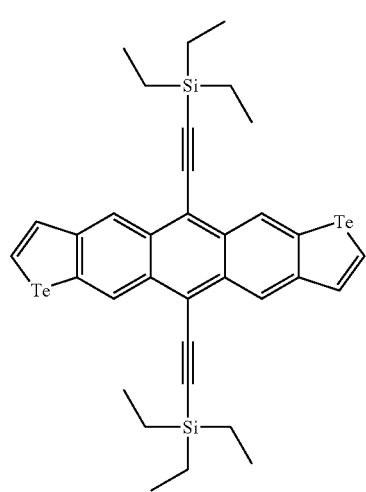
Compound A26
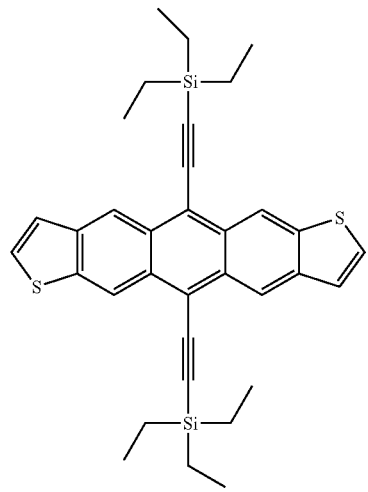
Compound A27
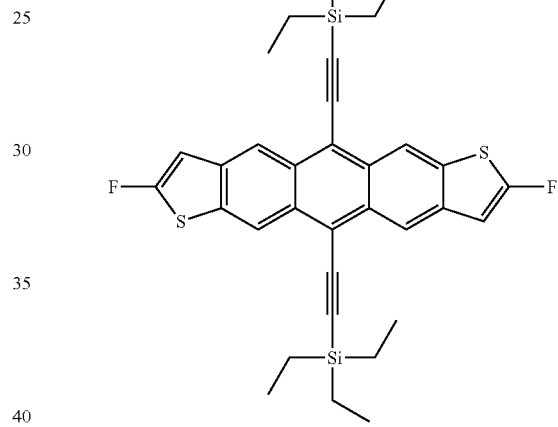
As the condensed polycylic aromatic compound, compounds represented by the following Formulae (C) to (H), Formulae (J) to (N), and Formulae (P) to (T) are also preferable.
Formula (C)
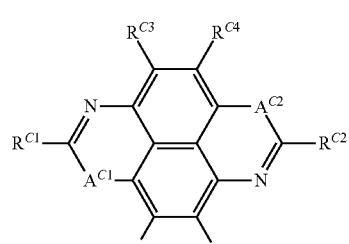
Formula (D)
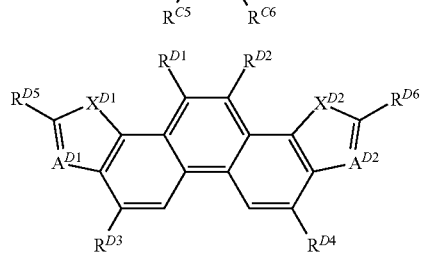

Formula (E)
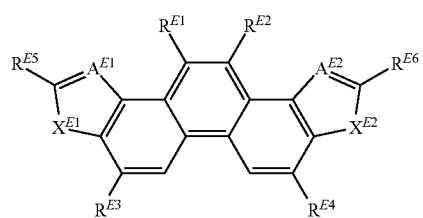
Formula (F)
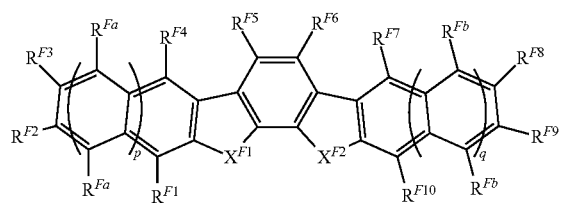
Formula (G)
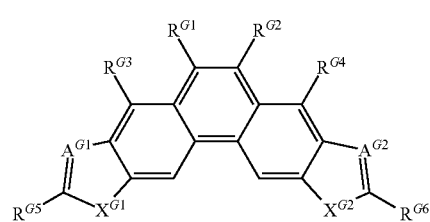
Formula (H)
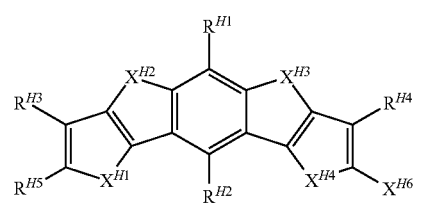
Formula (J)
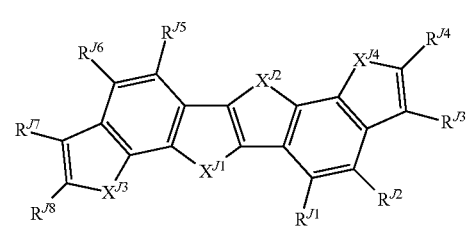
Formula (K)
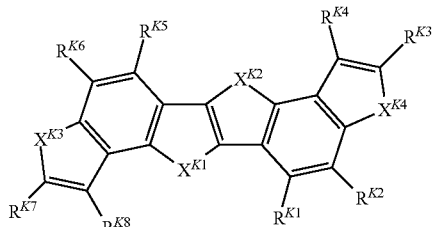
Formula (L)
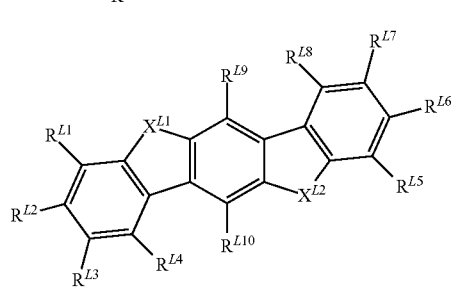
Formula (M)
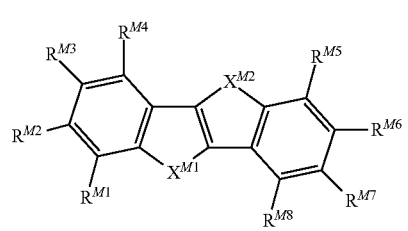
Formula (N)
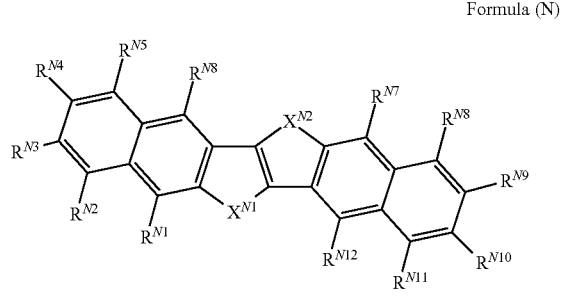
Formula (P)
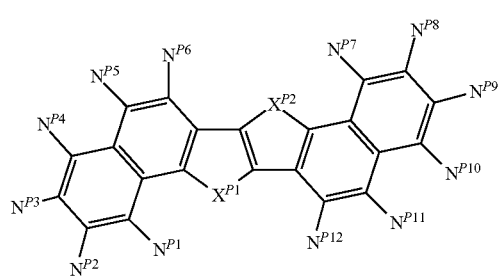
Formula (Q)
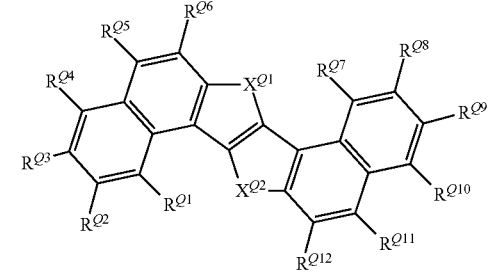
Formula (R)
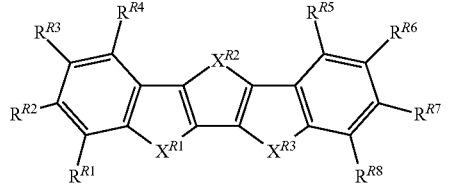
Formula (S)
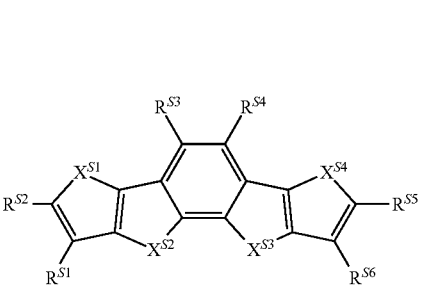

-continued

Formula (T)

[Chemical structure showing a fused ring system with substituents R^T1, R^T2, R^T3, R^T4, R^T5, R^T6 and X^T1, X^T2, X^T3, X^T4]

In Formula (C), $A^{C1}$ and $A^{C2}$ each independently represent an oxygen atom, a sulfur atom, or a selenium atom, $R^{C1}$ to $R^{C6}$ each independently represent a hydrogen atom or a substituent, and at least one of $R^{C1}$, $R^{C2}$, $R^{C3}$, $R^{C4}$, $R^{C5}$, or $R^{C6}$ is a substituent represented by the following Formula (W).

In Formula (C), $A^{C1}$ and $A^{C2}$ preferably both represent an oxygen atom or a sulfur atom, and more preferably both represent a sulfur atom.

In Formula (D), $X^{D1}$ and $X^{D2}$ each independently represent $NR^{D9}$, an oxygen atom, or a sulfur atom, $A^{D1}$ represents $CR^{D7}$ or a N atom, $A^{D2}$ represents $CR^{D8}$ or a N atom, $R^{D9}$ represents a hydrogen atom, an alkyl group, an alkenyl group, an alkynyl group, or an acyl group, $R^{D1}$ to $R^{D8}$ each independently represent a hydrogen atom or a substituent, and at least one of $R^{D1}$, $R^{D2}$, $R^{D3}$, $R^{D4}$, $R^{D5}$, $R^{D6}$, $R^{D7}$, or $R^{D8}$ is a substituent represented by the following Formula (W).

In Formula (E), $X^{E1}$ and $X^{E2}$ each independently represent an oxygen atom, a sulfur atom, or $NR^{E7}$, $A^{E1}$ and $A^{E2}$ each independently represent $CR^{E8}$ or a nitrogen atom, $R^{E1}$ to $R^{E8}$ each independently represent a hydrogen atom or a substituent, and at least one of $R^{E1}$, $R^{E2}$, $R^{E3}$, $R^{E4}$, $R^{E5}$, $R^{E6}$, $R^{E7}$, or $R^{E8}$ is a substituent represented by the following Formula (W).

In Formula (F), $X^{F1}$ and $X^{F2}$ each independently represent an oxygen atom, a sulfur atom, or a selenium atom, $R^{F1}$ to $R^{F10}$, $R^{Fa}$, and $R^{Fb}$ each independently represent a hydrogen atom or a substituent, at least one of $R^{F1}$, $R^{F2}$, $R^{F3}$, $R^{F4}$, $R^{F5}$, $R^{F6}$, $R^{F7}$, $R^{F8}$, $R^{F9}$, $R^{F10}$, $R^{Fa}$, or $R^{Fb}$ is a substituent represented by the following Formula (W), and p and q each independently represent an integer of 0 to 2.

In Formula (F), $X^{F1}$ and $X^{F2}$ preferably each independently represent an oxygen atom or a sulfur atom, and more preferably each independently represent a sulfur atom.

In Formula (G), $X^{G1}$ and $X^{G2}$ each independently represent $NR^{G9}$, an oxygen atom, or a sulfur atom, $A^{G1}$ represents $CR^{G7}$ or a N atom, $A^{G2}$ represents $CR^{G8}$ or a N atom, $R^{G9}$ represents a hydrogen atom, an alkyl group, an alkenyl group, an alkynyl group, an acyl group, an aryl group, or a heteroaryl group, $R^{G1}$ to $R^{G8}$ each independently represent a hydrogen atom or a substituent, and at least one of $R^{G1}$, $R^{G2}$, $R^{G3}$, $R^{G4}$, $R^{G5}$, $R^{G6}$, $R^{G7}$, or $R^{G8}$ is a substituent represented by the following Formula (W).

In Formula (H), $X^{H1}$ to $X^{H4}$ each independently represent $NR^{H7}$, an oxygen atom, or a sulfur atom, $R^{H7}$ represents a hydrogen atom, an alkyl group, an alkenyl group, an alkynyl group, an acyl group, an aryl group, or a heteroaryl group, $R^{H1}$ to $R^{H6}$ each independently represent a hydrogen atom or a substituent, and at least one of $R^{H1}$, $R^{H2}$, $R^{H3}$, $R^{H4}$, $R^{H5}$, or $R^{H6}$ is a substituent represented by the following Formula (W).

In Formula (H), $X^{H1}$ to $X^{H4}$ are preferably a sulfur atom.

In Formula (J), $X^{J1}$ and $X^{J2}$ each independently represent an oxygen atom, a sulfur atom, a selenium atom, or $NR^{J9}$, $X^{J3}$ and $X^{J4}$ each independently represent an oxygen atom, a sulfur atom, or a selenium atom, $R^{J1}$ to $R^{J9}$ each independently represent a hydrogen atom or a substituent, and at least one of $R^{J1}$, $R^{J2}$, $R^{J3}$, $R^{J4}$, $R^{J5}$, $R^{J6}$, $R^{J7}$, $R^{J8}$, or $R^{J9}$ is a substituent represented by the following Formula (W).

In Formula (J), $X^{J1}$, $X^{J2}$, $X^{J3}$, and $X^{J4}$ are preferably a sulfur atom.

In Formula (K), $X^{K1}$ and $X^{K2}$ each independently represent an oxygen atom, a sulfur atom, a selenium atom, or $NR^{K9}$, $X^{K3}$ and $X^{K4}$ each independently represent an oxygen atom, a sulfur atom, or a selenium atom, $R^{K1}$ to $R^{K9}$ each independently represent a hydrogen atom or a substituent, and at least one of $R^{K1}$, $R^{K2}$, $R^{K3}$, $R^{K4}$, $R^{K5}$, $R^{K6}$, $R^{K7}$, $R^{K8}$, or $R^{K9}$ is a substituent represented by the following Formula (W).

In Formula (K), $X^{K1}$, $X^{K2}$, $X^{K3}$, and $X^{K4}$ are preferably a sulfur atom.

In Formula (L), $X^{L1}$ and $X^{L2}$ each independently represent an oxygen atom, a sulfur atom, or $NR^{L11}$, $R^{L1}$ to $R^{L11}$ each independently represent a hydrogen atom or a substituent, and at least one of $R^{L1}$, $R^{L2}$, $R^{L3}$, $R^{L4}$, $R^{L5}$, $R^{L6}$, $R^{L7}$, $R^{L8}$, $R^{L9}$, $R^{L10}$, or $R^{L11}$ is a substituent represented by the following Formula (W).

In Formula (L), $X^{L1}$ and $X^{L2}$ preferably each independently represent an oxygen atom or a sulfur atom.

In Formula (M), $X^{M1}$ and $X^{M2}$ each independently represent an oxygen atom, a sulfur atom, a selenium atom, or $NR^{M9}$, $R^{M1}$ to $R^{M9}$ each independently represent a hydrogen atom or a substituent, and at least one of $R^{M1}$, $R^{M2}$, $R^{M3}$, $R^{M4}$, $R^{M5}$, $R^{M6}$, $R^{M7}$, $R^{M8}$, or $R^{M9}$ is a substituent represented by the following Formula (W).

In Formula (M), $X^{M1}$ and $X^{M2}$ are preferably a sulfur atom.

In Formula (N), $X^{N1}$ and $X^{N2}$ each independently represent an oxygen atom, a sulfur atom, a selenium atom, or $NR^{N13}$, $R^{N1}$ to $R^{N13}$ each independently represent a hydrogen atom or a substituent, and at least one of $R^{N1}$, $R^{N2}$, $R^{N3}$, $R^{N4}$, $R^{N5}$, $R^{N6}$, $R^{N7}$, $R^{N8}$, $R^{N9}$, $R^{N10}$, $R^{N11}$, $R^{N12}$, or $R^{N13}$ is a substituent represented by the following Formula (W).

In Formula (N), $X^{N1}$ and $X^{N2}$ are preferably a sulfur atom.

In Formula (P), $X^{P1}$ and $X^{P2}$ each independently represent an oxygen atom, a sulfur atom, a selenium atom, or $NR^{P13}$, $R^{P1}$ to $R^{P13}$ each independently represent a hydrogen atom or a substituent, and at least one of $R^{P1}$, $R^{P2}$, $R^{P3}$, $R^{P4}$, $R^{P5}$, $R^{P6}$, $R^{P7}$, $R^{P8}$, $R^{P9}$, $R^{P10}$, $R^{P11}$, $R^{P12}$, or $R^{P13}$ is a substituent represented by the following Formula (W).

In Formula (P), $X^{P1}$ and $X^{P2}$ are preferably a sulfur atom.

In Formula (Q), $X^{Q1}$ and $X^{Q2}$ each independently represent an oxygen atom, a sulfur atom, a selenium atom, or $NR^{Q13}$, $R^{Q1}$ to $R^{Q13}$ each independently represent a hydrogen atom or a substituent, and at least one of $R^{Q1}$, $R^{Q2}$, $R^{Q3}$, $R^{Q4}$, $R^{Q5}$, $R^{Q6}$, $R^{Q7}$, $R^{Q8}$, $R^{Q9}$, $R^{Q10}$, $R^{Q11}$, $R^{Q12}$, or $R^{Q13}$ is a substituent represented by the following Formula (W).

In Formula (Q), $X^{Q1}$ and $X^{Q2}$ are preferably a sulfur atom.

In Formula (R), $X^{R1}$, $X^{R2}$, and $X^{R3}$ each independently represent an oxygen atom, a sulfur atom, a selenium atom, or $NR^{R9}$, $R^{R1}$ to $R^{R9}$ each independently represent a hydrogen atom or a substituent, and at least one of $R^{R1}$, $R^{R2}$, $R^{R3}$, $R^{R4}$, $R^{R5}$, $R^{R6}$, $R^{R7}$, $R^{R8}$, or $R^{R9}$ is a substituent represented by the following Formula (W).

In Formula (R), $X^{R1}$, $X^{R2}$, and $X^{R3}$ are preferably a sulfur atom.

In Formula (S), $X^{S1}$, $X^{S2}$, $X^{S3}$, and $X^{S4}$ each independently represent an oxygen atom, a sulfur atom, a selenium atom, or $NR^{S7}$, $R^{S1}$ to $R^{S7}$ each independently represent a hydrogen atom or a substituent, and at least one of $R^{S1}$, $R^{S2}$, $R^{S3}$, $R^{S4}$, $R^{S5}$, $R^{S6}$, or $R^{S7}$ is a substituent represented by the following Formula (W).

In Formula (S), $X^{S1}$, $X^{S2}$, $X^{S3}$, and $X^{S4}$ are preferably a sulfur atom.

In Formula (T), $X^{T1}$, $X^{T2}$, $X^{T3}$, and $X^{T4}$ each independently represent an oxygen atom, a sulfur atom, a selenium atom, or $NR^{77}$, $R^{T1}$ to $R^{T7}$ each independently represent a hydrogen atom or a substituent, and at least one of $R^{T1}$, $R^{T2}$, $R^{T3}$, $R^{T4}$, $R^{T5}$, $R^{T6}$, or $R^{T7}$ is a substituent represented by the following Formula (W).

In Formula (T), $X^{T1}$, $X^{T2}$, $X^{T3}$, and $X^{T4}$ are preferably a sulfur atom.

Hereinbelow, $R^{C1}$ to $R^{C6}$, $R^{D1}$ to $R^{D8}$, $R^{E1}$ to $R^{E8}$, $R^{F1}$ to $R^{F10}$, $R^{Fa}$ and $R^{Fb}$, $R^{G1}$ to $R^{G8}$, $R^{H1}$ to $R^{H6}$, $R^{J1}$ to $R^{J9}$, $R^{K1}$ to $R^{K9}$, $R^{L1}$ to $R^{L11}$, $R^{M1}$ to $R^{M9}$, $R^{N1}$ to $R^{N13}$, $R^{P1}$ to $R^{P13}$, $R^{Q1}$ to $R^{Q13}$, $R^{R1}$ to $R^{R9}$, $R^{S1}$ to $R^{S7}$, and $R^{T1}$ to $R^{T7}$ (hereinafter, referred to as substituents $R^C$ to $R^T$ as well) which represent a hydrogen atom or a substituent in Formulae (C) to (H), Formulae (J) to (N), and Formulae (P) to (T) will be described.

Examples of substituents that the substituents $R^C$ to $R^T$ can adopt include a halogen atom, an alkyl group (an alkyl group having 1 to 40 carbon atoms such as methyl, ethyl, propyl, butyl, pentyl, hexyl, heptyl, octyl, nonyl, decyl, undecyl, dodecyl, tridecyl, tetradecyl, or pentadecyl; here, the alkyl group includes 2,6-dimethyloctyl, 2-decyltetradecyl, 2-hexyldecyl, 2-ethyloctyl, 2-decyltetradecyl, 2-butyldecyl, 1-octylnonyl, 2-ethyloctyl, 2-octyltetradecyl, 2-ethylhexyl, cycloalkyl, bicycloalkyl, tricycloalkyl, and the like), an alkenyl group (including 1-pentenyl, cycloalkenyl, bicycloalkenyl, and the like), an alkynyl group (including 1-pentenyl, trimethylsilylethynyl, triethyl silylethynyl, tri-i-propylsilylethynyl, 2-p-propylphenylethynyl, and the like), an aryl group (including an aryl group having 6 to 20 carbon atoms such as phenyl, naphthyl, p-pentylphenyl, 3,4-dipentylphenyl, p-heptoxyphenyl, or 3,4-diheptoxyphenyl, and the like), a heterocyclic group (may be referred to as a hetero ring group, including 2-hexylfuranyl and the like), a cyano group, a hydroxy group, a nitro group, an acyl group (including hexanonyl, benzoyl, and the like), an alkoxy group (including butoxy and the like), an aryloxy group, a silyloxy group, a heterocyclic oxy group, an acyloxy group, a carbamoyloxy group, an amino group (including anilino), an acylamino group, an aminocarbonylamino group (including a ureido group), an alkoxy- and aryloxycarbonylamino group, an alkyl- and arylsulfonylamino group, a mercapto group, an alkyl- and arylthio group (including methylthio, octylthio, and the like), a heterocyclic thio group, a sulfamoyl group, a sulfo group, an alkyl- and arylsulfinyl group, an alkyl- and arylsulfonyl group, an alkyl- and aryloxycarbonyl group, a carbamoyl group, an aryl- and heterocyclic azo group, an imido group, a phoshino group, a phosphinyl group, a phosphinyloxy group, a phosphinylamino group, a phosphono group, a silyl group (such as a ditrimethylsiloxymethyl butoxy group), a hydrazino group, a ureido group, a boronic acid group ($-B(OH)_2$), a phosphato group ($-OPO(OH)_2$), a sulfato group ($-OSO_3H$), and other known substituents.

These substituents may further have the substituents described above.

Among these, as the substituents that the substituents $R^C$ to $R^T$ can adopt, an alkyl group, an aryl group, an alkenyl group, an alkynyl group, a heterocyclic group, an alkoxy group, an alkylthio group, or a group represented by Formula (W) which will be described later is preferable, an alkyl group having 1 to 12 carbon atoms, an aryl group having 6 to 20 carbon atoms, an alkenyl group having 2 to 12 carbon atoms, an alkynyl group having 2 to 12 carbon atoms, an alkoxy group having 1 to 11 carbon atoms, a heterocyclic group having 5 to 12 carbon atoms, an alkylthio group having 1 to 12 carbon atoms, or a group represented by Formula (W) which will be described later is more preferable, and a group represented by Formula (W) which will be described later is particularly preferable.

The alkyl group, the alkenyl group, the alkynyl group, the acyl group, and the aryl group as $R^{D9}$, $R^{G9}$, and $R^{H7}$ described above each have the same definition as the alkyl group, the alkenyl group, the alkynyl group, the acyl group, and the aryl group described as the substituents that the substituents $R^C$ to $R^T$ can adopt.

The heteroaryl group has the same definition as the heteroaryl group described as the substituent of $R^{41}$ to $R^{46}$ The group represented by Formula (W): $-L-R^W$ will be described.

In Formula (W), L represents a divalent linking group represented by any one of the following Formulae (L-1) to (L-25) or a divalent linking group in which two or more divalent linking groups represented by any one of the following Formulae (L-1) to (L-25) are bonded to each other. $R^W$ represents a substituted or unsubstituted alkyl group, a cyano group, a vinyl group, an ethynyl group, an oxyethylene group, an oligo-oxyethylene group in which a repetition number v of an oxyethylene unit is equal to or greater than 2, a siloxane group, an oligosiloxane group having two or more silicon atoms, or a substituted or unsubstituted trialkylsilyl group.

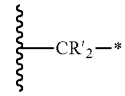

(L-1)

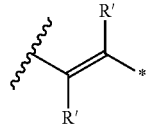

(L-2)

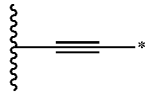

(L-3)

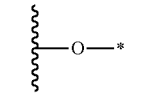

(L-4)

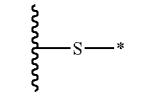

(L-5)

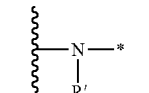

(L-6)

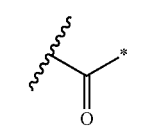

(L-7)

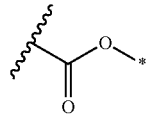

(L-8)

-continued (L-9) 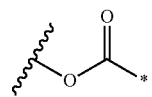

(L-10) 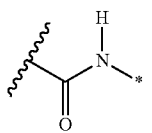

(L-11) 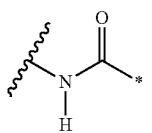

(L-12) 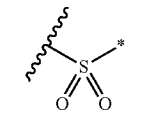

(L-13) 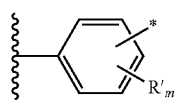

(L-14) 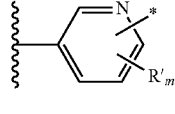

(L-15) 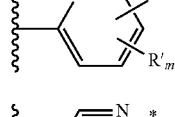

(L-16) 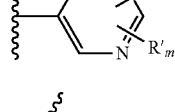

(L-17) 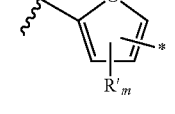

(L-18) 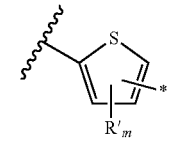

(L-19) 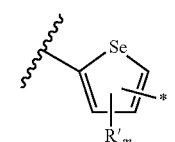

(L-20) 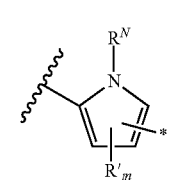

-continued (L-21) 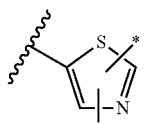

(L-22) 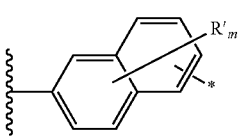

(L-23) 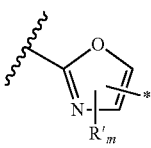

(L-24) 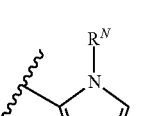

(L-25) 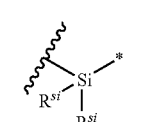

In Formulae (L-1) to (L-25), the portion of a wavy line represents a position in which the linking group is bonded to any one of the rings forming each skeleton represented by Formulae (C) to (H), Formulae (J) to (N), and Formulae (P) to (T) described above. In the present specification, in a case where L represents a divalent linking group in which two or more divalent linking groups represented by any one of Formulae (L-1) to (L-25) are bonded to each other, the portion of a wavy line may represent a position in which the linking group is bonded to any one of the rings forming each skeleton represented by Formulae (C) to (H), (J) to (N), or (P) to (T) described above and a position in which the linking group is bonded to any one of the divalent linking groups represented by Formulae (L-1) to (L-25).

* represents a position in which the linking group is bonded to Rw.

m in Formula (L-13) represents 4, m in Formulae (L-14) and (L-15) represents 3, and m in Formulae (L-16) to (L-20) represents 2, and m in Formula (L-22) represents 6.

R' in Formulae (L-1), (L-2), (L-6), (L-13) to (L-19), and (L-21) to (L-24) each independently represents a hydrogen atom or a substituent, and R' in Formulae (L-1) and (L-2) may each form a condensed ring by being bonded to $R^W$ adjacent to L.

$R^N$ represents a hydrogen atom or a substituent, $R^{si}$ each independently represents a hydrogen atom, an alkyl group, an alkenyl group, or an alkynyl group.

The divalent linking group represented by Formulae (L-17) to (L-21), (L-23), and (L-24) is more preferably a divalent linking group represented by the following Formulae (L-17A) to (L-21A), (L-23A), and (L-24A).

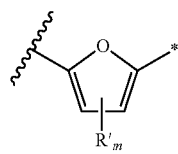

(L-17A)

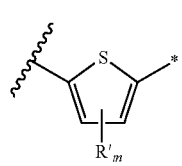

(L-18A)

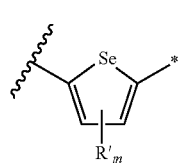

(L-19A)

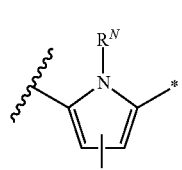

(L-20A)

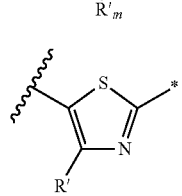

(L-21A)

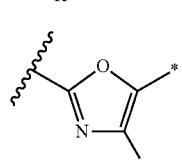

(L-23A)

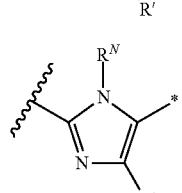

(L-24A)

In a case where a substituted or unsubstituted alkyl group, an oxyethylene group, an oligo-oxyethylene group in which a repetition number v of an oxyethylene unit is equal to or greater than 2, a siloxane group, an oligosiloxane group having two or more silicon atoms, or a substituted or unsubstituted trialkylsilyl group is present on the terminal of a substituent, the substituent can be interpreted as a substituent consisting only of —$R^W$ in Formula (W) or a substituent consisting of -L-$R^W$ in Formula (W).

In the present invention, in a case where a substituted or unsubstituted alkyl group having a main chain consisting of N carbon atoms is present on the terminal of a substituent, the substituent is interpreted as -L-$R^W$ in Formula (W) including as many linking groups as possible from the terminal of the substituent and is not interpreted as a substituent consisting only of —$R^W$ in Formula (W). Specifically, the substituent is interpreted as a substituent in which "one linking group represented by Formula (L-1) corresponding to L in Formula (W)" and "a substituted or unsubstituted alkyl group which corresponds to $R^W$ in Formula (W) and has a main chain consisting of (N−1) carbon atoms" are bonded to each other. For example, in a case where a n-octyl group which is an alkyl group having eight carbon atoms is present on the terminal of a substituent, the substituent is interpreted as a substituent in which one linking group represented by Formula (L-1), in which two R's represent hydrogen atoms, and a n-pentyl group having 7 carbon atoms are bonded to each other. Furthermore, in a case where the substituent represented by Formula (W) is an alkoxy group having eight carbon atoms, the substituent is interpreted as a substituent in which one linking group represented by Formula (L-4) as —O—, one linking group represented by Formula (L-1) in which two R's represent hydrogen atoms, and a n-heptyl group having seven carbon atoms are bonded to each other.

In contrast, in the present invention, in a case where an oxyethylene group, an oligo-oxyethylene group in which a repetition number v of an oxyethylene unit is equal to or greater than 2, a siloxane group, an oligosiloxane group having two or more silicon atoms, or a substituted or unsubstituted trialkylsilyl group is present on the terminal of a substituent, the substituent is interpreted as a substituent consisting only of $R^W$ in Formula (W) including as many linking groups as possible from the terminal of the substituent. For example, in a case where a —(OCH$_2$CH$_2$)—(OCH$_2$CH$_2$)—(OCH$_2$CH$_2$)—OCH$_3$ group is present on the terminal of a substituent, the substituent is interpreted as a substituent consisting only of an oligo-oxyethylene group in which a repetition number v of an oxyethylene unit is 3.

In a case where L forms a linking group in which divalent linking groups represented by any one of Formulae (L-1) to (L-25) are bonded to each other, the number of bonded divalent linking groups represented by any one of Formulae (L-1) to (L-25) is preferably 2 to 4, and more preferably 2 or 3.

Examples of the substituent R' in Formulae (L-1), (L-2), (L-6), and (L-13) to (L-24) include those exemplified as substituents that the substituents $R^C$ to $R^T$ of Formulae (C) to (H), (J) to (N), and (P) to (T) can adopt. The substituent R' in Formula (L-6) among the above formulae is preferably an alkyl group. In a case where R' in Formula (L-6) is an alkyl group, the number of carbon atoms in the alkyl group is preferably 1 to 9, more preferably 4 to 9 from the viewpoint of chemical stability and carrier transport properties, and even more preferably 5 to 9. In a case where R' in Formula (L-6) is an alkyl group, the alkyl group is preferably a linear alkyl group, because then THE carrier mobility can be improved.

Examples of $R^N$ include those exemplified as substituents that the substituents $R^C$ to $R^T$ can adopt. $R^N$ is preferably a hydrogen atom or a methyl group among the substituents.

$R^{si}$ is preferably an alkyl group. The alkyl group that $R^{si}$ can adopt is not particularly limited. A preferred range of the alkyl group that that $R^{si}$ can adopt is the same as a preferred range of an alkyl group that a silyl group can adopt in a case where $R^W$ represents the silyl group. The alkenyl group that $R^{si}$ can adopt is not particularly limited. The alkenyl group is preferably a substituted or unsubstituted alkenyl group and more preferably a branched alkenyl group, and the alkenyl group preferably has 2 or 3 carbon atoms. The alkynyl group that $R^{si}$ can adopt is not particularly limited. The alkynyl group is preferably a substituted or unsubstituted alkynyl group and more preferably a branched alkynyl group, and the alkynyl group preferably has 2 or 3 carbon atoms.

L is preferably a divalent linking group which is represented by any one of Formulae (L-1) to (L-5), (L-13), (L-17), and (L-18) or a divalent linking group in which two or more divalent linking groups represented by any one of Formulae (L-1) to (L-5), (L-13), (L-17), and (L-18) are bonded to each other, more preferably a divalent linking group which is represented by any one of Formulae (L-1), (L-3), (L-13), and (L-18) or a divalent linking group in which two or more divalent linking groups represented by Formula (L-1), (L-3), (L-13), or (L-18) are bonded to each other, and particularly preferably a divalent linking group which is represented by Formula (L-1), (L-3), (L-13), or (L-18) or a divalent linking group in which a divalent linking group represented by any one of Formulae (L-3), (L-13), and (L-18) and a divalent linking group represented by Formula (L-1) are bonded to each other. It is preferable that, in the divalent linking group, in which a divalent linking group represented by any one of Formulae (L-3), (L-13), and (L-18) and a divalent linking group represented by Formula (L-1) are bonded to each other, the divalent linking group represented by Formula (L-1) is bonded to the $R^W$ side.

From the viewpoint of chemical stability and carrier transport properties, L is preferably a divalent linking group containing a divalent linking group represented by Formula (L-1), and more preferably a divalent linking group represented by Formula (L-1). It even more preferable that L is a divalent linking group represented by Formula (L-18) or (L-1) and bonded to $R^W$ through the divalent linking group represented by Formula (L-1), and $R^W$ is a substituted or unsubstituted alkyl group. It is particularly preferable that L is a divalent linking group represented by Formula (L-18A) or (L-1) and bonded to $R^W$ through the divalent linking group represented by Formula (L-1), and $R^W$ is a substituted or unsubstituted alkyl group.

In Formula (W), $R^W$ is preferably a substituted or unsubstituted alkyl group.

In Formula (W), in a case where L adjacent to $R^W$ is a divalent linking group which is represented by Formula (L-1), $R^W$ is preferably a substituted or unsubstituted alkyl group, an oxyethylene group, an oligo-oxyethylene group in which a repetition number of an oxyethylene unit is equal to or greater than 2, a siloxane group, or an oligosiloxane group having two or more silicon atoms, and more preferably a substituted or unsubstituted alkyl group.

In Formula (W), in a case where L adjacent to $R^W$ is a divalent linking group represented by any one of Formula (L-2) and Formulae (L-4) to (L-25), $R^W$ is more preferably a substituted or unsubstituted alkyl group.

In Formula (W), in a case where L adjacent to $R^W$ is a divalent linking group represented by Formula (L-3), $R^W$ is preferably a substituted or unsubstituted alkyl group or a substituted or unsubstituted silyl group.

In a case where $R^W$ is a substituted or unsubstituted alkyl group, the number of carbon atoms thereof is preferably 4 to 17, more preferably 6 to 14 from the viewpoint of chemical stability and carrier transport properties, and even more preferably 6 to 12. It is preferable that R is a long-chain alkyl group having carbon atoms within the above range, particularly, a long-chain linear alkyl group, because then the linearity of the molecule is improved, and hence the carrier mobility can be improved.

In a case where $R^W$ represents an alkyl group, the alkyl group may be linear, branched, or cyclic. It is preferable that the alkyl group is a linear alkyl group, because then the linearity of the molecule is improved, and hence the carrier mobility can be improved.

Particularly, from the viewpoint of improving the carrier mobility, $R^W$ and L in Formula (W) preferably form a combination in which L in Formulae (C) to (H), (J) to (N), and (P) to (T) is a divalent linking group represented by Formula (L-1) and $R^W$ is a linear alkyl group having 4 to 17 carbon atoms or a combination in which L is a divalent linking group, in which a divalent linking group represented by any one of Formulae (L-3), (L-13), and (L-18) and a divalent linking group represented by Formula (L-1) are bonded to each other, and $R^W$ is a linear alkyl group.

In a case where L is a divalent linking group represented by Formula (L-1) and $R^W$ is a linear alkyl group having 4 to 17 carbon atoms, $R^W$ is more preferably a linear alkyl group having 6 to 14 carbon atoms from the viewpoint of improving the carrier mobility, and particularly preferably a linear alkyl group having 6 to 12 carbon atoms.

In a case where L is a divalent linking group, in which a divalent linking group represented by any one of Formulae (L-3), (L-13), and (L-18) and a divalent linking group represented by Formula (L-1) are bonded to each other, and $R^W$ is a linear alkyl group, $R^W$ is more preferably a linear alkyl group having 4 to 17 carbon atoms, even more preferably a linear alkyl group having 6 to 14 carbon atoms from the viewpoint of chemical stability and carrier transport properties, and particularly preferably a linear alkyl group having 6 to 12 carbon atoms from the viewpoint of improving the carrier mobility.

In contrast, from the viewpoint of improving the solubility of the compound in an organic solvent, $R^W$ is preferably a branched alkyl group.

In a case where $R^W$ is an alkyl group having a substituent, examples of the substituent include a halogen atom and the like, and the halogen atom is preferably a fluorine atom. In a case where $R^W$ is an alkyl group having a fluorine atom, all of the hydrogen atoms of the alkyl group may be substituted with fluorine atoms such that a perfluoroalkyl group is formed. Here, $R^W$ is preferably an unsubstituted alkyl group.

In the present specification, in a case where $R^W$ is an ethyleneoxy group or an oligoethyleneoxy group, the "oligooxyethylene group" represented by $R^W$ refers to a group represented by $-(OCH_2CH_2)_vOY$ (the repetition number v of an oxyethylene unit represents an integer of equal to or greater than 2, and Y on the terminal represents a hydrogen atom or a substituent). In a case where Y on the terminal of the oligo-oxyethylene group is a hydrogen atom, the terminal becomes a hydroxy group. The repetition number v of the oxyethylene unit is preferably 2 to 4, and more preferably 2 or 3. It is preferable that the hydroxy group on the terminal of the oligo-oxyethylene group is sealed. That is, it is preferable that Y represents a substituent. In this case, the hydroxy group is preferably sealed with an alkyl group having 1 to 3 carbon atoms. That is, Y is preferably an alkyl group having 1 to 3 carbon atoms, more preferably a methyl group or an ethyl group, and particularly preferably a methyl group.

In a case where $R^W$ is a siloxane group or an oligosiloxane group, a repetition number of the siloxane unit is preferably 2 to 4, and more preferably 2 or 3. Furthermore, it is preferable that a hydrogen atom or an alkyl group is bonded to each Si atom). In a case where an alkyl group is bonded to the Si atom, the number of carbon atoms of the alkyl group is preferably 1 to 3. For example, it is preferable that a methyl group or an ethyl group is bonded to the Si atom. The same alkyl groups may be bonded to the Si atoms, or different alkyl groups or hydrogen atoms may be bonded to the Si atoms. All of the siloxane units constituting the oligosiloxane group may be the same as or different from each other, but it is preferable that all of them are the same as each other.

In a case where L adjacent to $R^W$ is a divalent linking group represented by Formula (L-3), $R^W$ is preferably a substituted or unsubstituted silyl group. In a case where $R^W$ is a substituted or unsubstituted silyl group, $R^W$ is particularly preferably a substituted silyl group. The substituent of the silyl group is not particularly limited, but is preferably a substituted or unsubstituted alkyl group and more preferably a branched alkyl group. In a case where $R^W$ is a trialkylsilyl group, the number of carbon atoms in the alkyl group bonded to each Si atom is preferably 1 to 3. For example, it is preferable that a methyl group, an ethyl group, or an isopropyl group is bonded to the Si atoms. The same alkyl groups or different alkyl groups may be bonded to the Si atom. In a case where $R^W$ is a trialkylsilyl group further having a substituent on an alkyl group, the substituent is not particularly limited.

In Formula (W), the total number of carbon atoms contained in L and $R^W$ is preferably 5 to 18. In a case where the total number of carbon atoms contained in L and $R^W$ is equal to or greater than the lower limit of the above range, the carrier mobility is improved, and the driving voltage is reduced. In a case where the total number of carbon atoms contained in L and $R^W$ is equal to or less than the upper limit of the above range, the solubility of the compound in an organic solvent is improved.

The total number of carbon atoms contained in L and $R^W$ is preferably 5 to 14, more preferably 6 to 14, even more preferably 6 to 12, and particularly preferably 8 to 12.

In each of the compounds represented by Formulae (C) to (H), (J) to (N), or (P) to (T), the number of groups represented by Formula (W) among the substituents $R^C$ to $R^T$ is preferably 1 to 4, because then the carrier mobility and the solubility of the compound in an organic solvent are improved, more preferably 1 or 2, and particularly preferably 2.

The position of the group represented by Formula (W) among the substituents $R^C$ to $R^T$ is not particularly limited.

In the compound represented by Formula (C), it is preferable that any one of $R^{C1}$, $R^{C2}$, $R^{C3}$, and $R^{C6}$ is the group represented by Formula (W). It is more preferable that both of $R^{C1}$ and $R^{C2}$ or both of $R^{C3}$ and $R^{C6}$ are the group represented by Formula (W).

In the compound represented by Formula (D), it is preferable that $R^{D6}$ is the group represented by Formula (W). It is more preferable that both of $R^{D5}$ and $R^{D6}$ are the group represented by Formula (W).

In the compound represented by Formula (E), it is preferable that $R^{E6}$ is the group represented by Formula (W). It is more preferable that both of $R^{E5}$ and $R^{E6}$ are the group represented by Formula (W). In a case where $R^{E5}$ and $R^{E6}$ are a substituent other than the group represented by Formula (W), two $R^{E7}$'s are preferably the group represented by Formula (W).

In the compound represented by Formula (F), at least any one of $R^{F2}$, $R^{F3}$, $R^{F8}$, or $R^{F9}$ is preferably the substituent represented by Formula (W).

In the compound represented by Formula (G), $R^{G5}$ or $R^{G6}$ is preferably the group represented by Formula (W), because then the carrier mobility is improved, and the solubility of the compound in an organic solvent is improved.

In the compound represented by Formula (H), it is preferable that $R^{H4}$ or $R^{H6}$ is the group represented by Formula (W). It is more preferable that $R^{H4}$ or $R^{H6}$ and $R^{H3}$ or $R^{H5}$ are preferably the group represented by Formula (W).

In the compound represented by Formula (J), it is preferable that $R^{J8}$ is the group represented by Formula (W). It is more preferable that both of $R^{J8}$ and $R^{J4}$ are the group represented by Formula (W).

In the compound represented by Formula (K), it is preferable that $R^{K7}$ is the group represented by Formula (W). It is more preferable that both of $R^{K7}$ and $R^{K3}$ are the group represented by Formula (W).

In the compound represented by Formula (L), at least one of $R^{L2}$, $R^{L3}$, $R^{L6}$, or $R^{L7}$ is more preferably the group represented by Formula (W).

In the compound represented by Formula (M), it is preferable that $R^{M2}$ is the group represented by Formula (W). It is more preferable that both of $R^{M2}$ and $R^{M6}$ are the group represented by Formula (W).

In the compound represented by Formula (N), it is preferable that $R^{N3}$ is the group represented by Formula (W). It is more preferable that both of $R^{N3}$ and $R^{N9}$ are the group represented by Formula (W).

In the compound represented by Formula (P), it is preferable that $R^{P3}$ is the group represented by Formula (W). It is more preferable that both of $R^{P3}$ and $R^{P9}$ are the group represented by Formula (W).

In the compound represented by Formula (Q), it is preferable that $R^{Q3}$ is the group represented by Formula (W). It is more preferable that both of $R^{Q3}$ and $R^{Q9}$ are the group represented by Formula (W).

In the compound represented by Formula (R), it is preferable that $R^{R2}$ is the group represented by Formula (W). It is more preferable that both of $R^{R2}$ and $R^{R7}$ are the group represented by Formula (W).

In the compound represented by Formula (S), it is preferable that $R^{S2}$ is the group represented by Formula (W). It is more preferable that both of $R^{S2}$ and $R^{S5}$ are the group represented by Formula (W).

In the compound represented by Formula (T), it is preferable that $R^{T2}$ is the group represented by Formula (W). It is more preferable that both of $R^{T2}$ and $R^{T5}$ are the group represented by Formula (W).

Among the substituents $R^C$ to $R^T$, the number of substituents other than the group represented by Formula (W) is preferably 0 to 4, and more preferably 0 to 2.

Specific examples of each of the compounds represented by Formulae (C) to (H), (J) to (N), or (P) to (T) will be shown below, but the compound that can be used in the present invention is not limited to the specific examples.

Specific examples of the compound C represented by Formula (C) will be shown below.

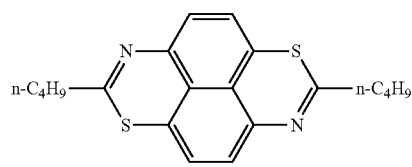

Compound C1

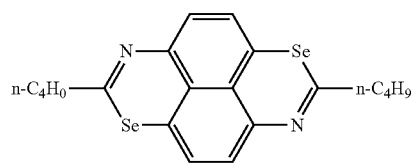

Compound C2

-continued
Compound C3
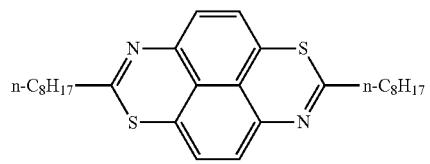
Compound C4
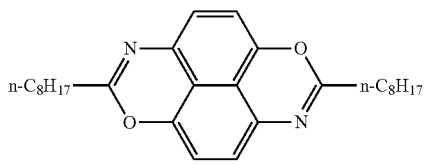
Compound C5
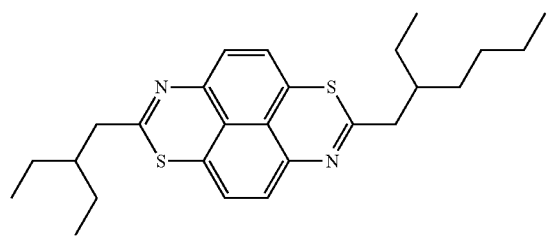
Compound C6
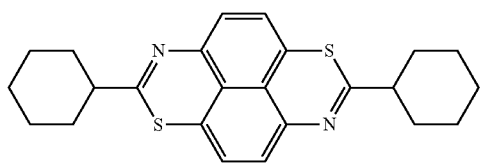
Compound C7
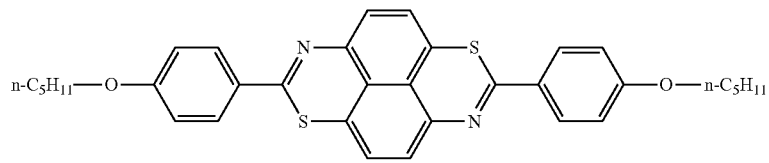
Compound C8
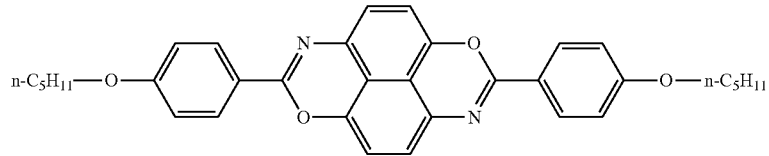
Compound C9
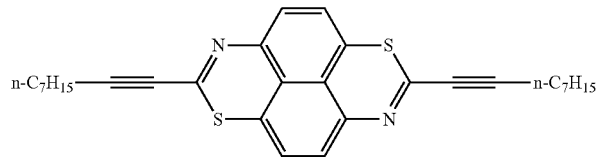
Compound C10
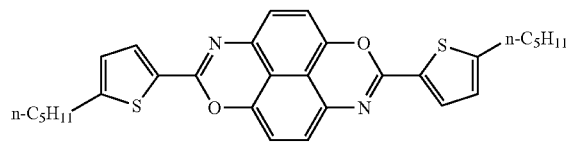
Compound C11
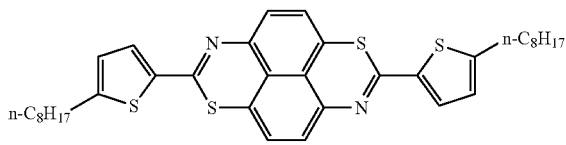
Compound C12
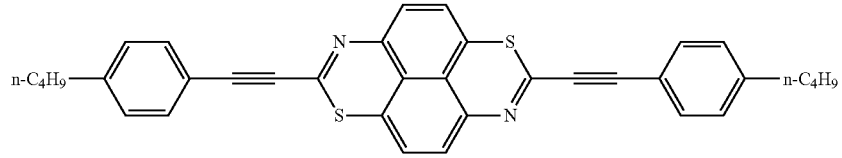
Compound C13
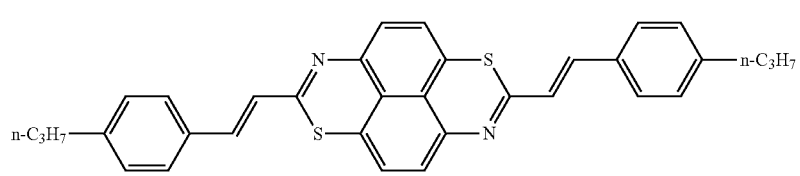

Compound C14

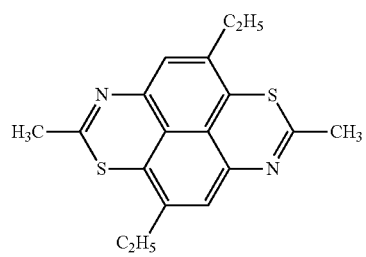

Compound C15

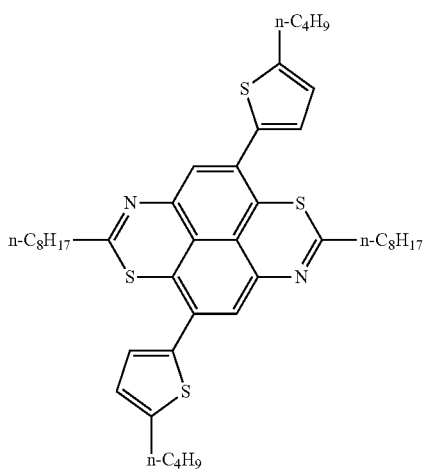

Compound C16

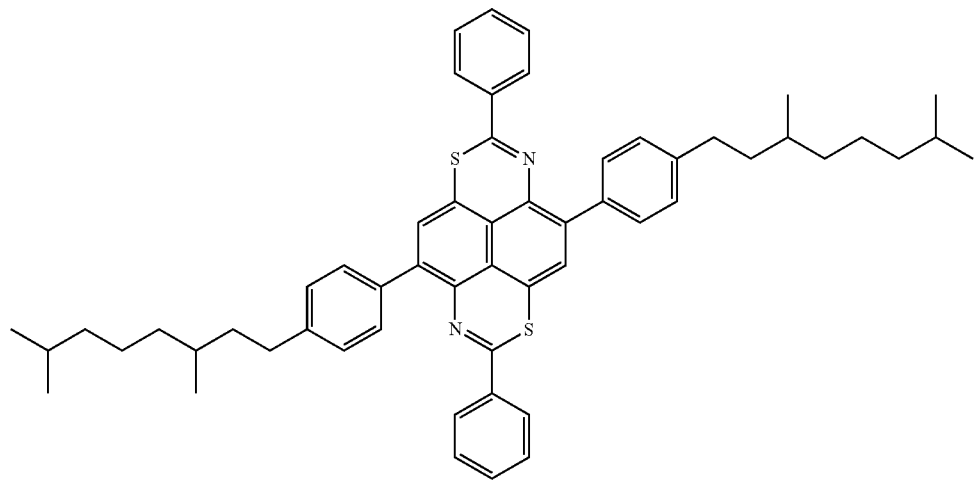

Compound C17

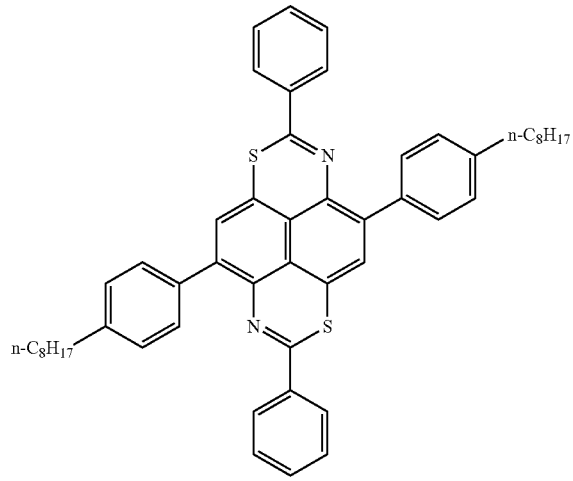

The molecular weight of the compound represented by Formula (C) is preferably equal to or less than 3,000, more preferably equal to or less than 2,000, even more preferably equal to or less than 1,000, and particularly preferably equal to or less than 850. In a case where the molecular weight is within the above range, the solubility of the compound in a solvent can be improved.

In contrast, from the viewpoint of the film quality stability of a thin film, the molecular weight is preferably equal to or greater than 300, more preferably equal to or greater than 350, and even more preferably equal to or greater than 400.

Specific examples of the compound D represented by Formula (D) will be shown below.

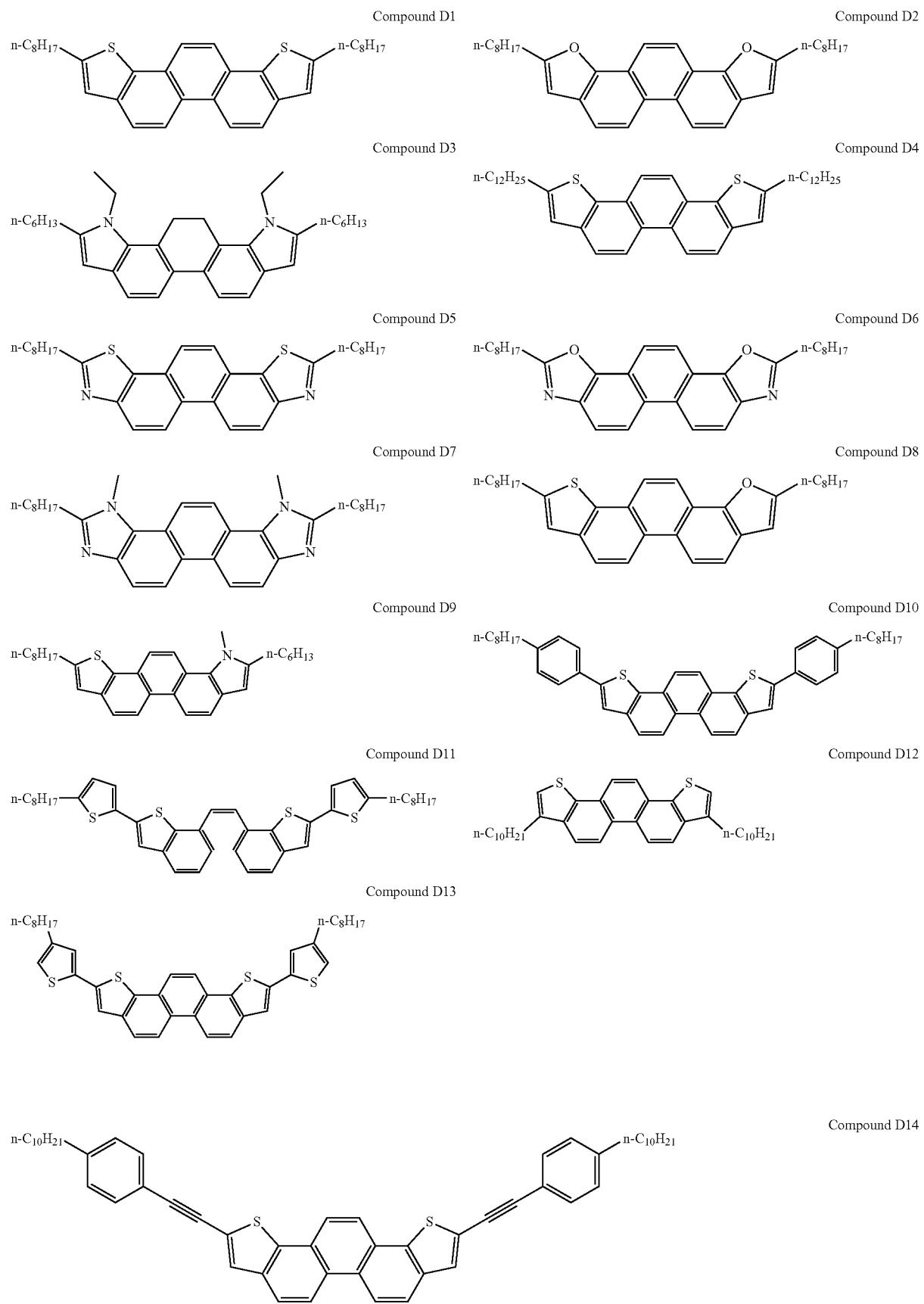

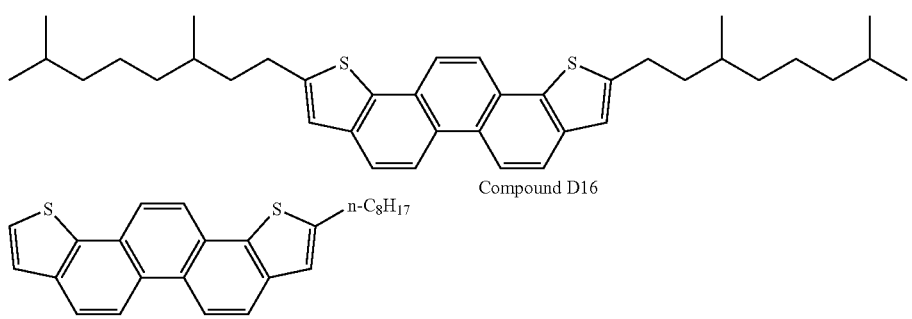

Compound D15

Compound D16

It is preferable that the upper limit of the molecular weight of the compound represented by Formula (D) is the same as the upper limit of the molecular weight of the compound represented by Formula (C), because then the solubility of the compound in a solvent can be improved. In contrast, from the viewpoint the film quality stability of a thin film, the molecular weight is preferably equal to or greater than 400, more preferably equal to or greater than 450, and even more preferably equal to or greater than 500.

Specific examples of each of the compound E represented by Formula (E), the compound F represented by Formula (F), the compound G represented by Formula (G), and the compound H represented by Formula (H) will be sequentially shown below.

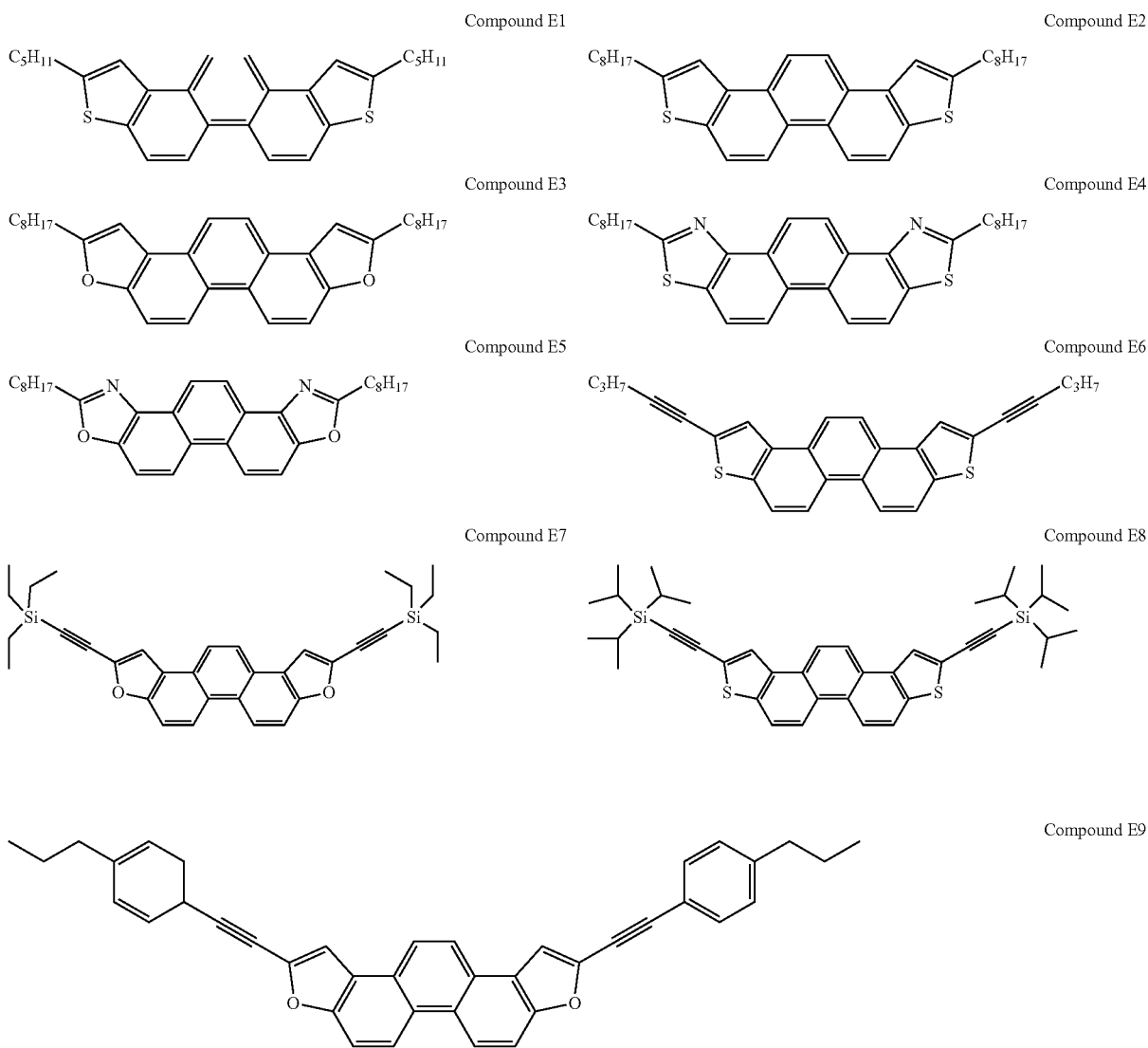

-continued
Compound E10
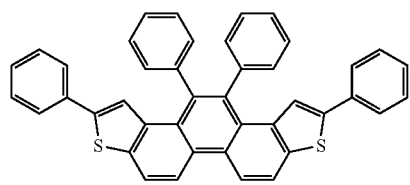
Compound E11
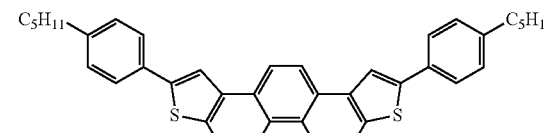
Compound E12
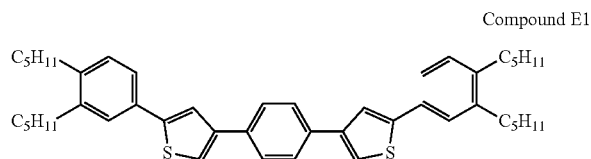
Compound E13
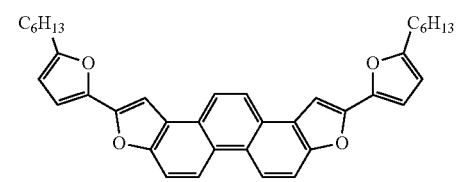
Compound E14
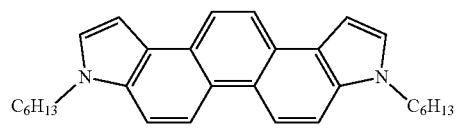
Compound F1
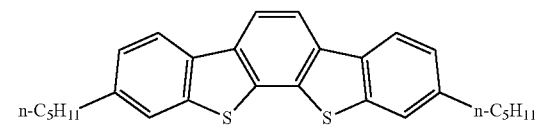
Compound F2
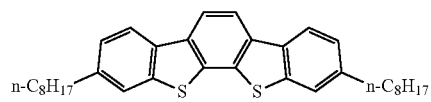
Compound F3
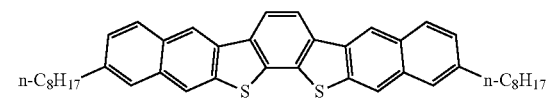
Compound F4
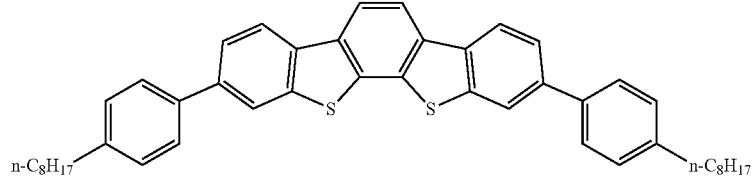
Compound F5
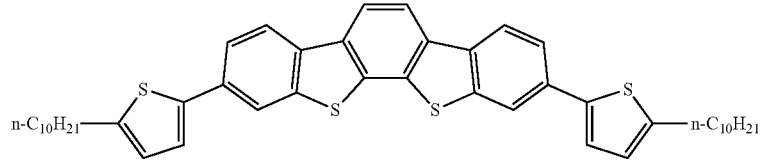
Compound F6
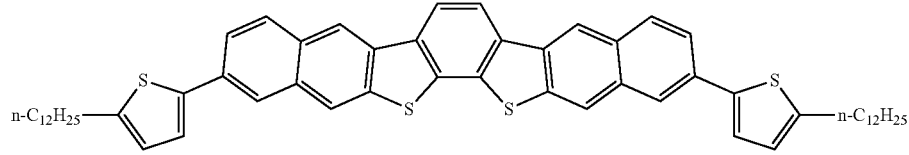
Compound F7
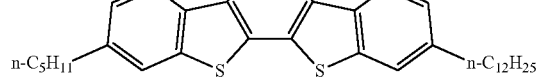
Compound F8
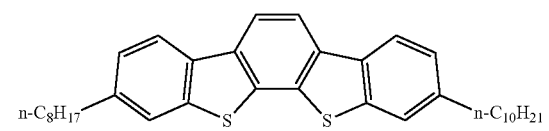
Compound F9
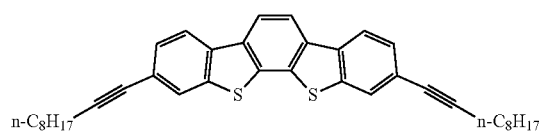
Compound F10
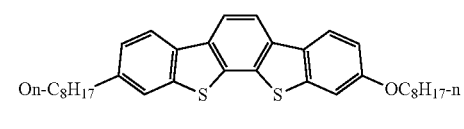

Compound F11
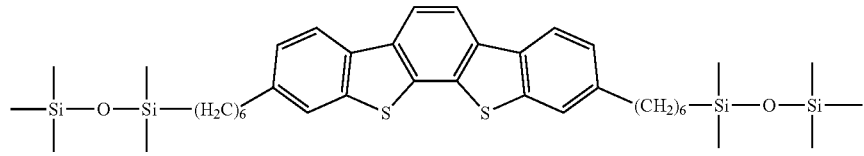
Compound F12
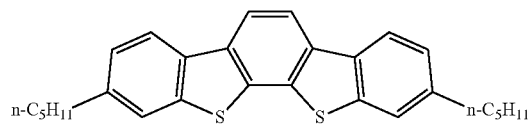
Compound G1
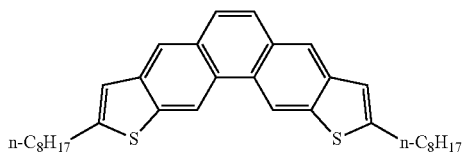
Compound G2
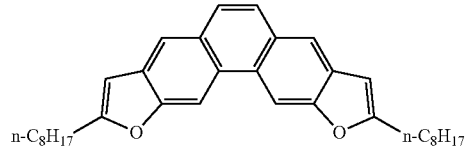
Compound G3
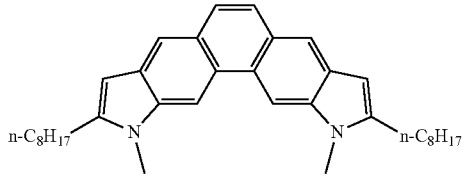
Compound G4
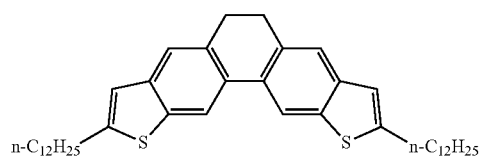
Compound G5
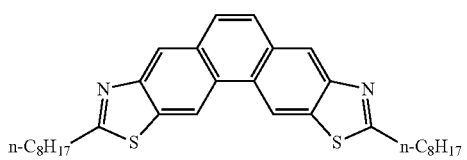
Compound G6
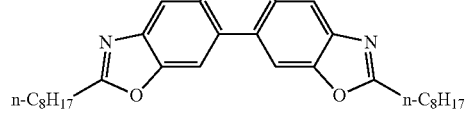
Compound G7
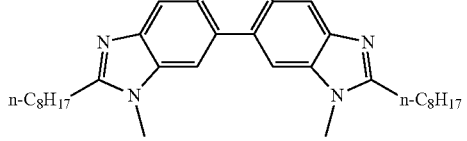
Compound G8
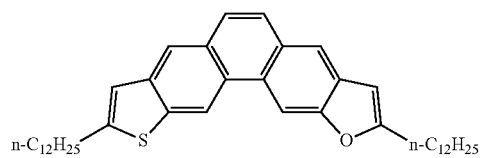
Compound G9
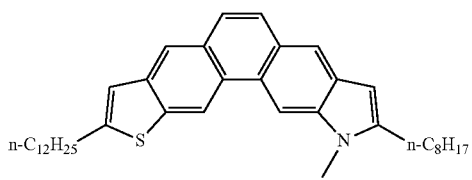
Compound G10
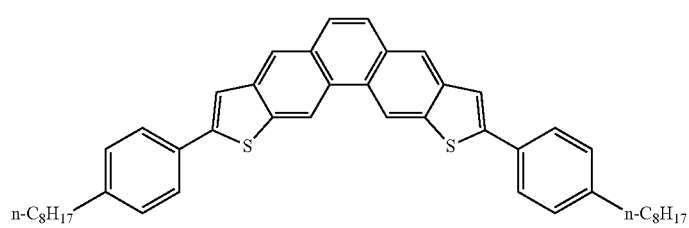
Compound G11
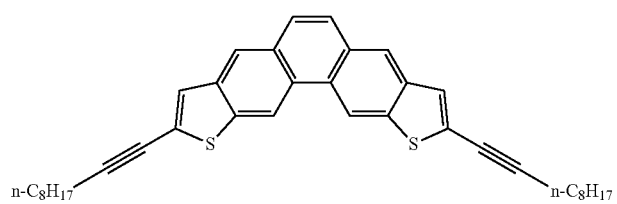

-continued
Compound G12
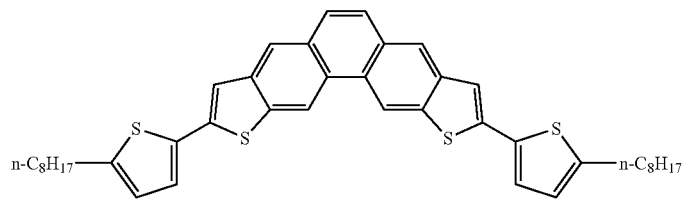
Compound G13
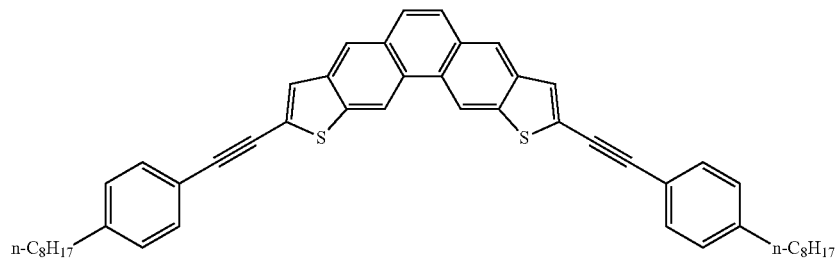
Compound G14
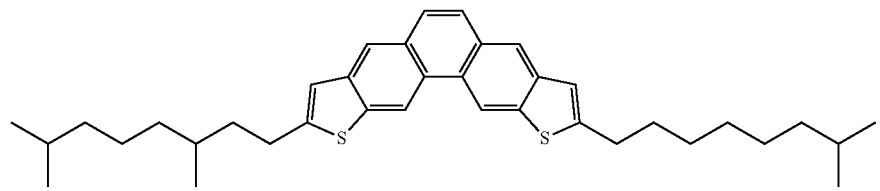
Compound G15
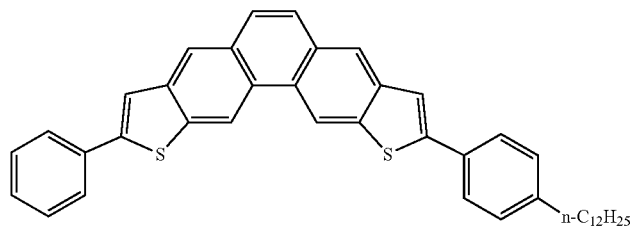
Compound H1
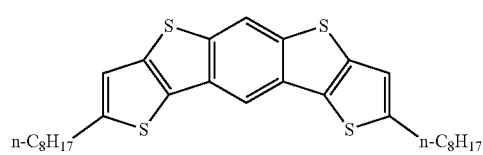
Compound H2
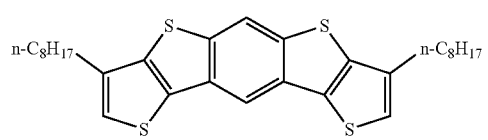
Compound H3
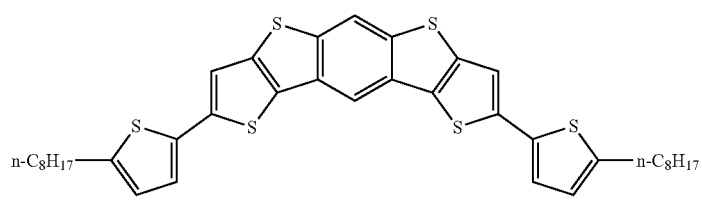
Compound H4
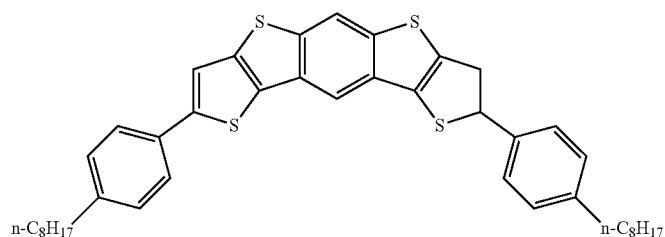

Compound H5

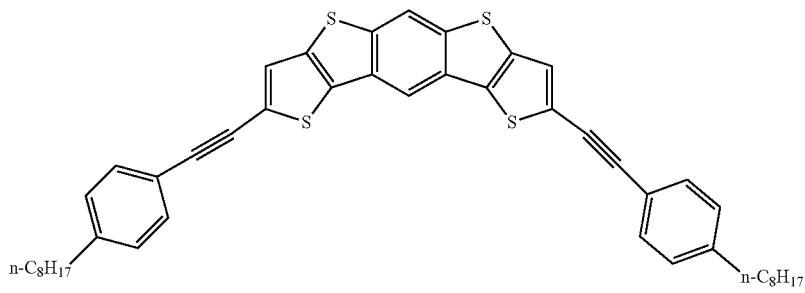

Compound H6

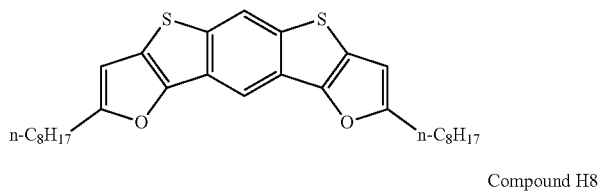

Compound H7

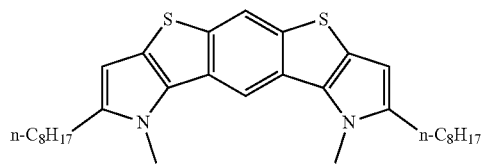

Compound H8

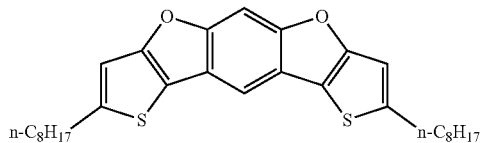

Compound H9

Compound H10

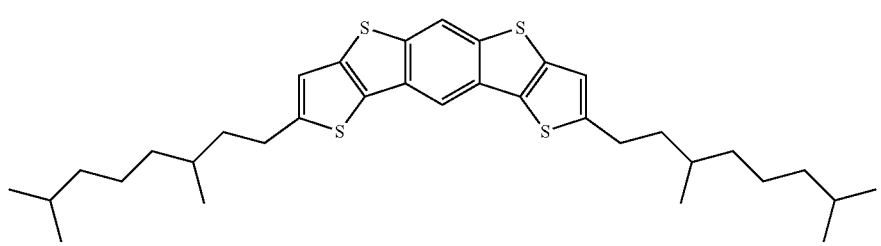

Compound H11

Compound H12

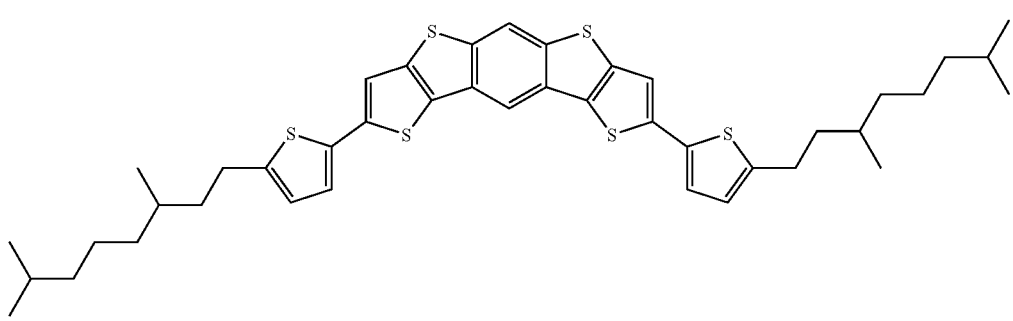

It is preferable that the upper limit of the molecular weight of each of the compound E, the compound F, the compound G, and the compound H is the same as the upper limit of the molecular weight of the compound C represented by Formula (C), because then the solubility of the compound in a solvent can be improved. In contrast, from the viewpoint of the film quality stability of a thin film, the lower limit of the molecular weight is the same as the lower limit of the molecular weight of the compound represented by Formula (D).

Specific examples of the compound J and the compound K represented by Formulae (J) and (K) will be shown below.

Compound J1
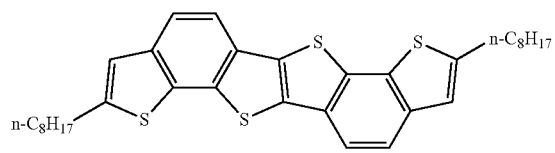
Compound J2
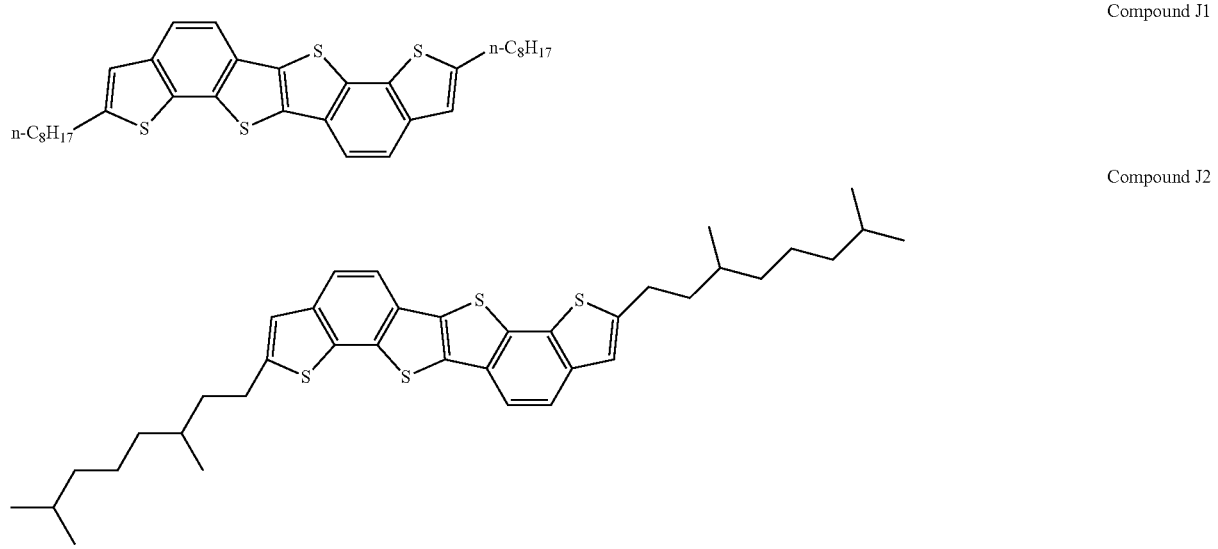
Compound J3
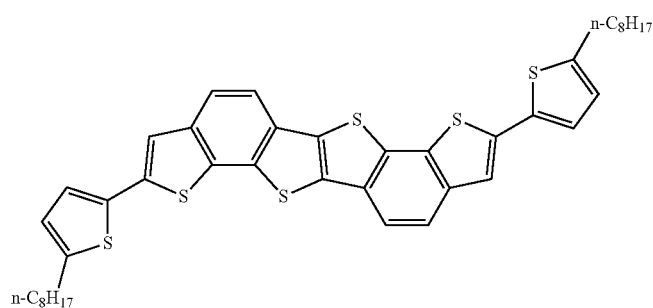
Compound J4
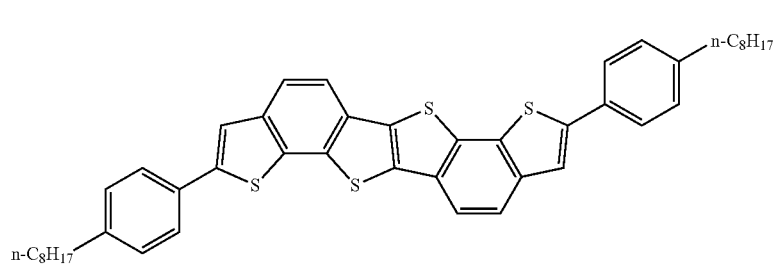
Compound J5
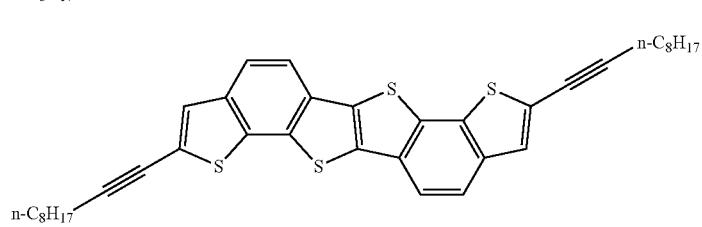
Compound J6
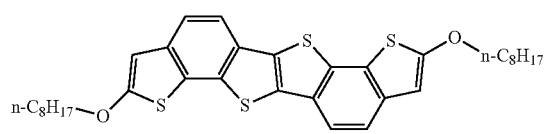
Compound J7
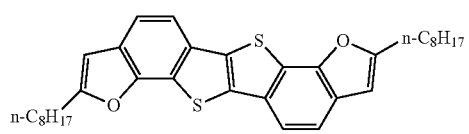
Compound J8
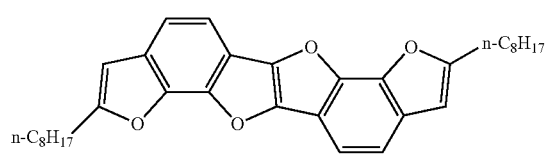
Compound K1
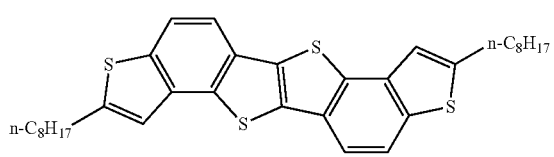

Compound K2

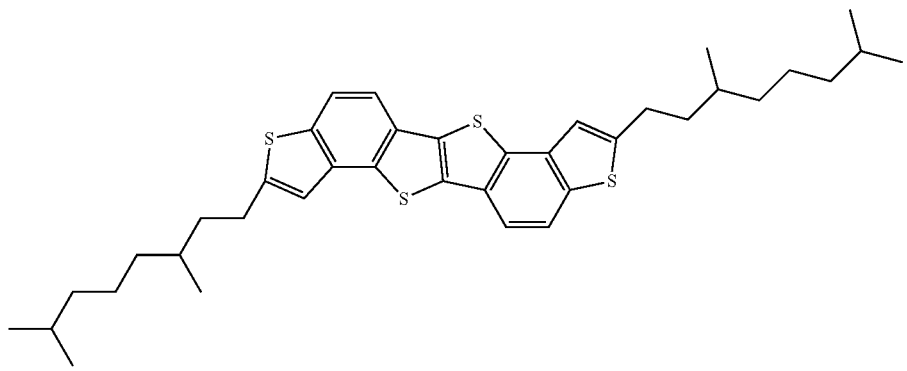

Compound K3

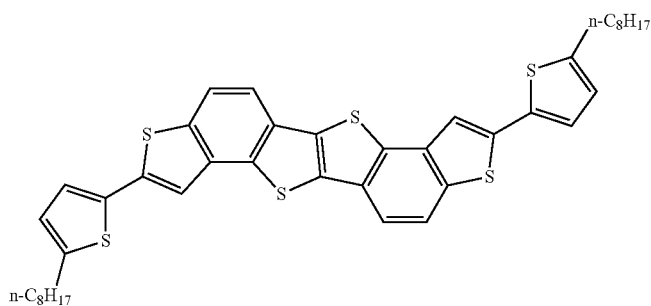

Compound K4

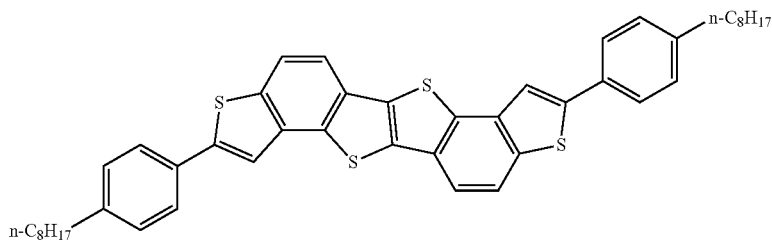

Compound K5

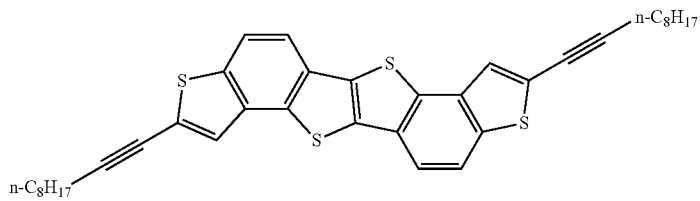

Compound K6

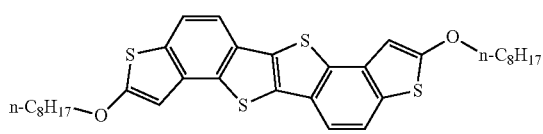

Compound K7

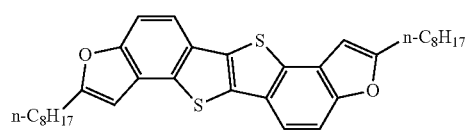

Compound K8

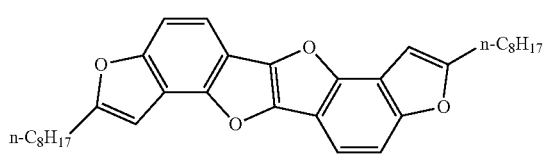

It is preferable that the upper limit of the molecular weight of each of the compound J and the compound K is the same as the upper limit of the molecular weight of the compound C represented by Formula (C), because then the solubility of the compound in a solvent can be improved. In contrast, from the viewpoint of the film quality stability of a thin film, the lower limit of the molecular weight is the same as the lower limit of the molecular weight of the compound represented by Formula (D).

Specific examples of each of the compound L represented by Formula (L), the compound M represented by Formula (M), the compound N represented by Formula (N), the compound P represented by Formula (P), and the compound Q represented by the Formula (Q) will be sequentially shown below.
Compound L1
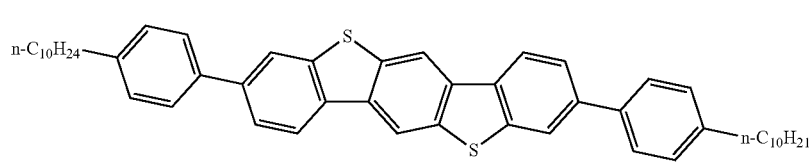
Compound L2
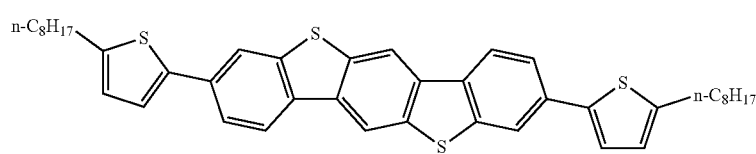
Compound L3
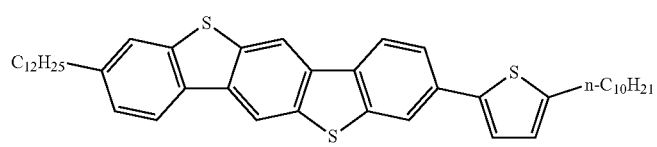
Compound L4
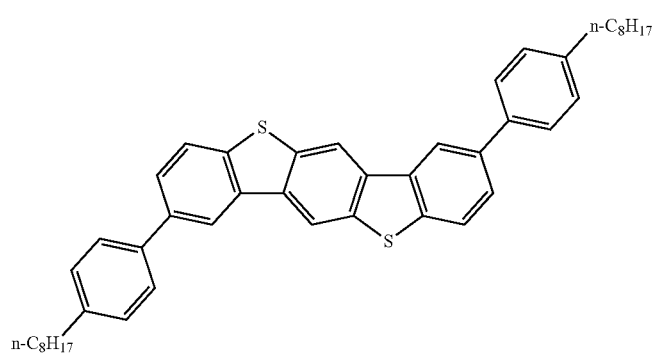
Compound L5
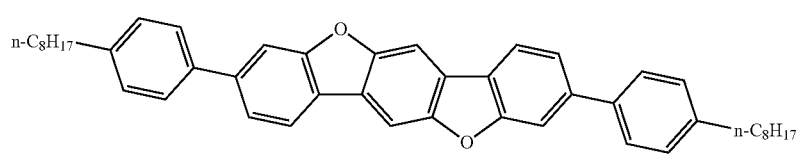
Compound L6
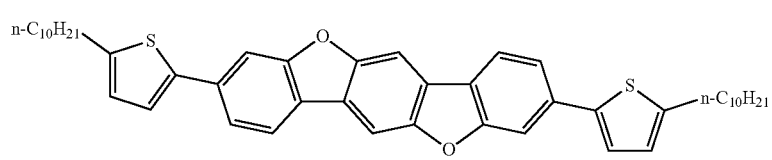
Compound L7
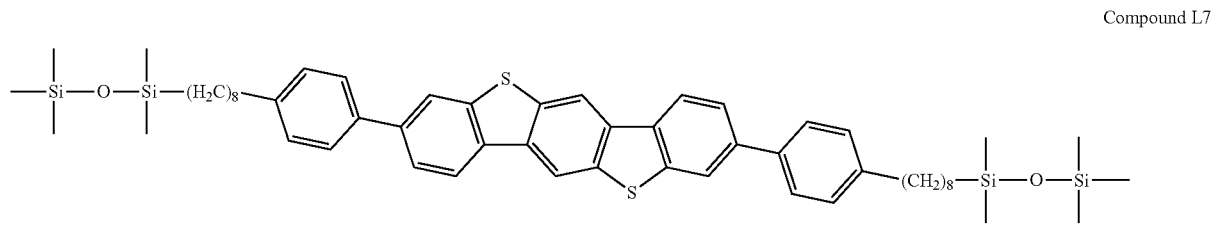

-continued
Compound L8
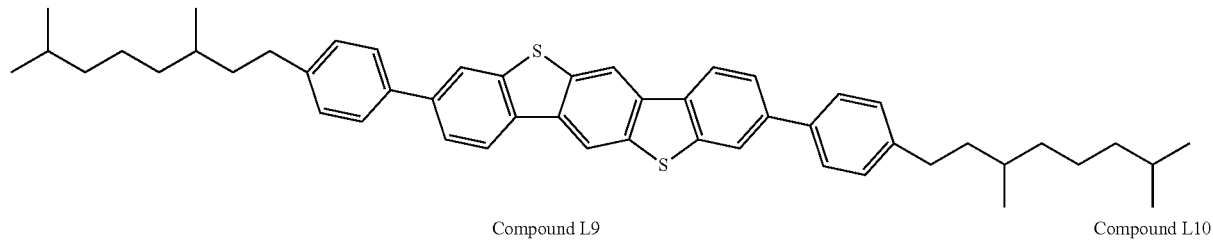
Compound L9
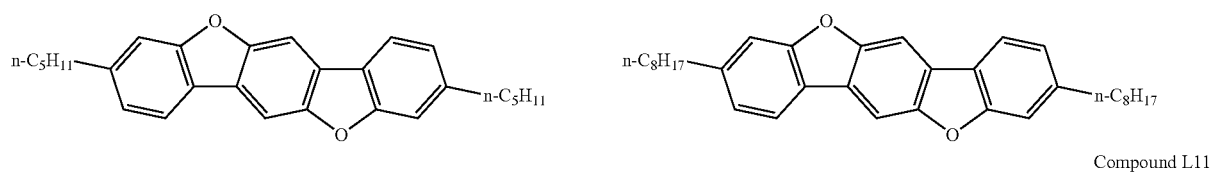
Compound L10
Compound L11
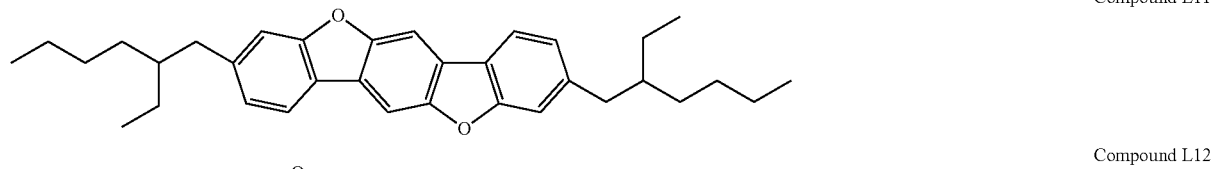
Compound L12
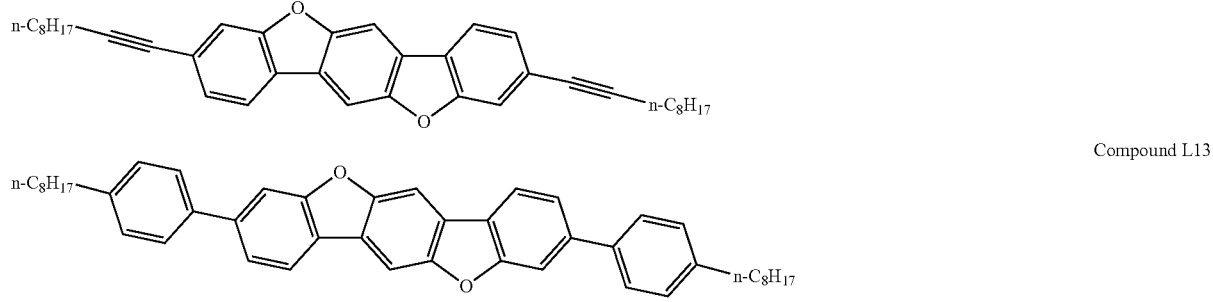
Compound L13
Compound L14
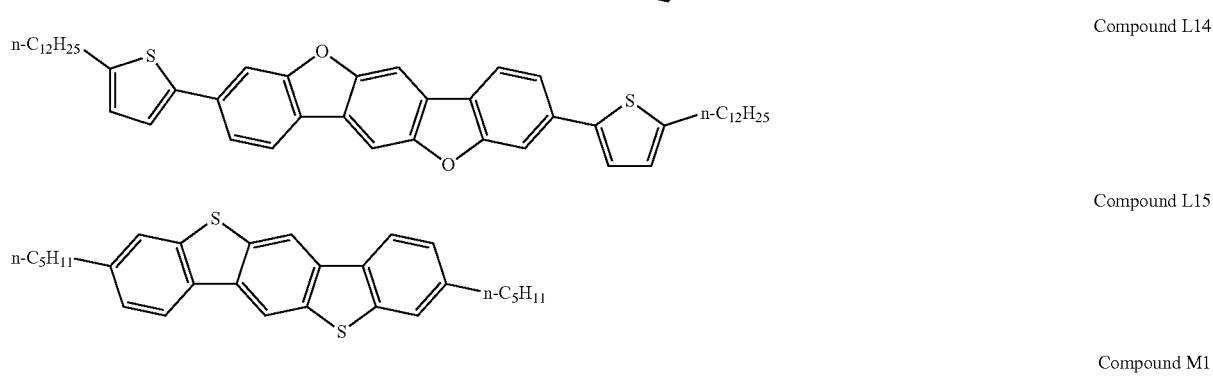
Compound L15
Compound M1
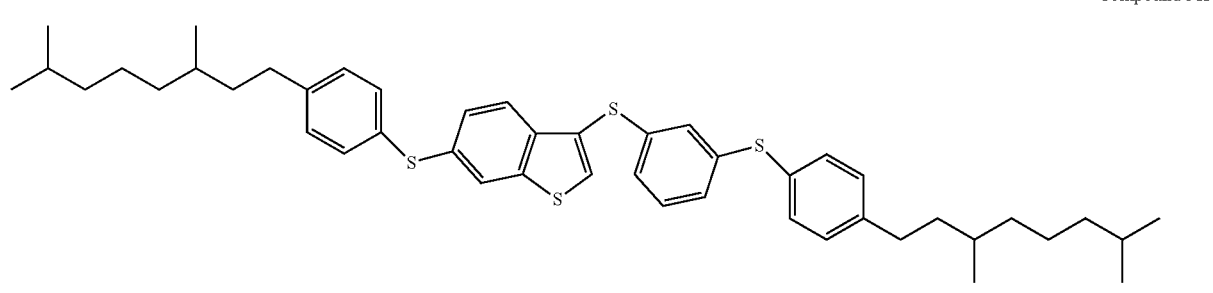
Compound M2
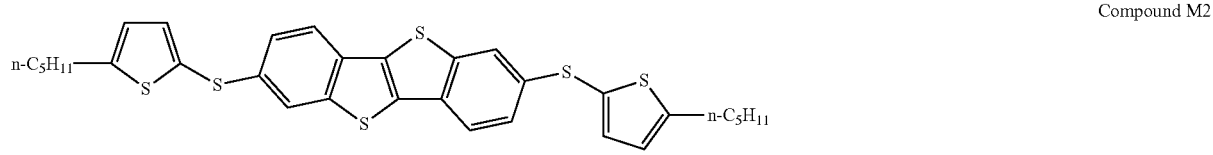

-continued
Compound M3 (C8BTBT)
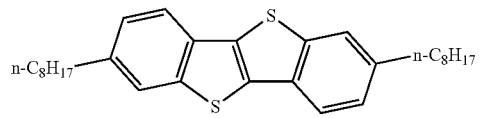
Compound M4
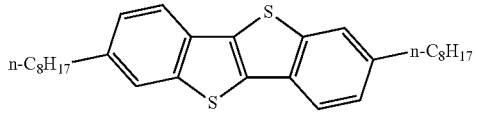
Compound M5
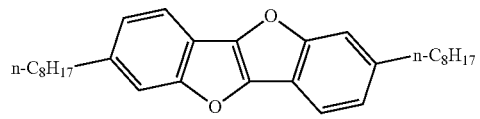
Compound M6
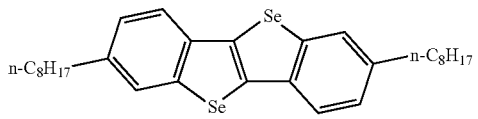
Compound M7
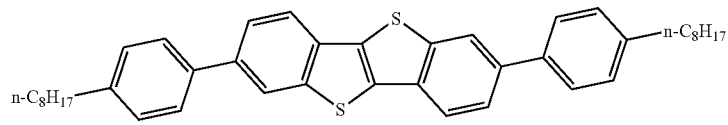
Compound M8
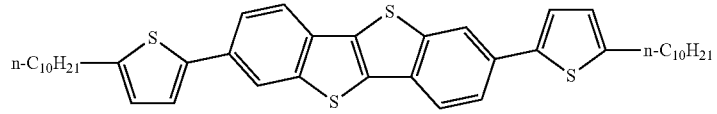
Compound N1
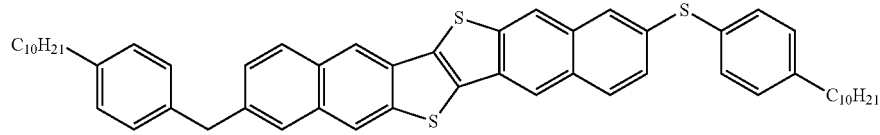
Compound N2
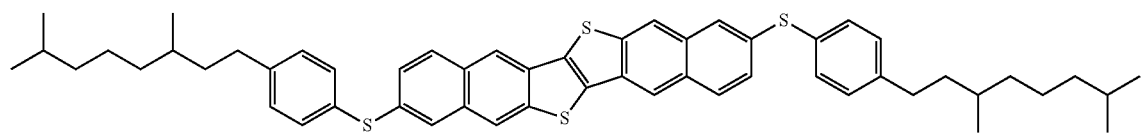
Compound N3
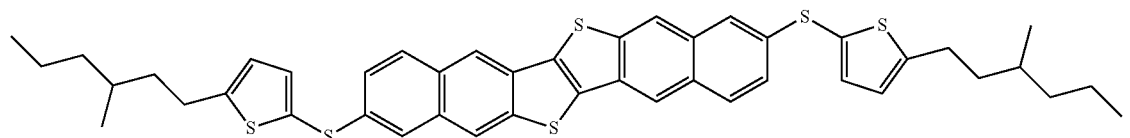
Compound N4
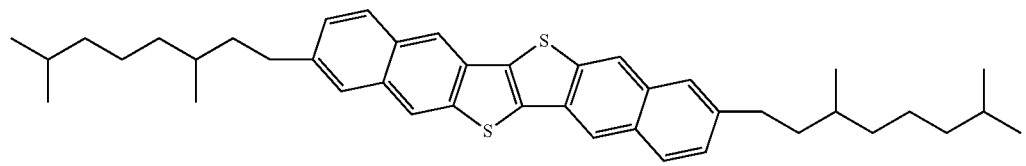
Compound N5
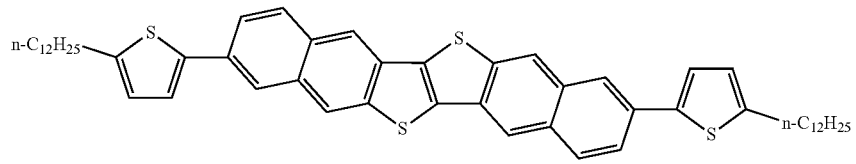
Compound N6
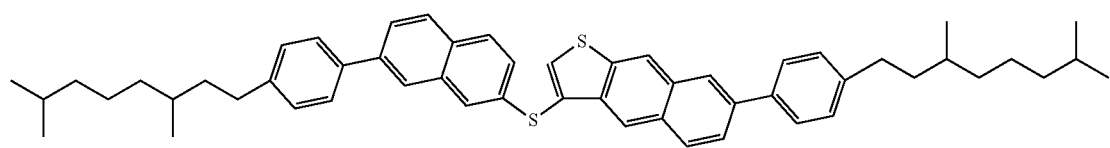

Compound N7
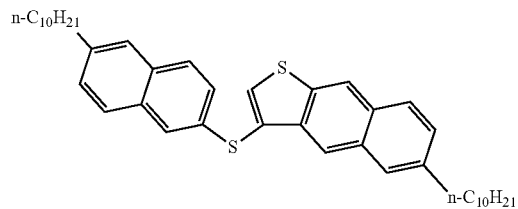
Compound P1
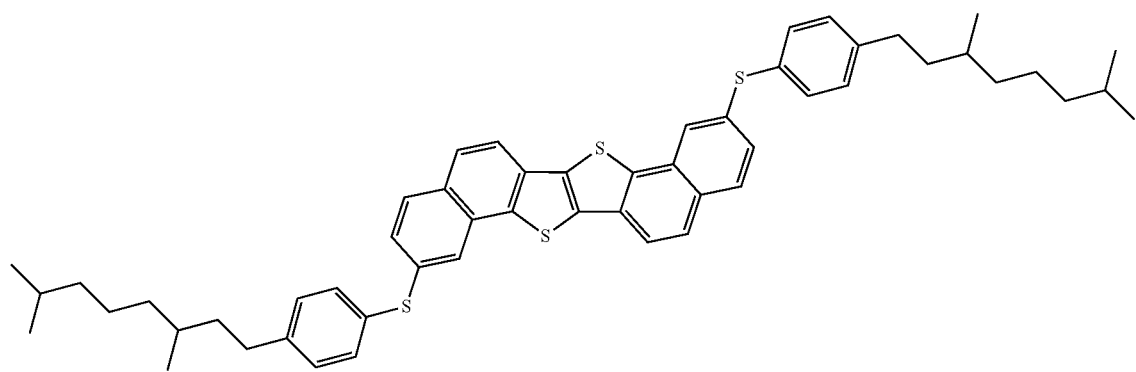
Compound P2
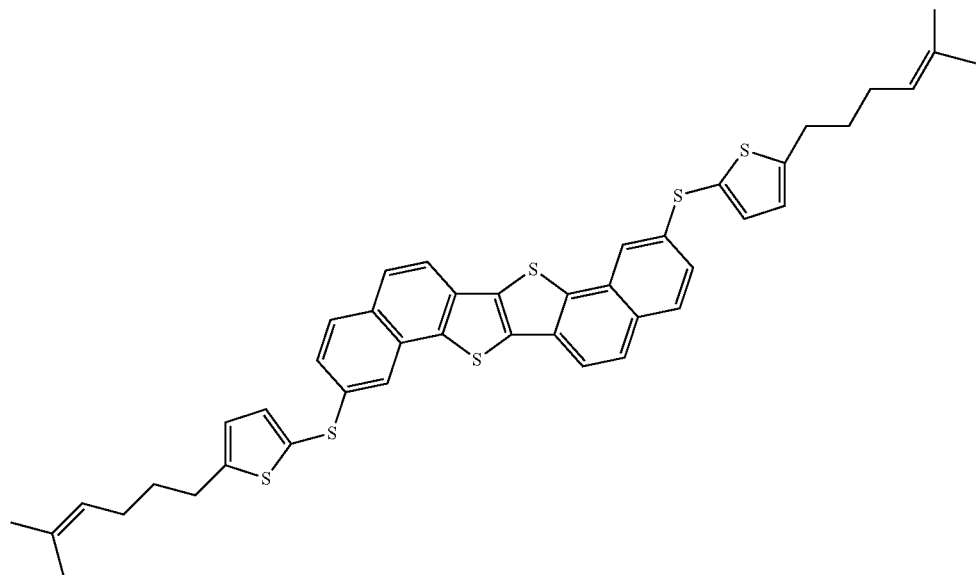

-continued
Compound P3
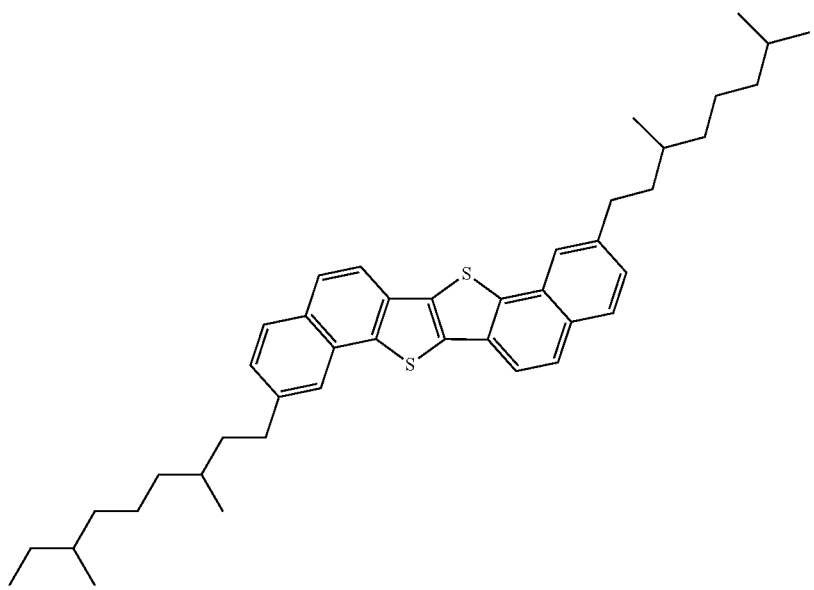
Compound P4
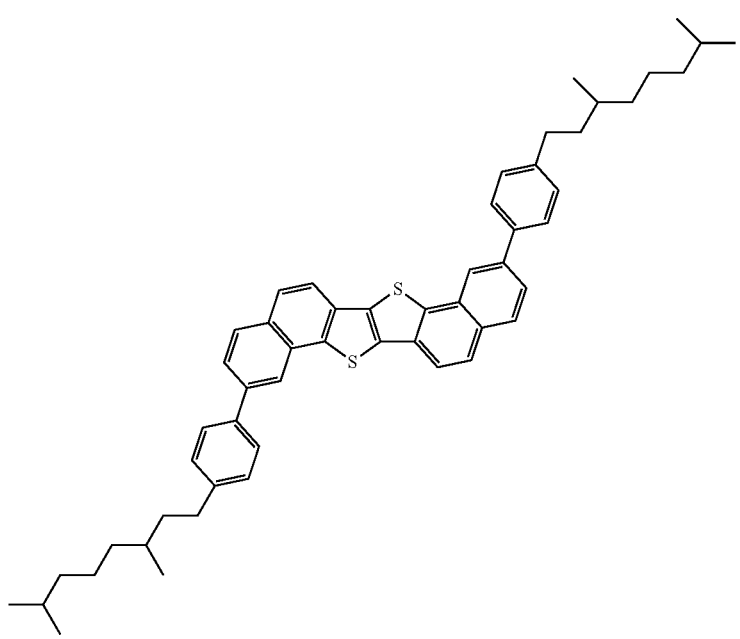
Compound P5
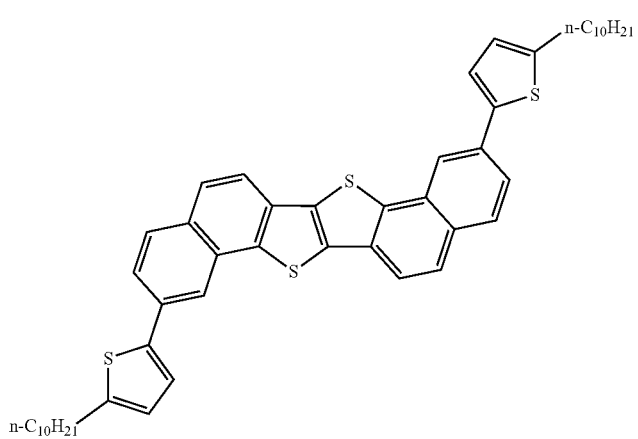

-continued
Compound P6
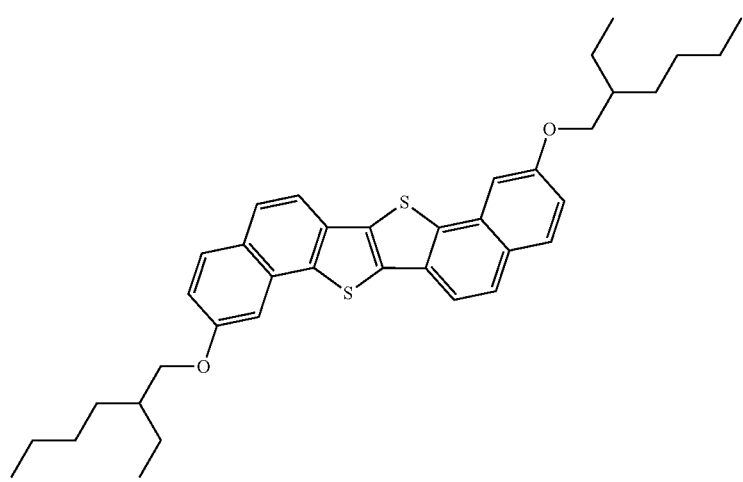
Compound Q1
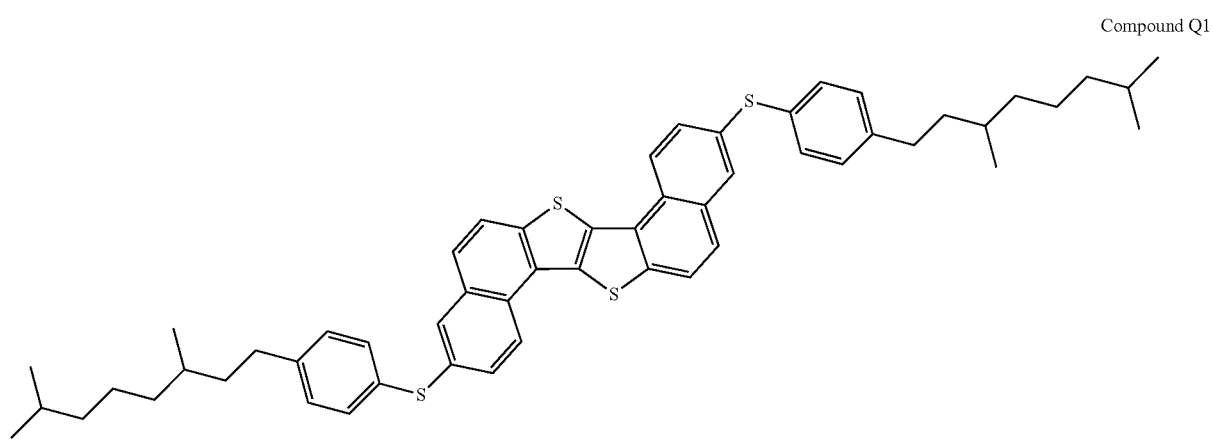
Compound Q2
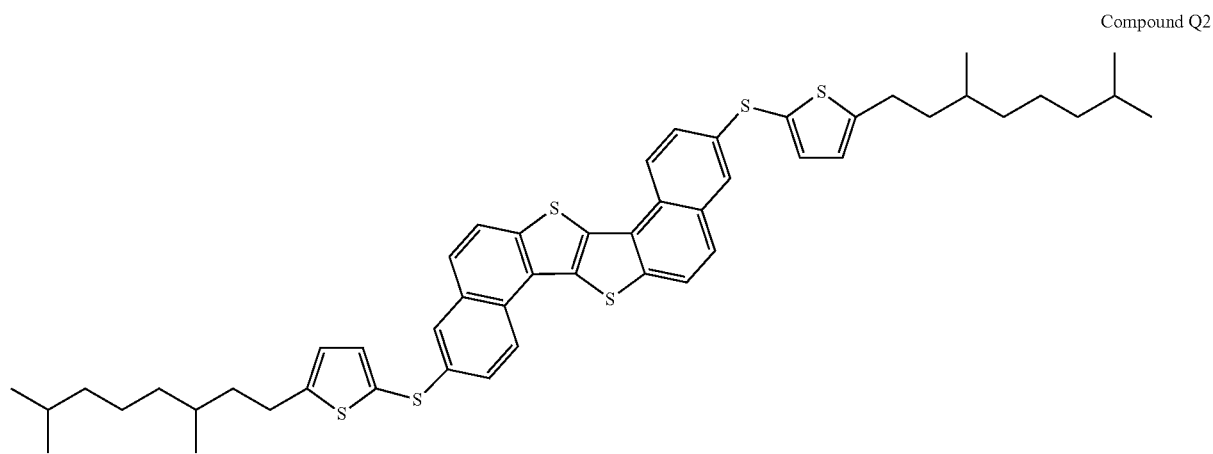

-continued
Compound Q3
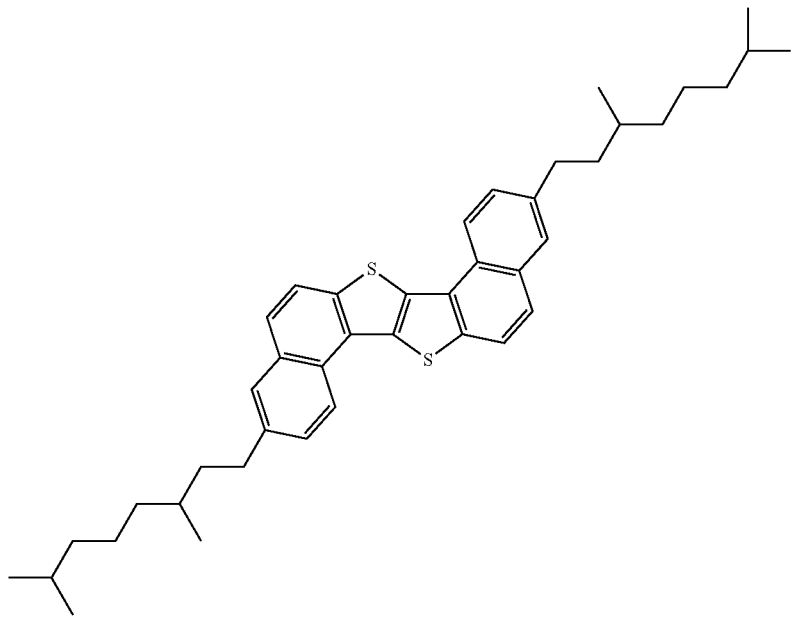
Compound Q4
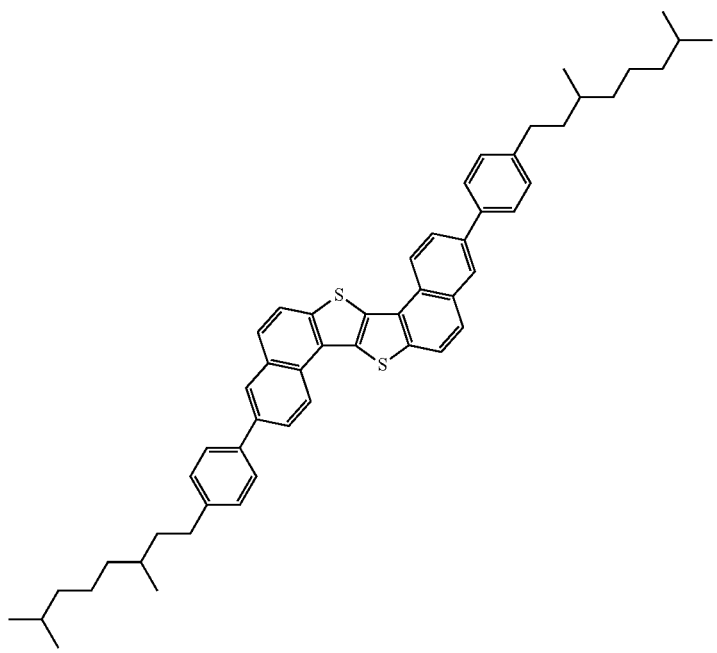

-continued

Compound Q5

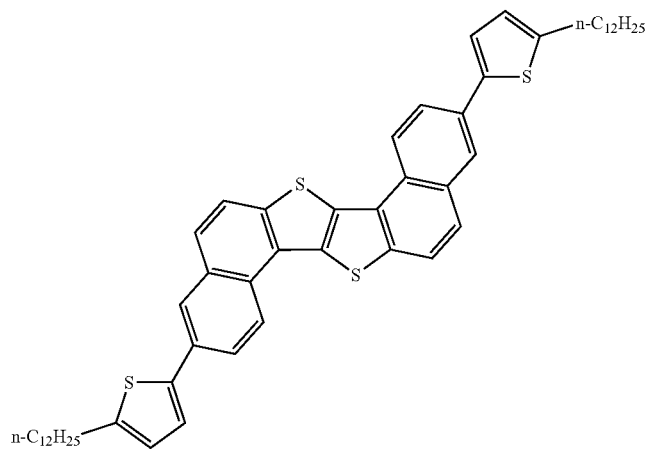

Compound Q6

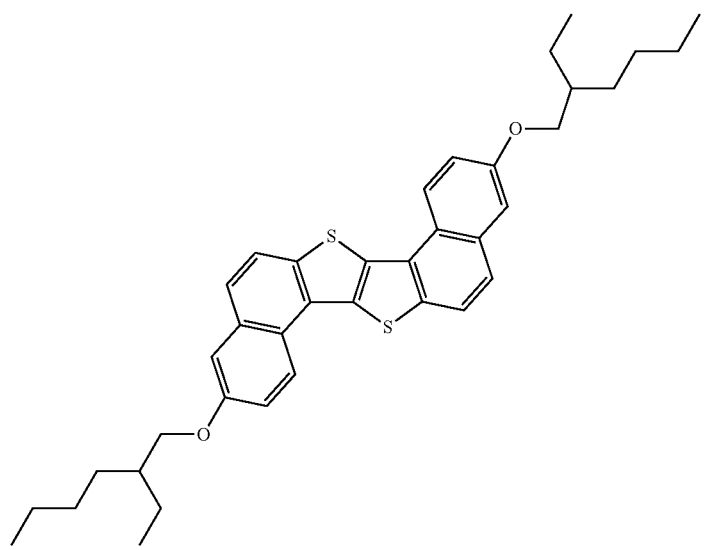

It is preferable that the upper limit of the molecular weight of each of the compound L, the compound M, the compound N, the compound P, and the compound Q is the same as the upper limit of the molecular weight of the compound C represented by Formula (C), because then the solubility of the compound in a solvent can be improved. In contrast, from the viewpoint of the film quality stability of a thin film, the lower limit of the molecular weight is the same as the lower limit of the molecular weight of the compound represented by Formula (D).

Specific examples of each of the compound R represented by Formula (R), the compound S represented by Formula (S), and the compound T represented by Formula (T) will be sequentially shown below.

Compound R1

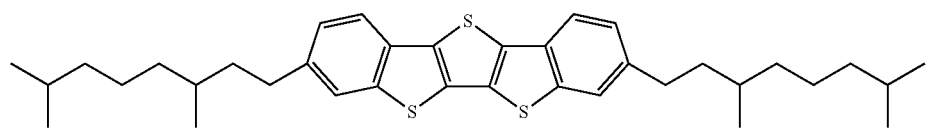

Compound R2

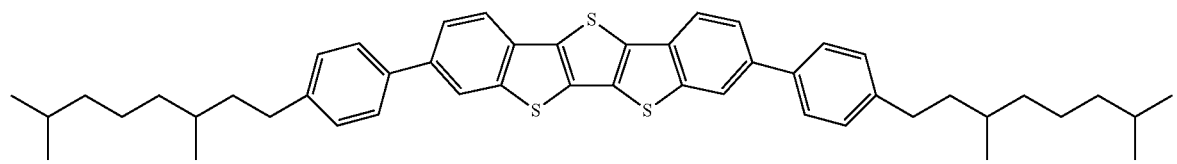

-continued
Compound R3
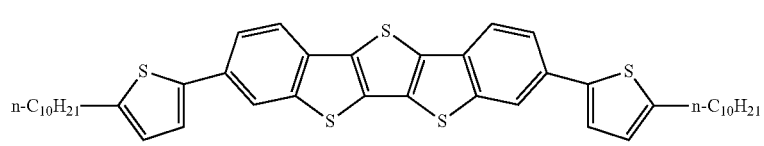
Compound R4
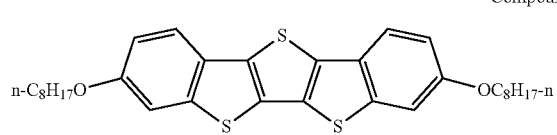
Compound S1
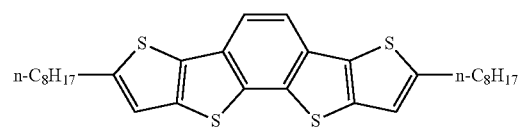
Compound S2
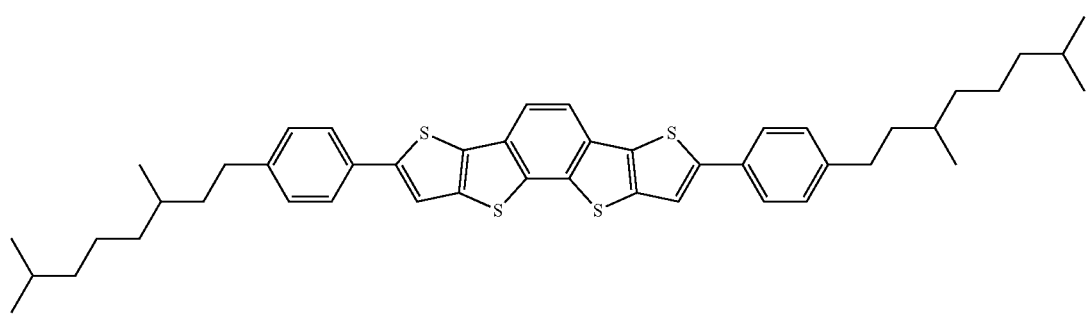
Compound S3
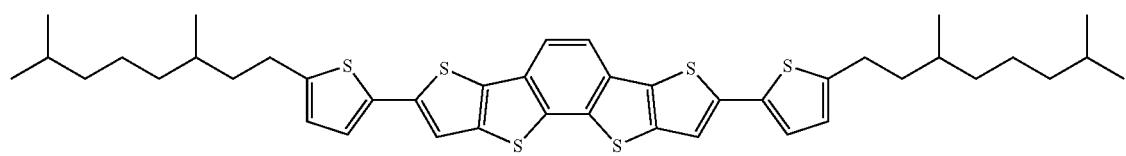
Compound S4
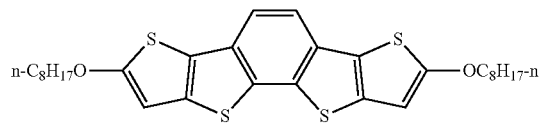
Compound T1
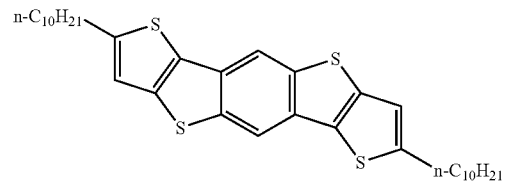
Compound T2
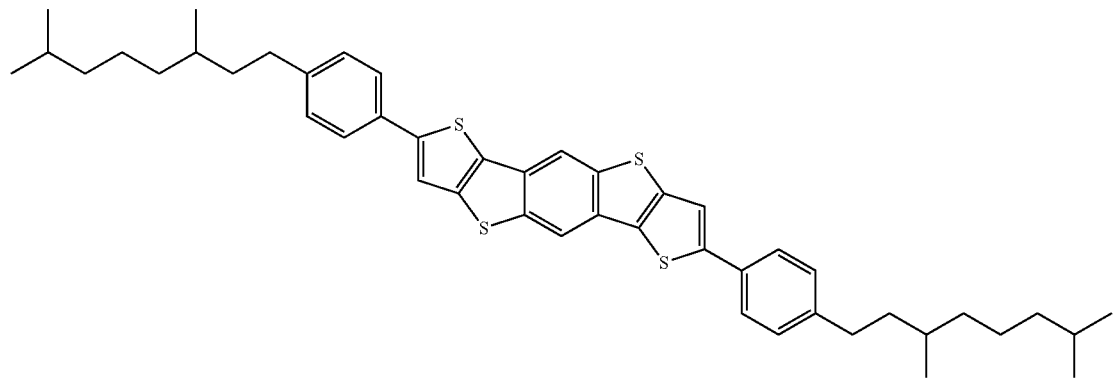

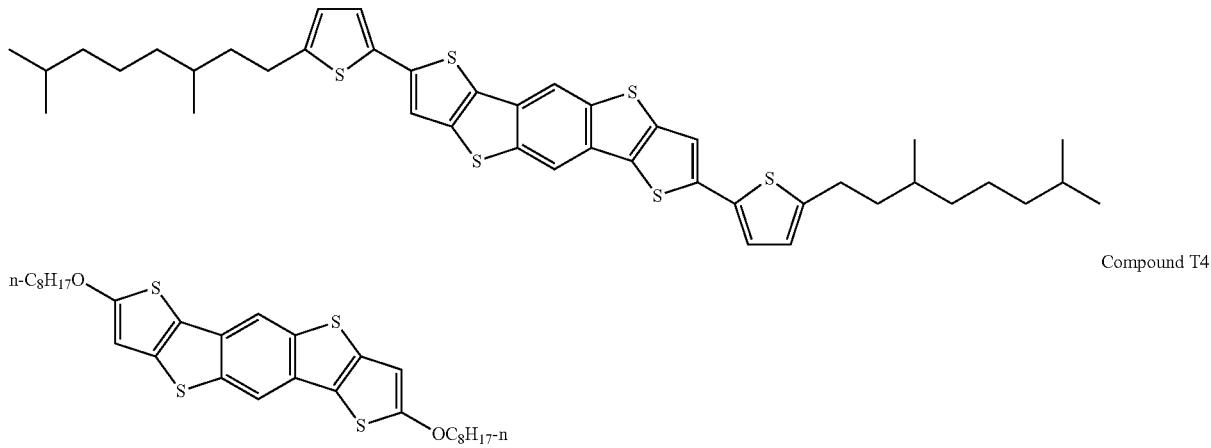

Compound T3

Compound T4

It is preferable that the upper limit of the molecular weight of each of the compound R, the compound S, and the compound T is the same as that the upper limit of the molecular weight of the compound C represented by Formula (C), because then the solubility of the compound in a solvent can be improved. In contrast, from the viewpoint of the film quality stability of a thin film, the lower limit of the molecular weight is the same as the lower limit of the molecular weight of the compound represented by Formula (D).

Examples of the organic polymer used as an organic semiconductor and a derivative thereof include polypyrrole and derivatives thereof, polydiketopyrrole and derivatives thereof, polythiophene and a derivative thereof, isothianaphthene such as polyisothianaphthene, thienylene vinylene such as polythienylene vinylene, poly(p-phenylenevinylene) such as poly(p-phenylenevinylene), polyaniline and a derivative thereof, a polymer such as polyacetylene, polydiacetylene, polyazulene, polypyrene, polycarbazole, polyselenophene, polyfuran, poly(p-phenylene), polyindole, polypyridazine, polytellurophene, polynaphthalene, polyvinylcarbazole, polyphenylene sulfide, or polyvinylene sulfide, a polymer of a condensed polycyclic aromatic compound, and the like.

The polythiophene and a derivative thereof are not particularly limited, and examples thereof include poly-3-hexylthiophene (P3HT) obtained by introducing a hexyl group into polythiophene, polyethylene dioxythiophene, poly(3,4-ethylenedioxythiophene)/polystyrene sulfonic acid (PEDOT/PSS), and the like.

The examples also include oligomers (for example, oligothiophene) having the same repeating unit as these polymers.

Examples of the organic polymer include polymer compounds in which the compounds represented by Formulae (C) to (H), (J) to (N), or (P) to (T) described above have a repeating structure.

Examples of such polymer compounds include π-conjugated polymers in which the compounds represented by Formulae (C) to (H), (J) to (N), or (P) to (T) show a repeating structure through at least one or more arylene groups or heteroarylene groups (thiophene, bithiophene, and the like), and pendant-type polymers in which the compounds represented by Formulae (C) to (H), (J) to (N), or (P) to (T) are bonded to a polymer main chain through a side chain. As the polymer main chain, polyacrylate, polyvinyl, polysiloxane, and the like are preferable, and as the side chain, an alkylene group, a polyethylene oxide group, and the like are preferable. In a case of the pendant-type polymer, the polymer main chain may be formed by the polymerization of at least one of the substituent $R^C$, $R^D$, $R^E$, $R^F$, $R^G$, $R^H$, $R^I$, $R^J$, $R^K$, $R^L$, $R^M$, $R^N$, R, $R^P$, $R^Q$, $R^R$, $R^S$, or $R^T$ having a group derived from a polymerizable group.

The weight-average molecular weight of these organic polymers is preferably equal to or greater than 30,000, more preferably equal to or greater than 50,000, and even more preferably equal to or greater than 100,000. If the weight-average molecular weight is equal to or greater than the lower limit described above, the intermolecular interaction can be strengthened, and high mobility is obtained.

The weight-average molecular weight and the number-average molecular weight of the organic polymer are measured by gel permeation chromatography (GPC).

One kind of the organic semiconductor may be used singly, or two or more kinds thereof may be used in combination. From the viewpoint of crystallinity and mobility, it is preferable to use one kind of the organic semiconductor singly.

The content of the organic semiconductor in the organic semiconductor liquid composition of the present invention is not particularly limited, but is preferably, with respect to the total mass of the organic semiconductor liquid composition, 0.005% to 10% by mass, more preferably 0.01% to 5% by mass, and even more preferably 0.05% to 3% by mass.

<Liquid Crystal Compound>

The organic semiconductor liquid composition of the present invention contains a liquid crystal compound.

As the liquid crystal compound, known liquid crystal compounds can be used without particular limitation, as long as the compounds exhibit liquid crystallinity.

The liquid crystal compound may be a low-molecular weight compound or a polymer. However, the liquid crystal is preferably a low-molecular weight compound, and more preferably a compound having a molecular weight of less than 1,000.

Furthermore, it is preferable that the liquid crystal compound has a polymerizable group.

As the polymerizable group, for example, it is possible to adopt a wide variety of groups such as an ethylenically unsaturated group (that is, a group having an ethylenically unsaturated bond (carbon-carbon double bond) consumed at the time of measuring a bromine index or an iodine index; this group is not an unsaturated group exhibiting aromaticity such as benzene) and a cyclic ether group such as an epoxy group or an oxetane group.

Examples of the ethylenically unsaturated group preferably include an acryloyl group, a methacryloyl group, an acrylamide group, a methacrylamide group, a vinyl group, and a styryl group.

Among these, as the polymerizable group, an ethylenically unsaturated group is preferable, either or both of an acryloyl group and a methacryloyl group are more preferable, and either or both of an acryloyloxy group and a methacryloyloxy group are particularly preferable.

The number of polymerizable groups in one molecule of the liquid crystal compound is not particularly limited, but is preferably 1 to 6, more preferably 1 to 5, even more preferably 1 to 3, and particularly preferably 2.

Examples of the liquid crystal compound preferably include a rod-like liquid crystal compound and a discotic liquid crystal compound, and more preferably include a rod-like liquid crystal compound having a polymerizable group and a discotic liquid crystal compound having a polymerizable group.

As the rod-like liquid crystal compound, azomethines, azoxys, cyanobiphenyls, cyanophenylesters, benzoic acid esters, cyclohexanecarboxylic acid phenyl esters, cyanophenylcyclohexanes, cyano-substituted phenylpyrimidines, alkoxy-substituted phenylpyrimidines, phenyldioxanes, tolanes, and alkenylcyclohexyl benzonitriles are preferably used.

The discotic liquid crystal compound is described in various documents (C. Destrade et at., Mol. Crysr. Liq. Cryst., vol. 71, page 111 (1981); edited by The Chemical Society of Japan, Quarterly Review of Chemistry, No. 22, Chemistry of Liquid Crystal, chapter 5, paragraph 2 of chapter 10 (1994); B. Kohne et al., Angew, Chem. Soc. Chem. Comm., page 1794 (1985); J. Zhang et al., J. Am. Chem. Soc., vol. 116, page 2655 (1994)).

Examples of the rod-like liquid crystal compound having a polymerizable group preferably include compounds represented by the following Formula LC.

Q$^1$-L$^1$-Cy$^1$-(CH=CH)$_{nL}$—CO—NR$^{1L}$-Cy$^2$-L$^2$-Q$^2$:  Formula LC

In Formula LC, Q$^1$ and Q$^2$ each independently represent a polymerizable group. The polymerization reaction of the polymerizable group is preferably addition polymerization (including ring-opening polymerization) or a condensation polymerization. In other words, the polymerizable group is preferably a functional group which can be subjected to an addition polymerization reaction or a condensation polymerization reaction.

Examples of the polymerizable group will be shown below.

—CH=CH$_2$  (Q-1)

—CH=CH—CH$_3$  (Q-2)

—CH=CH—C$_2$H$_5$  (Q-3)

—CH=CH—n-C$_3$H$_7$  (Q-4)

-continued

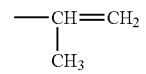
(Q-5)

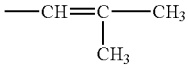
(Q-6)

—C≡CH  (Q-7)

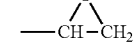
(Q-8)

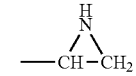
(Q-9)

—SH  (Q-10)

—CHO  (Q-11)

—OH  (Q-12)

—CO$_2$H  (Q-13)

—N=C=O  (Q-14)

—NH$_2$  (Q-15)

—SO$_3$H  (Q-16)

—N=C=S  (Q-17)

The polymerizable group (Q$^1$ and Q$^2$) is preferably an unsaturated polymerizable group (Q-1 to Q-7), an epoxy group (Q-8), or an aziridinyl group (Q-9), more preferably an unsaturated polymerizable group, and even more preferably an ethylenically unsaturated group (Q-1 to Q-6).

In Formula LC, L$^1$ and L$^2$ each independently represent a divalent linking group.

L$^1$ and L$^2$ preferably each independently represent —O—, —S—, —CO—, —NR$^{2L}$—, a divalent chain-like group, a divalent cyclic group, and a divalent linking group selected from the group which is a combination of the above groups. R$^{2L}$ represents an alkyl group having 1 to 7 carbon atoms or a hydrogen atom.

Examples of the divalent linking group obtained by combining the above groups will be shown below. The left side of the linking group is bonded to Q (Q$^1$ or Q$^2$), and the right side thereof is bonded to Cy (Cy$^1$ or Cy$^2$).

L-1:  —CO—O-divalent chain-like group-O—

L-2:  —CO—O-divalent chain-like group-O-divalent cyclic group-CO—O—

L-3:  —CO—O-divalent chain-like group-O-divalent cyclic group-O—CO—

L-4:  —CO—O-divalent chain-like group-O-divalent cyclic group-divalent chain-like group- L-5:  —COO-divalent chain-like group-O-divalent cyclic group- L-6:  —CO—O-divalent chain-like group-O-divalent cyclic group-divalent chain-like group-CO—O—

L-7:  —CO—O-divalent chain-like group-O-divalent cyclic group-O—CO-divalent chain-like group- The divalent chain-like group is an alkylene group, a substituted alkylene group, an alkenylene group, a substituted alkenylene group, an alkynylene group, or a substituted alkynylene group. The divalent chain-like group is preferably an alkylene group, a substituted alkylene group, an alkenylene group, or a substituted alkenylene group, and more preferably an alkylene group or an alkenylene group. The alkylene group may be branched.

The number of carbon atoms in the alkylene group is preferably 1 to 12, more preferably 2 to 10, and particularly preferably 3 to 8. The alkylene portion of the substituted alkylene group is the same as the aforementioned alkylene group. Examples of the substituent of the substituted alkylene group include a halogen atom. The alkenylene group may be branched. The number of carbon atoms in the alkenylene group is preferably 2 to 12, more preferably 2 to 8, and particularly preferably 2 to 4. The alkenylene portion of the substituted alkenylene group is the same as the aforementioned alkenylene group. Examples of the substituent of the substituted alkenylene group include a halogen atom. The alkynylene group may be branched. The number of carbon atoms in the alkynylene group is preferably 2 to 12, more preferably 2 to 8, and particularly preferably 2 to 4. The alkynylene portion of the substituted alkynylene group is the same as the aforementioned alkynylene group. Examples of the substituent of the substituted alkynylene group include a halogen atom.

The definition and examples of the divalent cyclic group are the same as the definition and examples of $Cy^1$ and $Cy^2$ which will be described later.

$R^{2L}$ is preferably an alkyl group having 1 to 4 carbon atoms or a hydrogen atom, more preferably an ethyl group, a methyl group, or a hydrogen atom, and particularly preferably a hydrogen atom.

$L^2$ is preferably —O—CO—(CH=CH)$_m$-Cy$^3$-L$^3$- or —(CH=CH)$_m$—CO—O-Cy$^3$-L$^3$-. m is 0 or 1, Cy$^3$ is a divalent cyclic group, and $L^3$ is a divalent linking group.

m is preferably 0. The definition and examples of the divalent cyclic group are the same as the definition and examples of $Cy^1$ and $Cy^2$ which will be described later. $L^3$ is preferably —O—, —S—, —CO—, —NR$^{2L}$—, a divalent chain-like group, and a divalent linking group selected from the group which is a combination of the above groups. $L^3$ is particularly preferably —O-divalent chain-like group —O—CO—.

The compound represented by Formula LC particularly preferably contains three divalent cyclic groups ($Cy^1$, $Cy^2$, and $Cy^3$) in total.

In Formula LC, $Cy^1$ and $Cy^2$ each independently represent a divalent cyclic group.

The ring contained in the cyclic group is preferably a 5-, 6-, or 7-membered ring, more preferably a 5- or 6-membered ring, and particularly preferably a 6-membered ring. The ring contained in the cyclic group may be a condensed ring. Here, a monocyclic ring is more preferred than a condensed ring. The ring contained in the cyclic group may be any of an aromatic ring, an aliphatic ring, and a heterocyclic ring. Examples of the aromatic ring include a benzene ring and a naphthalene ring. Examples of the aliphatic ring include a cyclohexane ring. Examples of the heterocyclic ring include a pyridine ring and a pyrimidine ring.

As the cyclic group having a benzene ring, a 1,4-phenylene group is preferable. As the cyclic group having a naphthalene ring, a naphthalene-1,5-diyl group or a naphthalene-2,6-diyl group is preferable. As the cyclic group having a pyridine ring, a pyridine-2,5-diyl group is preferable. As the cyclic group having a pyrimidine ring, a pyrimidine-2,5-diyl group is preferable.

The cyclic group is particularly preferably a 1,4-phenylene group or a 1,4-cyclohexylene group.

The cyclic group may have a substituent. Examples of the substituent include a halogen atom, cyano, nitro, an alkyl group having 1 to 5 carbon atoms, a halogen atom-substituted alkyl group having 1 to 5 carbon atoms, an alkoxy group having 1 to 5 carbon atoms, an alkylthio group having 1 to 5 carbon atoms, an acyl group having 1 to 5 carbon atoms, an acyloxy group having 2 to 6 carbon atoms, an alkoxycarbonyl group having 2 to 6 carbon atoms, carbamoyl, an alkyl-substituted carbamoyl group having 2 to 6 carbon atoms, and an amide group having 2 to 6 carbon atoms.

In Formula LC, $R^{1L}$ represents an alkyl group having 1 to 7 carbon atoms or a hydrogen atom. $R^{1L}$ is preferably an alkyl group having 1 to 4 carbon atoms or a halogen atom, more preferably an ethyl group, a methyl group, or a hydrogen atom, and particularly preferably a hydrogen atom.

In Formula LC, n represents 0 or 1, and preferably represents 0.

As the polymerizable rod-like liquid crystal compound, for example, it is possible to use the compounds described in Makromol. Chem., vol. 190, p. 2255 (1989), Advanced Materials, vol. 5, p. 107 (1993), U.S. Pat. No. 4,683,327A, U.S. Pat. No. 5,622,648A, U.S. Pat. No. 5,770,107A, WO95/22586A, WO95/24455A, WO97/00600A, WO98/23580A, WO98/52905A, JP1989-272551A (JP-H01-272551A), JP1994-16616A (JP-H06-16616A), JP1995-110469A (JP-H07-110469A), JP1999-80081A (JP-H11-80081A), and JP2001-328973A.

As the discotic liquid crystal compound having a polymerizable group, a compound represented by the following Formula (DI) is preferable.

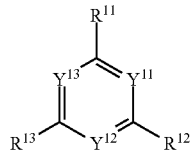

Formula (DI)

In Formula (DI), $Y^{11}$, $Y^{12}$, and $Y^{13}$ each independently represent a methine group or a nitrogen atom.

In a case where $Y^{11}$, $Y^{12}$, and $Y^{13}$ each represent a methine group, a hydrogen atom of the methine group may be substituted with a substituent. Preferred examples of the substituent that the methine group may have include an alkyl group, an alkoxy group, an aryloxy group, an acyl group, an alkoxycarbonyl group, an acyloxy group, an acylamino group, an alkoxycarbonylamino group, an alkylthio group, an arylthio group, a halogen atom, and a cyano group. Among these substituents, an alkyl group, an alkoxy group, an alkoxycarbonyl group, an acyloxy group, a halogen atom, and a cyano group are preferable, and an alkyl group having 1 to 12 carbon atoms, an alkoxy group having 1 to 12 carbon atoms, an alkoxycarbonyl group having 2 to 12 carbon atoms, an acyloxy group having 2 to 12 carbon atoms, a halogen atom, and a cyano group are more preferable.

$Y^{11}$, $Y^{12}$, and $Y^{13}$ preferably all represent a methine group, and the methine group is preferably an unsubstituted.

$R^{11}$, $R^{12}$, and $R^{13}$ each independently represent a group represented by the following Formula (DI-A), (DI-B), or (DI-C). In a case where the reduction of wavelength dispersibility is intended, a group represented by Formula (DI-A) or (DI-C) is preferable, and a group represented by Formula (DI-A) is more preferable. $R^{11}$, $R^{12}$, and $R^{13}$ preferably satisfy the relationship of $R^{11}$=$R^{12}$=$R^{13}$.

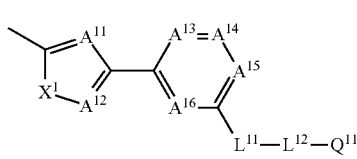

Formula (DI-A)

In Formula (DI-A), $A^{11}$, $A^{12}$, $A^{13}$, $A^{14}$, $A^{15}$, and $A^{16}$ each independently represent a methine group or a nitrogen atom.

It is preferable that at least one of $A^{11}$ or $A^{12}$ represents a nitrogen atom. It is more preferable that $A^{11}$ and $A^{12}$ both represent a nitrogen atom.

It is preferable that at least three out of $A^{13}$, $A^{14}$, $A^{15}$, and $A^{16}$ represent a methine group. It is more preferable that $A^{13}$, $A^{14}$, $A^{15}$, and $A^{16}$ all represent a methine group. The methine group is preferably unsubstituted.

In a case where $A^{11}$, $A^{12}$, $A^{13}$, $A^{14}$, $A^{15}$, or $A^{16}$ represents a methine group, examples of the substituent include a halogen atom (a fluorine atom, a chlorine atom, a bromine atom, or an iodine atom), a cyano group, a nitro group, an alkyl group having 1 to 16 carbon atoms, an alkenyl group having 2 to 16 carbon atoms, an alkynyl group having 2 to 16 carbon atoms, a halogen-substituted alkyl group having 1 to 16 carbon atoms, an alkoxy group having 1 to 16 carbon atoms, an acyl group having 2 to 16 carbon atoms, an alkylthio group having 1 to 16 carbon atoms, an acyloxy group having 2 to 16 carbon atoms, an alkoxycarbonyl group having 2 to 16 carbon atoms, a carbamoyl group, an alkyl-substituted carbamoyl group having 2 to 16 carbon atoms, and an acylamino group having 2 to 16 carbon atoms. Among these, a halogen atom, a cyano group, an alkyl group having 1 to 6 carbon atoms, a halogen-substituted alkyl group having 1 to 6 carbon atoms, a halogen atom, an alkyl group having 1 to 4 carbon atoms, and a halogen-substituted alkyl group having 1 to 4 carbon atoms are more preferable, and a halogen atom, an alkyl group having 1 to 3 carbon atoms, and a trifluoromethyl group are more preferable.

$X^1$ represents an oxygen atom, a sulfur atom, a methylene group, or an imino group, and preferably represents an oxygen atom.

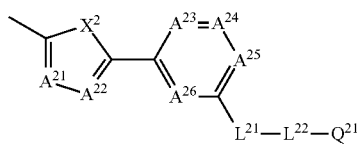

Formula (DI-B)

In Formula (DI-B), $A^{21}$, $A^{22}$, $A^{23}$, $A^{24}$, $A^{25}$, and $A^{26}$ each independently represent a methine group or a nitrogen atom.

It is preferable that at least one of $A^{21}$ or $A^{22}$ represents a nitrogen atom. It is more preferable that $A^{21}$ and $A^{22}$ both represent a nitrogen atom.

It is preferable that at least three out of $A^{23}$, $A^{24}$, $A^{25}$, and $A^{26}$ represent a methine group. It is more preferable that $A^{23}$, $A^{24}$, $A^{25}$, and $A^{26}$ all represent a methine group.

In a case where $A^{21}$, $A^{22}$, $A^{23}$, $A^{24}$, $A^{25}$, or $A^{26}$ represents a methine group, examples of the substituent are the same as the examples of the substituent adopted in a case where $A^1$, $A^{12}$, $A^{13}$, $A^{14}$, $A^{15}$, or $A^{16}$ represents a methine group, and a preferred aspect thereof is also the same.

$X^2$ represents an oxygen atom, a sulfur atom, a methylene group, or an imino group, and preferably represents an oxygen atom.

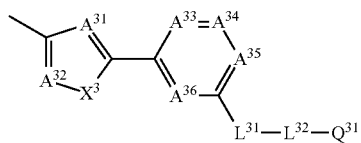

Formula (DI-C)

In Formula (DI-C), $A^{31}$, $A^{32}$, $A^{33}$, $A^{34}$, $A^{35}$, and $A^{36}$ each independently represent a methine group or a nitrogen atom.

It is preferable that at least one of $A^{31}$ or $A^{32}$ represents a nitrogen atom. It is more preferable that $A^{31}$ and $A^{32}$ both represent a nitrogen atom.

It is preferable that at least three out of $A^{33}$, $A^{34}$, $A^{35}$, and $A^{36}$ represent a methine group. It is more preferable that $A^{33}$, $A^{34}$, $A^{35}$, and $A^{36}$ all represent a methine group.

In a case where $A^{31}$, $A^{32}$, $A^{33}$, $A^{34}$, $A^{35}$, or $A^{36}$ represents a methine group, examples of the substituent are the same as the examples of the substituent adopted in a case where $A^{11}$, $A^{12}$, $A^{13}$, $A^{14}$, $A^5$, or $A^{16}$ represents a methine group, and a preferred aspect thereof is also the same.

$X^3$ represents an oxygen atom, a sulfur atom, a methylene group, or an imino group, and preferably represents an oxygen atom.

$L^{11}$ in Formula (DI-A), $L^{21}$ in Formula (DI-B), and $L^{31}$ in Formula (DI-C) each independently represent —O—, —O—CO—, —CO—O—, —O—CO—O—, —S—, —NH—, —SO$_2$—, —CH$_2$—, —CH=CH—, or —C≡C—, preferably each independently represent —O—, —O—CO—, —CO—O—, —O—CO—O—, —CH$_2$—, —CH=CH—, or —C≡C— and more preferably each independently represent —O—, —O—CO—, —CO—O—, —O—CO—O—, or —CH$_2$—. In a case where the above group is a group containing a hydrogen atom, the hydrogen atom may be substituted with a substituent. Preferred examples of the substituent include a halogen atom, a cyano group, a nitro group, an alkyl group having 1 to 6 carbon atoms, a halogen-substituted alkyl group having 1 to 6 carbon atoms, an alkoxy group having 1 to 6 carbon atoms, an acyl group having 2 to 6 carbon atoms, an alkylthio group having 1 to 6 carbon atoms, an acyloxy group having 2 to 6 carbon atoms, an alkoxycarbonyl group having 2 to 6 carbon atoms, a carbamoyl group, an alkyl-substituted carbamoyl group having 2 to 6 carbon atoms, and an acylamino group having 2 to 6 carbon atoms. Among these, a halogen atom and an alkyl group having 1 to 6 carbon atoms are more preferable.

$L^{12}$ in Formula (DI-A), $L^{22}$ in Formula (DI-B), and $L^{32}$ in Formula (DI-C) each independently represent —O—, —S—, —C(=O)—, —SO$_2$—, —NH—, —CH$_2$—, —CH=CH—, —C=C—, and a divalent linking group selected from the group which is a combination of the above groups. Herein, the hydrogen atom of —NH—, —CH$_2$—, and —CH=CH— may be substituted with a substituent. Examples of the substituent preferably include a halogen atom, a cyano group, a nitro group, an alkyl group having 1 to 6 carbon atoms, a halogen-substituted alkyl group having 1 to 6 carbon atoms, an alkoxy group having 1 to 6 carbon atoms, an acyl group having 2 to 6 carbon atoms, an alkylthio group having 1 to 6 carbon atoms, an acyloxy group having 2 to 6 carbon atoms, an alkoxycarbonyl group having 2 to 6 carbon atoms, a carbamoyl group, an alkyl-substituted carbamoyl group having 2 to 6 carbon atoms, and an acylamino group having 2 to 6 carbon atoms, and more preferably include a halogen atom and an alkyl group having 1 to 6 carbon atoms.

$L^{12}$, $L^{22}$, and $L^{32}$ preferably each independently represent —O—, —C(=O)—, —CH$_2$—, —CH=CH—, —C≡C—, and a group selected from the group which is a combination of the above groups.

The number of carbon atoms that $L^{12}$, $L^{22}$, and $L^{32}$ each independently have is preferably 1 to 20, and more preferably 2 to 14. $L^{12}$, $L^{22}$, and $L^{32}$ preferably each independently represent a group having 1 to 16 —CH$_2$— groups, and more preferably each independently represent a group having 2 to 12 —CH$_2$— groups.

$Q^{11}$ in Formula (DI-A), $Q^{21}$ in Formula (DI-B), and $Q^{31}$ in Formula (DI-C) each independently represent a polymerizable group or a hydrogen atom.

$Q^{11}$, $Q^{21}$, and $Q^{31}$ preferably each independently represent a polymerizable group. The polymerization reaction is preferably addition polymerization (including ring-opening polymerization) or condensation polymerization. That is, the polymerizable group is preferably a functional group which can be subjected to an addition polymerization reaction or a condensation polymerization reaction. Examples of the polymerizable group will be shown below.

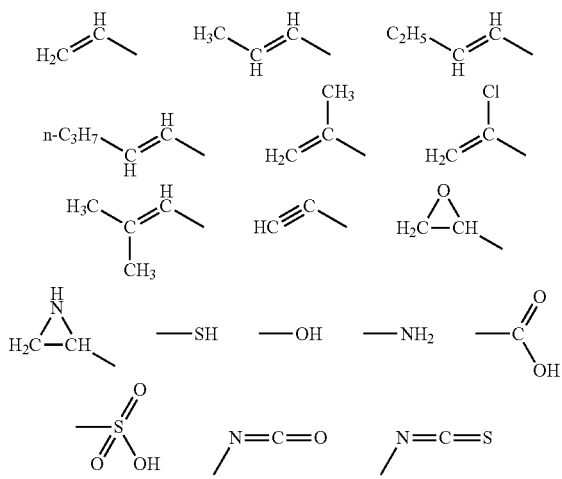

The polymerizable group is preferably a functional group which can be subjected to an addition polymerization reaction, more preferably an ethylenically unsaturated group, and even more preferably a group represented by any of the following Formulae (M-1) to (M-6).

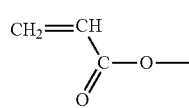
(M-1)

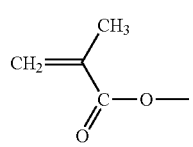
(M-2)

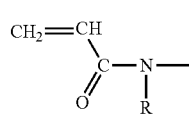
(M-3)

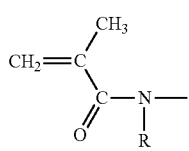
(M-4)

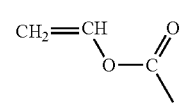
(M-5)

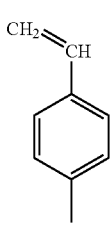
(M-6)

In Formulae (M-3) and (M-4), R represents a hydrogen atom or an alkyl group. R is preferably a hydrogen atom or a methyl group.

Among the above, as the polymerizable group, the group represented by Formula (M-1) or (M-2) is preferable, and the group represented by Formula (M-1) is more preferable.

Among the compounds described in paragraphs "0038" to "0069" of JP2009-97002A (1,3,5-substituted benzene-type discotic liquid crystal compounds), the compounds in which X represents a group having a polymerizable group can be exemplified as the discotic liquid crystal compound having a polymerizable group. Furthermore, among the compounds described in paragraphs "0062" to "0067" of JP2007-108732A, the compounds having a polymerizable group as a substituent can be suitably used in the present invention as the discotic liquid crystal compound having a polymerizable group.

One kind of the liquid crystal compound may be used singly, or two or more kinds thereof may be used in combination.

The content of the liquid crystal compound in the organic semiconductor liquid composition of the present invention is not particularly limited, but is, with respect to the total mass of the organic semiconductor liquid composition, preferably 0.1% to 20% by mass, more preferably 0.5% to 15% by mass, and even more preferably 1% to 10% by mass. In a case where the content of the liquid crystal compound is within the above range, it is possible to obtain an organic semiconductor film having better mobility.

The content of the liquid crystal compound in the organic semiconductor liquid composition of the present invention is, with respect to 100 parts by mass of the content of the organic semiconductor, preferably 50 to 5,000 parts by mass, more preferably 100 to 3,000 parts by mass, even more preferably 200 to 2,500 parts by mass, and particularly preferably 500 to 2,000 parts by mass. In a case where the content of the liquid crystal compound is within the above range, it is possible to obtain an organic semiconductor film having better mobility.

<Organic Insulating Polymer>

The organic semiconductor liquid composition of the present invention contains an organic insulating polymer.

The type of the organic insulating polymer is not particularly limited, and known organic insulating polymers can be used.

The organic insulating polymer refers to a general organic polymer which is neither a conductive polymer nor the aforementioned organic semiconductor.

Examples of the organic insulating polymer include polyvinyl carboxylate, polyvinyl acetal, polystyrene, polycarbonate, polyarylate, polyester, polyamide, polyimide, polyurethane, polysiloxane, polysulfone, polymethyl methacrylate, polymethyl acrylate, cellulose, polyethylene, polypropylene, a copolymer of these, rubber, and a thermoplastic elastomer.

Among these, as the organic insulating polymer, polyvinyl carboxylate or a polyvinyl acetal is preferable, and a polyvinyl carboxylate or polyvinyl butyral is more preferable.

The organic insulating polymer preferably includes a resin having a constitutional unit represented by the following Formula 1a and/or a constitutional unit represented by the following Formula 1b, and more preferably includes a resin having a constitutional unit represented by the following Formula 1a or a constitutional unit represented by the following Formula 1b.

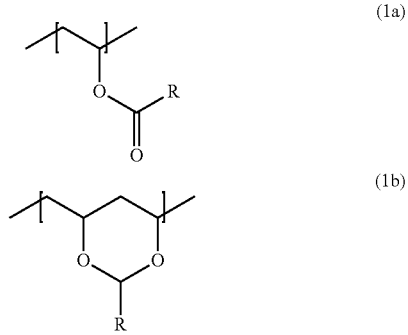

In the formulae, R's each independently represent a linear or branched alkyl group having 1 to 20 carbon atoms.

R in Formula 1a is preferably a linear or branched alkyl group having 1 to 17 carbon atoms, more preferably a linear alkyl group having 1 to 17 carbon atoms, and even more preferably a linear alkyl group having 5 to 17 carbon atoms.

R in Formula 1b is preferably a linear or branched alkyl group having 1 to 8 carbon atoms, more preferably a linear or branched alkyl group having 1 to 6 carbon atoms, even more preferably a linear or branched alkyl group having 2 to 4 carbon atoms, and particularly preferably a propyl group.

Examples of the resin having a constitutional unit represented by Formula 1a include polyvinyl carboxylate.

The polyvinyl carboxylate is preferably a homopolymer or copolymer of vinyl carboxylate having 4 to 23 carbon atoms, more preferably a homopolymer or copolymer of vinyl carboxylate selected from the group consisting of vinyl acetate, vinyl propionate, vinyl butyrate, vinyl valerate, vinyl caproate, vinyl pentanoate, vinyl octanoate, vinyl nonanoate, vinyl decanoate, vinyl laurate, vinyl myristate, vinyl palmitate, and vinyl stearate, even more preferably a homopolymer or copolymer of vinyl carboxylate selected from the group consisting of vinyl acetate, vinyl octanoate, vinyl decanoate, vinyl laurate, vinyl myristate, vinyl palmitate, and vinyl stearate, and particularly preferably a homopolymer or copolymer of vinyl carboxylate selected from the group consisting of vinyl octanoate, vinyl decanoate, vinyl laurate, vinyl myristate, vinyl palmitate, and vinyl stearate.

Examples of the resin having a constitutional unit represented by Formula 1b include polyvinyl acetal.

The polyvinyl acetal has a constitutional unit represented by the following Formula 1c in addition to the constitutional unit represented by Formula 1b, and may further have a constitutional unit represented by the following Formula 1d.

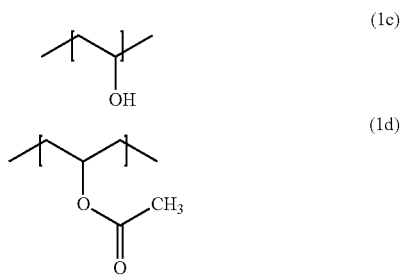

The polyvinyl acetal is preferably polyvinyl butyral.

In the polyvinyl butyral, a hydroxyl group content which is the content of the constitutional unit represented by Formula 1c with respect to the total amount of the polyvinyl butyral is preferably equal to or less than 20% by mass, more preferably equal to or less than 18% by mass, even more preferably equal to or less than 15% by mass, and particularly preferably 6% to 15% by mass.

The weight-average molecular weight of the organic insulating polymer is not particularly limited, but is preferably 1,000 to 2,000,000, more preferably 3,000 to 1,000,000, even more preferably 5,000 to 600,000.

In a case where the solvent which will be described later is used, it is preferable that the solubility of a binder polymer in the solvent used is higher than the solubility of a specific compound. If the above aspect is adopted, the mobility and heat stability of the obtained organic semiconductor are further improved.

One kind of the organic insulating polymer may be used singly, or two or more kinds thereof may be used in combination.

The content of the organic insulating polymer in the organic semiconductor liquid composition of the present invention is, with respect to 100 parts by mass of the content of the organic semiconductor, preferably 1 to 200 parts by mass, more preferably 10 to 150 parts by mass, and even more preferably 20 to 120 parts by mass. In a case where the content of the organic insulating polymer is within the above range, the mobility and heat stability of the obtained organic semiconductor layer are further improved.

<Solvent>

From the viewpoint of the coating properties and the formation of a layer, the organic semiconductor liquid composition of the present invention preferably contains a solvent.

As the solvent, known solvents can be used.

Specific examples of the solvent include a hydrocarbon-based solvent such as hexane, octane, decane, toluene, xylene, mesitylene, ethylbenzene, decalin, or 1-methylnaphthalene, a ketone-based solvent such as acetone, methyl ethyl ketone, methyl isobutyl ketone, or cyclohexanone, a halogenated hydrocarbon-based solvent such as dichloromethane, chloroform, tetrachloromethane, dichloroethane, trichloroethane, tetrachloroethane, chlorobenzene, dichlorobenzene, or chlorotoluene, an ester-based solvent such as ethyl acetate, butyl acetate, or amyl acetate, an alcohol-based solvent such as methanol, propanol, butanol, pentanol, hexanol, cyclohexanol, methyl cellosolve, ethyl cellosolve, or ethylene glycol, an ether-based solvent such as dibutyl ether, tetrahydrofuran, dioxane, or anisole, an amide-based solvent such as N,N-dimethylformamide or N,N-dimethylacetamide, an imide-based solvent such as 1-methyl-2-pyrrolidone or 1-methyl-2-imidazolidinone, a sulfoxide-based solvent such as dimethyl sulfoxide, and a nitrile-based solvent such as acetonitrile.

One kind of solvent may be used singly, or plural kinds thereof may be used in combination.

Among the solvents, an aliphatic hydrocarbon-based solvent, an aromatic hydrocarbon-based solvent, an aromatic heterocyclic solvent, a halogenated hydrocarbon-based solvent, and/or an ether-based solvent are preferable, an aromatic hydrocarbon-based solvent, a halogenated aromatic hydrocarbon-based solvent, and/or an ether-based solvent are more preferable, and toluene, xylene, mesitylene, tetralin, dichlorobenzene, or anisole is even more preferable.

From the viewpoint of film forming properties, the boiling point of the solvent is preferably equal to or higher than 100° C. The boiling point of the solvent is more preferably 100° C. to 300° C., even more preferably 105° C. to 250° C., and particularly preferably 110° C. to 225° C.

It is preferable that the boiling point of the solvent contained in the composition in the largest amount is preferably equal to or higher than 100° C. It is more preferable that the boiling point of all the solvents is equal to or higher than 100° C.

The content of the solvent in the organic semiconductor liquid composition of the present invention is, with respect to the total mass of the composition, preferably 75% to 99.5% by mass, more preferably 85% to 99% by mass, and even more preferably 90% to 99% by mass.

<Polymerization Initiator>

In a case where the organic semiconductor liquid composition of the present invention contains the liquid crystal compound having a polymerizable group, the organic semiconductor liquid composition of the present invention preferably further contains a polymerization initiator.

As the polymerization initiator, a photopolymerization initiator is preferable. In a case where the polymerizable group contained in the liquid crystal compound contained in the organic semiconductor liquid composition is a radically polymerizable group, a photo-radical polymerization initiator is preferable.

The photo-radical polymerization initiator is a compound that can initiate and accelerate the polymerization of a polymerizable compound such as an ethylenically unsaturated group-containing compound by using actinic rays.

The "actinic rays" are not particularly limited as long as they are actinic energy rays being capable of providing energy which can generate an initiation species from the polymerization initiator by the irradiation of the actinic rays, and include a wide variety of rays such as α rays, γ rays, X rays, ultraviolet rays (UV), visible rays, and electron beams. Among these, light including at least ultraviolet rays is preferable.

Examples of the photopolymerization initiator include (a) aromatic ketones, (b) acylphosphine compound, (c) aromatic onium salt compound, (d) organic peroxide, (e) thio compound, (f) hexaarylbiimidazole compound, (g) ketoxime ester compound, (h) borate compound, (i) azinium compound, (j) metallocene compound, (k) active ester compound, (l) compound having a carbon halogen bond, (m) alkylamine compound, and the like. As the radical polymerization initiator, one kind of the compounds (a) to (m) may be used singly, or the compounds (a) to (m) may be used in combination.

In the present invention, the composition preferably contains (a) aromatic ketones, and more preferably contains an alkylphenone compound, as the polymerization initiator.

Examples of the alkylphenone compound suitably include commercially available products such as IRGACURE 184 (manufactured by BASF Japan), IRGACURE 369 (manufactured by BASF Japan), IRGACURE 379 (manufactured by BASF Japan), IRGACURE 907 (manufactured by BASF Japan), IRGACURE 2959 (manufactured by BASF Japan), and the like.

One kind of the polymerization initiator may be used singly, or two or more kinds thereof may be used in combination.

The content of the polymerization initiator in the organic semiconductor liquid composition of the present invention is not particularly limited, but is, with respect to the total mass of the organic semiconductor liquid composition, preferably 0.001% to 5% by mass, more preferably 0.005% to 1% by mass, and even more preferably 0.01% to 0.5% by mass. In a case where the content of the polymerization initiator is within the above range, it is possible to obtain an organic semiconductor film having excellent curing properties and better mobility.

The content of the polymerization initiator in the organic semiconductor liquid composition of the present invention is, with respect to 100 parts by mass of the content of the liquid crystal compound having a polymerizable group, preferably 0.1 to 30 parts by mass, more preferably 0.5 to 20 parts by mass, and even more preferably 1 to 10 parts by mass. In a case where the content of the polymerization initiator is within the above range, it is possible to obtain an organic semiconductor film having excellent curing properties and better mobility.

<Other Components>

The organic semiconductor liquid composition of the present invention may contain other components in addition to the above components.

As other components, known additives and the like can be used.

In the organic semiconductor liquid composition of the present invention, the content of components other than the organic semiconductor, the liquid crystal compound, the organic insulating polymer, and the polymerization initiator is preferably equal to or less than 10% by mass, more preferably equal to or less than 5% by mass, even more preferably equal to or less than 1% by mass, and particularly preferably equal to or less than 0.1% by mass. In a case where the content of other components is within the above range, film formability becomes excellent, and the mobility and heat stability of the obtained organic semiconductor are further improved.

The method for manufacturing an organic semiconductor liquid composition of the present invention is not particularly limited, and known methods can be adopted. For example, by simultaneously or sequentially adding a predetermined amount of organic semiconductor, liquid crystal compound, and organic insulating polymer to a solvent and appropriately stirring the solution, a desired composition can be obtained.

The viscosity of the organic semiconductor liquid composition of the present invention is not particularly limited. In view of further improving coating properties, the viscosity of the composition at 25° C. is preferably 1 to 100 mPa·s, more preferably 2 to 50 mPa·s, even more preferably 5 to 40 mPa·s, and particularly preferably 10 to 30 mPa·s.

The viscosity is preferably measured by the method based on JIS Z8803.

(Organic Semiconductor Film and Organic Semiconductor Element)

The organic semiconductor film of the present invention and the organic semiconductor element of the present invention are manufactured using the organic semiconductor liquid composition of the present invention.

The organic semiconductor element of the present invention is preferably prepared by the method for preparing an organic semiconductor element of the present invention that will be described later.

The organic semiconductor film of the present invention is preferably prepared by the method for preparing an organic semiconductor film of the present invention that will be described later.

The film thickness of the organic semiconductor film is not particularly limited. However, from the viewpoint of the mobility and film uniformity of the obtained organic semiconductor, the film thickness of the organic semiconductor film is preferably 10 to 500 nm, and more preferably 30 to 200 nm.

The organic semiconductor film manufactured using the organic semiconductor liquid composition of the present invention can be suitably used in an organic semiconductor element, and can be particularly suitably used in an organic transistor (organic thin film transistor (organic TFT)).

The organic semiconductor element is not particularly limited. However, the organic semiconductor element is preferably a semiconductor element having a plurality of terminals, more preferably an organic semiconductor element having 2 to 5 terminals, and even more preferably an organic semiconductor element having 2 or 3 terminals.

Furthermore, the organic semiconductor element is preferably an element which does not use a photoelectric function. In a case where the organic semiconductor element actively uses a photoelectric function, the organic substance is likely to deteriorate due to light.

Examples of a 2-terminal element include a rectifier diode, a constant voltage diode, a PIN diode, a Schottky barrier diode, a surge protection diode, a diac, a varistor, a tunnel diode, and the like.

Examples of a 3-terminal element include a bipolar transistor, a Darlington transistor, a field effect transistor, insulated gate bipolar transistor, a uni-junction transistor, a static induction transistor, a gate turn thyristor, a triac, a static induction thyristor, and the like.

Among these, a rectifier diode and transistors are preferable, and a field-effect transistor is more preferable.

Examples of the field-effect transistor preferably include an organic thin film transistor.

An aspect of the organic thin film transistor of the present invention will be described with reference to a drawing.

FIG. 1 is a schematic cross-sectional view of an aspect of the organic semiconductor element (organic thin film transistor (TFT)) of the present invention.

In FIG. 1, an organic thin film transistor 100 includes a substrate 10, a gate electrode 20 disposed on the substrate 10, a gate insulating film 30 covering the gate electrode 20, a source electrode 40 and a drain electrode 42 which contact a surface of the gate insulating film 30 that is on the side opposite to the gate electrode 20 side, an organic semiconductor film 50 covering a surface of the gate insulating film 30 between the source electrode 40 and the drain electrode 42, and a sealing layer 60 covering each member. The organic thin film transistor 100 is a bottom gate-bottom contact type organic thin film transistor.

In FIG. 1, the organic semiconductor film 50 corresponds to a film formed of the organic semiconductor liquid composition of the present invention.

Hereinafter, the substrate, the gate electrode, the gate insulating film, the source electrode, the drain electrode, the organic semiconductor film, the sealing layer, and methods for forming each of these will be specifically described.

<Substrate>

The substrate plays a role of supporting the gate electrode, the source electrode, the drain electrode, and the like which will be described later.

The type of the substrate is not particularly limited, and examples thereof include a plastic substrate, a glass substrate, a ceramic substrate, and the like. Among these, from the viewpoint of applicability to each device and costs, a glass substrate or a plastic substrate is preferable.

Examples of materials of the plastic substrate include a thermosetting resin (for example, an epoxy resin, a phenol resin, a polyimide resin, or a polyester resin (for example, polyethylene terephthalate (PET) or polyethylene naphthalate (PEN)) and a thermoplastic resin (for example, a phenoxy resin, a polyethersulfone, polysulfone, or polyphenylene sulfone).

Examples of materials of the ceramic substrate include alumina, aluminum nitride, zirconia, silicon, silicon nitride, silicon carbide, and the like.

Examples of materials of the glass substrate include soda lime glass, potash glass, borosilicate glass, quartz glass, aluminosilicate glass, lead glass, and the like.

<Gate Electrode, Source Electrode, and Drain Electrode>

Examples of materials of the gate electrode, the source electrode, and the drain electrode include a metal such as gold (Au), silver, aluminum ($A^1$), copper, chromium, nickel, cobalt, titanium, platinum, tantalum, magnesium, calcium, barium, or sodium; a conductive oxide such as $InO_2$, $SnO_2$, or indium tin oxide (ITO); a conductive polymer such as polyaniline, polypyrrole, polythiophene, polyacetylene, or polydiacetylene; a semiconductor such as silicon, germanium, or gallium arsenide; a carbon material such as fullerene, carbon nanotubes, or graphite; and the like. Among these, a metal is preferable, and silver and aluminum are more preferable.

The thickness of each of the gate electrode, the source electrode, and the drain electrode is not particularly limited, but is preferably 20 to 200 nm.

The method for forming the gate electrode, the source electrode, and the drain electrode is not particularly limited, but examples thereof include a method of vacuum vapor-depositing or sputtering an electrode material onto a substrate, a method of coating a substrate with a composition for forming an electrode, a method of printing a composition for forming an electrode onto a substrate, and the like. In a case where the electrode is patterned, examples of the patterning method include a photolithography method; a printing method such as ink jet printing, screen printing, offset printing, or relief printing; a mask vapor deposition method; and the like.

<Gate Insulating Film>

Examples of materials of the gate insulating film include a polymer such as polymethyl methacrylate, polystyrene, polyvinylphenol, polyimide, polycarbonate, polyester, polyvinylalcohol, polyvinyl acetate, polyurethane, polysulfone, polybenzoxazole, polysilsesquioxane, an epoxy resin, or a phenol resin; an oxide such as silicon dioxide, aluminum oxide, or titanium oxide; a nitride such as silicon nitride; and the like. Among these materials, in view of the compatibility with the organic semiconductor film, a polymer is preferable.

In a case where a polymer is used as the material of the gate insulating film, it is preferable to use a cross-linking agent (for example, melamine) in combination. If the cross-linking agent is used in combination, the polymer is cross-linked, and hence the durability of the formed gate insulating film is improved.

The film thickness of the gate insulating film is not particularly limited, but is preferably 100 to 1,000 nm.

The method for forming the gate insulating film is not particularly limited, but examples thereof include a method of coating a substrate, on which the gate electrode is formed, with a composition for forming a gate insulating film, a method of vapor-depositing or sputtering the material of the gate insulating film onto a substrate on which the gate electrode is formed, and the like. A method for coating the aforementioned substrate with the composition for forming a gate insulating film is not particularly limited, and it is possible to use a known method (a bar coating method, a spin coating method, a knife coating method, or a doctor blade method).

In a case where the gate insulating film is formed by coating the substrate with the composition for forming a gate insulating film, for the purpose of removing the solvent, causing cross-linking, or the like, the composition may be heated (baked) after coating.

<Organic Semiconductor Film>

The organic semiconductor film of the present invention is a film formed of the organic semiconductor liquid composition of the present invention.

The method for forming the organic semiconductor film is not particularly limited. By applying the aforementioned composition onto the source electrode, the drain electrode, and the gate insulating film and, if necessary, performing a drying treatment, a desired organic semiconductor film can be formed.

<Sealing Layer>

From the viewpoint of durability, the organic thin film transistor of the present invention preferably includes a sealing layer as an outermost layer. In the sealing layer, a known sealant can be used.

The thickness of the sealing layer is not particularly limited, but is preferably 0.2 to 10 μm.

The method for forming the sealing layer is not particularly limited, but examples thereof include a method of coating a substrate, on which the gate electrode, the gate insulating film, the source electrode, the drain electrode, and the organic semiconductor film are formed, with a composition for forming a sealing layer, and the like. Specific examples of the method of coating the substrate with the composition for forming a sealing layer are the same as the examples of the method of coating the substrate with the composition for forming a gate insulating film. In a case where the organic semiconductor film is formed by coating the substrate with the composition for forming a sealing layer, for the purpose of removing the solvent, causing cross-linking, or the like, the composition may be heated (baked) after coating.

Figure 2:
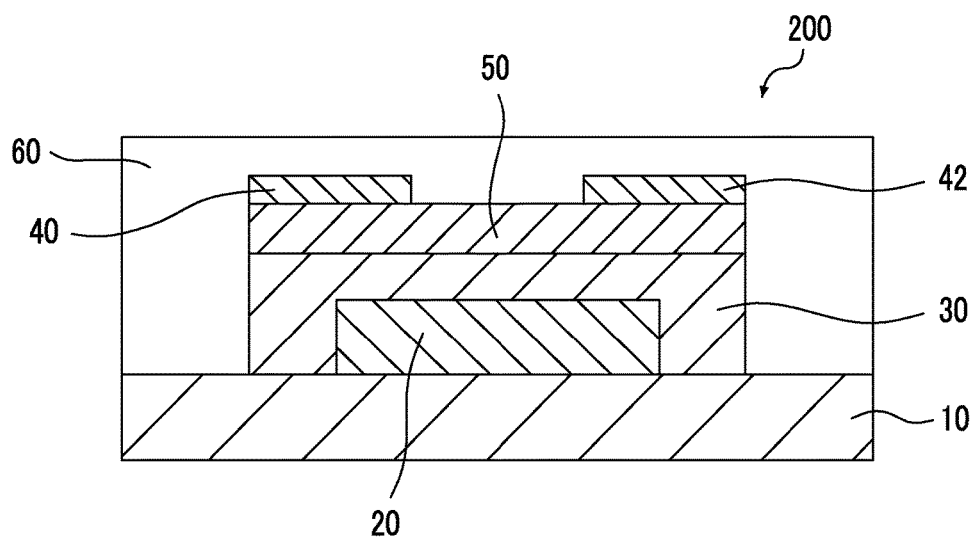
FIG. 2 is a schematic cross-sectional view of another aspect of the organic semiconductor element of the present invention.

FIG. 2 is a schematic cross-sectional view of another aspect of the organic semiconductor element (organic thin film transistor) of the present invention.

In FIG. 2, an organic thin film transistor 200 includes the substrate 10, the gate electrode 20 disposed on the substrate 10, the gate insulating film 30 covering the gate electrode 20, the organic semiconductor film 50 disposed on the gate insulating film 30, the source electrode 40 and the drain electrode 42 disposed on the organic semiconductor film 50, and the sealing layer 60 covering each member. Herein, the source electrode 40 and the drain electrode 42 or the organic semiconductor film 50 can be formed using the aforementioned organic semiconductor liquid composition of the present invention. The organic thin film transistor 200 is a bottom gate-top contact type organic thin film transistor.

The substrate, the gate electrode, the gate insulating film, the source electrode, the drain electrode, the organic semiconductor film, and the sealing layer are as described above.

In FIGS. 1 and 2, the aspects of the bottom gate-bottom contact type organic thin film transistor and the bottom gate-top contact type organic thin film transistor were specifically described. However, the organic semiconductor liquid composition of the present invention can also be applied to a top gate-bottom contact type organic thin film transistor and a top gate-top contact type organic thin film transistor.

Particularly, the organic semiconductor liquid composition of the present invention can be suitably used for a bottom contact-type organic thin film transistor.

The aforementioned organic thin film transistor can be suitably used in electronic paper, a display device, and the like.

(Method for Preparing Organic Semiconductor Element)

The method for preparing an organic semiconductor element of the present invention is not particularly limited as long as the organic semiconductor liquid composition of the present invention is used in the method. However, it is preferable that the method includes a film forming step of forming a film through coating by using the organic semiconductor liquid composition of the present invention, a melting step of melting the film by heating, and a phase separation step of causing phase separation by cooling the melted film so as to form a laminated structure in which an organic insulating polymer layer, an organic semiconductor layer, and a liquid crystal compound layer are laminated in this order.

Figure 3:
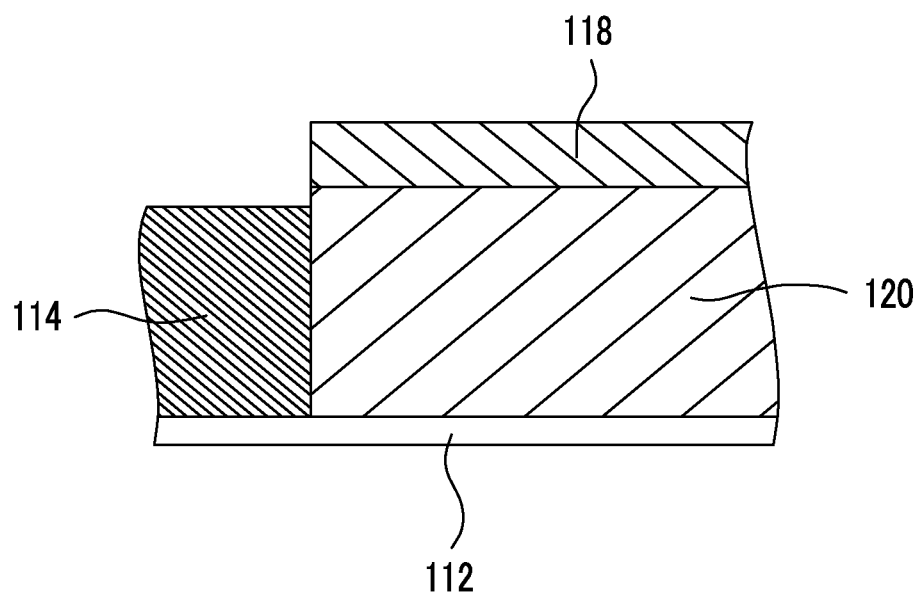
FIG. 3 is a schematic cross-sectional view at the time of forming a bottom contact-type organic thin film transistor by using an organic semiconductor liquid composition of the related art.

FIG. 3 is a schematic cross-sectional view at the time of forming a bottom contact-type organic thin film transistor by using an organic semiconductor liquid composition of the related art.

In a case where the organic semiconductor liquid composition of the related art containing an organic semiconductor and a liquid crystal compound is used, when an organic semiconductor film is formed by coating an insulating layer 110 with the organic semiconductor liquid composition, a liquid crystal layer 120 is formed on the side contacting an insulating film 112, that is, in the lower portion, and an organic semiconductor layer 118 is formed in the upper portion of the liquid crystal layer 120. Particularly, in a case where a bottom contact-type organic thin film transistor is formed, as shown in FIG. 3, the organic semiconductor layer 118 does not contact an electrode 114 forming a source electrode or a drain electrode in many cases.

Figure 4:
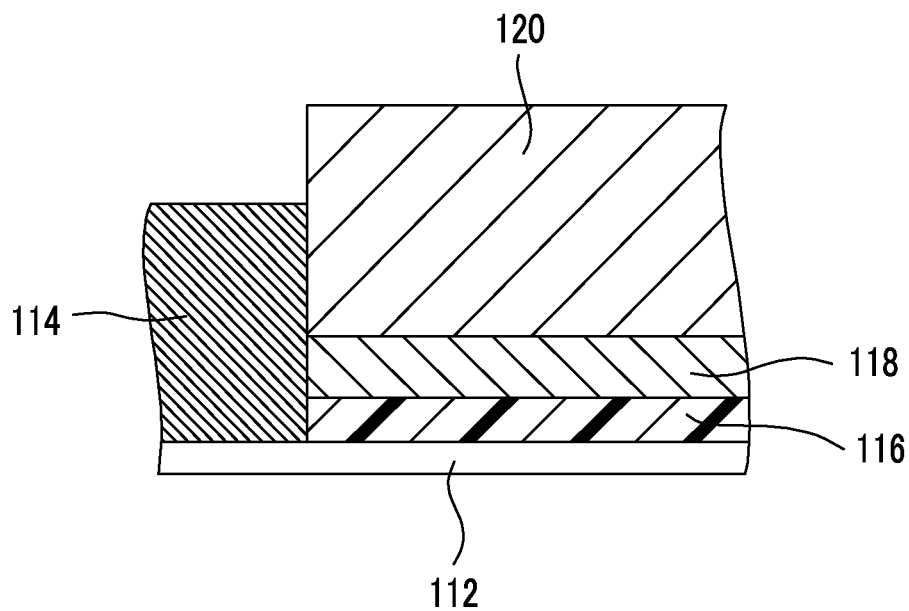
FIG. 4 is a schematic cross-sectional view at the time of forming a bottom contact-type organic thin film transistor by using an organic semiconductor liquid composition of the present invention.

FIG. 4 is a schematic cross-sectional view at the time of forming a bottom contact-type organic thin film transistor by using the organic semiconductor liquid composition of the present invention.

In a case where the organic semiconductor element is prepared by the method for preparing an organic semiconductor element of the present invention that includes the film forming step, the melting step, and the phase separation step described above, an organic insulating polymer layer 116 is formed on the side contacting the insulating film 112, that is, in the lower portion, the organic semiconductor layer 118 is formed in the upper portion of the organic insulating polymer layer 116, and the liquid crystal layer 120 is formed in the upper portion of the organic semiconductor layer 118. Particularly, in a case where a bottom contact-type organic thin film transistor is formed, as shown in FIG. 4, the organic semiconductor layer 118 does not contact the electrode 114 forming a source electrode or a drain electrode in many cases.

The laminated structure formed of the composition of the present invention is greatly different from the laminated structure formed of the organic semiconductor liquid composition of the related art, particularly in the respect that the liquid crystal layer in the laminated structure formed of the composition of the present invention is positioned on the organic semiconductor layer while the liquid crystal layer in the laminated structure formed of the composition of the related art is positioned under the organic semiconductor layer.

<Film Forming Step>

The method for preparing an organic semiconductor element of the present invention preferably includes the film forming step of forming a film through coating by using the organic semiconductor liquid composition of the present invention.

The method for forming the film through coating by using the organic semiconductor liquid composition is not particularly limited, and known methods can be adopted. For example, it is possible to use a method of manufacturing an organic semiconductor film by coating a predetermined base material with the organic semiconductor liquid composition and performing a drying treatment for drying a solvent if necessary.

In a case where the organic semiconductor liquid composition contains a solvent, the solvent may be completely removed at the time of the melting step, or a portion of the solvent may remain in the film.

The method for coating the base material with the organic semiconductor liquid composition is not particularly limited, and known methods can be adopted. Examples of the method include an ink jet method, a flexographic printing method, a gravure printing method, a screen printing method, a bar coating method, a spin coating method, a knife coating method, a doctor blade method, and the like. Among these, a spin coating method is preferable.

For the aforementioned drying treatment, optimal conditions are appropriately selected according to the type of each component or solvent used. In view of further improving mobility and film uniformity of the obtained organic semiconductor and improving productivity, the heating temperature is preferably 30° C. to 100° C. and more preferably 40° C. to 80° C., and the heating time is preferably 1 to 300 minutes and more preferably 30 to 180 minutes.

<Melting Step>

The method for preparing an organic semiconductor element of the present invention preferably includes the melting step of melting the film formed by the film forming step by heating.

By performing the melting step, the phase separation in the phase separation step which will be described later sufficiently proceeds, each layer is suitably formed, and hence the mobility of the obtained organic semiconductor layer is further improved.

Regarding the heating temperature in the melting step, optimal conditions are appropriately selected according to the type of each component used. In view of further improving the mobility and film uniformity of the obtained organic semiconductor and in view of improving productivity, the heating temperature is preferably 100° C. to 200° C., more preferably 110° C. to 190° C., and even more preferably 120° C. to 180° C. The heating time is preferably 0.1 to 5 minutes, and more preferably 0.5 to 2 minutes.

<Phase Separation Step>

The method for preparing an organic semiconductor element of the present invention preferably includes the phase separation step of causing phase separation by cooling the melted film so as to form a laminated structure in which the organic insulating polymer layer, the organic semiconductor layer, and the liquid crystal compound layer are laminated in this order.

The temperature (maturing temperature) in the phase separation step may be equal to or lower than the heating temperature of the melting step. The temperature in the phase separation step is preferably 10° C. to 150° C., more preferably 80° C. to 120° C., even more preferably 85° C. to 115° C., particularly preferably 90° C. to 110° C., and most preferably 90° C. to 105° C. In a case where the temperature is within the above range, the mobility of the obtained organic semiconductor layer is further improved.

The temperature in the phase separation step is preferably a temperature at which a crystal of an organic semiconductor can be generated.

The time (maturing time) in the phase separation step is preferably 0.5 to 10 minutes, and more preferably 1 to 5 minutes.

<Polymerization Step>

In a case where the aforementioned liquid crystal compound is a liquid crystal compound having a polymerizable group, the method for preparing an organic semiconductor element of the present invention preferably further includes a polymerization step of polymerizing the liquid crystal compound having a polymerizable group after the phase separation step.

The temperature (polymerization temperature) in the polymerization step is preferably lower than the temperature in the phase separation step. The polymerization temperature is preferably 30° C. to 80° C., and more preferably 40° C. to 70° C.

The polymerization in the polymerization step is preferably caused by the irradiation of actinic rays, and the aforementioned organic semiconductor liquid composition preferably contains a photopolymerization initiator.

After maturing in the phase separation step, by cooling the film down to the polymerization temperature and irradiating the film with actinic rays, the liquid crystal compound layer can be fixed by polymerization.

As an irradiation light source used for the irradiation of actinic rays, it is possible to use a low-pressure mercury lamp, a high-pressure mercury lamp, an ultrahigh-pressure mercury lamp, a chemical lamp, an LED light source, an eximer laser generating device, and the like. Furthermore, it is possible to use actinic rays having a wavelength of equal to or longer than 300 nm and equal to or shorter than 450 nm, such as g line (436 nm), i line (365 nm), or h line (405 nm). If necessary, the irradiation light can be adjusted through a spectral filter such as a long-wavelength cut-off filter, a short-wavelength cut-off filter, or a bandpass filter.

The actinic rays in the polymerization step is preferably light including at least ultraviolet rays.

As the irradiation device, it is possible to use irradiation machines using various methods such as a mirror projection aligner, a stepper, a scanner, proximity, contact, a microlens array, and laser irradiation.

The irradiation amount is preferably 100 to 3,000 mJ/cm², and particularly preferably 100 to 1,000 mJ/cm².

The method for preparing an organic semiconductor element of the present invention may include other steps in addition to the aforementioned steps or the drying treatment.

The method for preparing an organic semiconductor element can include, as other steps, known steps performed in preparing an organic semiconductor element.

(Method for Preparing Organic Semiconductor Film)

The method for preparing an organic semiconductor film of the present invention is not particularly limited as long as the organic semiconductor liquid composition of the present invention is used. It is preferable that the method for preparing an organic semiconductor film includes a film forming step of forming a film through coating by using the organic semiconductor liquid composition of the present invention, a melting step of melting the film by heating, and a phase separation step of causing phase separation by cooling the melted film so as to form a laminated structure in which the organic insulating polymer layer, the organic semiconductor layer, and the liquid crystal compound layer are laminated in this order.

The preferred aspects of the film forming step, the melting step, and the phase separation step in the method for preparing an organic semiconductor film of the present invention are the same as the preferred aspects of the film forming step, the melting step, and the phase separation step in the method for preparing an organic semiconductor element of the present invention.

In the method for preparing an organic semiconductor film of the present invention, a drying treatment may be performed in addition to the aforementioned steps, and the method may include other steps.

The method for preparing an organic semiconductor film can include, as other steps, known steps performed in preparing an organic semiconductor film.

EXAMPLES

Hereinafter, the present invention will be more specifically described based on examples. The materials and the amount thereof used, the proportion of the materials, the content and procedure of treatments, and the like described in the following examples can be appropriately changed within a scope that does not depart from the gist of the present invention. Accordingly, the scope of the present invention is not limited to the following specific examples. Herein, unless otherwise specified, "part" and "%" are based on mass.

<Number-Average Molecular Weight (Mn) and Weight-Average Molecular Weight (Mw) of Polymer>

The number-average molecular weight (Mn) and the weight-average molecular weight (Mw) of a polymer were measured using an ultraviolet detector (wavelength: 254 nm) and tetrahydrofuran as an eluent by dissolving the polymer in tetrahydrofuran, connecting TSK-GEL Super H1000, Super H2000, Super H3000, and Super H4000 in series in a 8020 GPC system manufactured by a Tosoh Corporation. For correcting the molecular weight, a polystyrene standard was used.

The details of the components used in each example and comparative example are as below.

<Organic Semiconductor Compound>
OSC-1 (compound having the following structure)
OSC-2 (compound having the following structure)
OSC-3 (compound having the following structure)

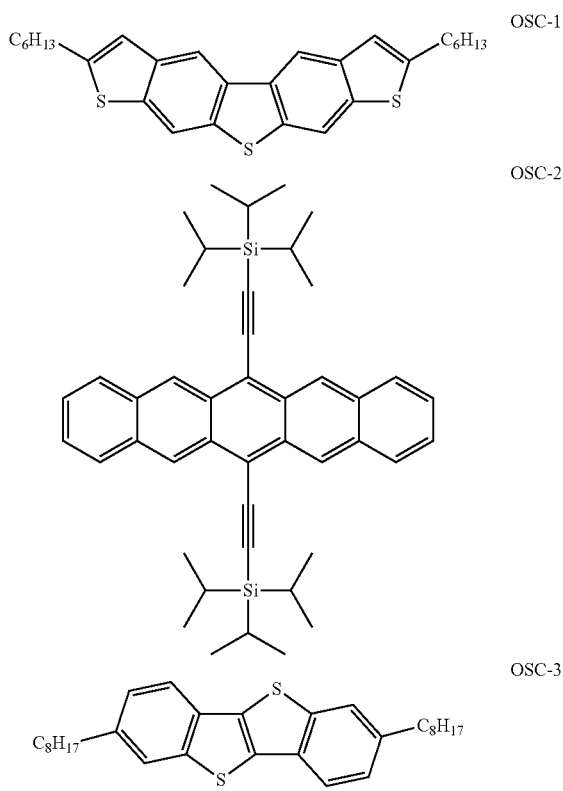

The compound OCS-1 can be synthesized by the method described in Tetrahedron 66 (2010) 8778~8784.

As OCS-2, 6,13-bis(triisopropylsilylethynyl)pentacene (manufactured by TOKYO CHEMICAL INDUSTRY CO., LTD.) was used.

As OSC-3, C8BTBT (manufactured by Nippon Kayaku Co., Ltd.) was used.

<Liquid Crystal Compound>
LCC-A (rod-like liquid crystal compound having the following structure was synthesized by the method described in JP2001-328973A.)
LCC-B (discotic liquid crystal compound having the following structure was synthesized by the method described in JP2009-97002A.)
LCC-C (liquid crystal compound having the following structure was synthesized by the method described in U.S. Pat. No. 4,229,315A.)

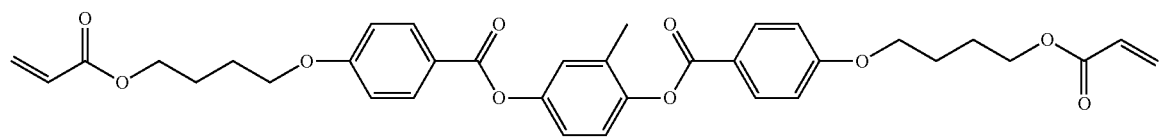

LCC-B

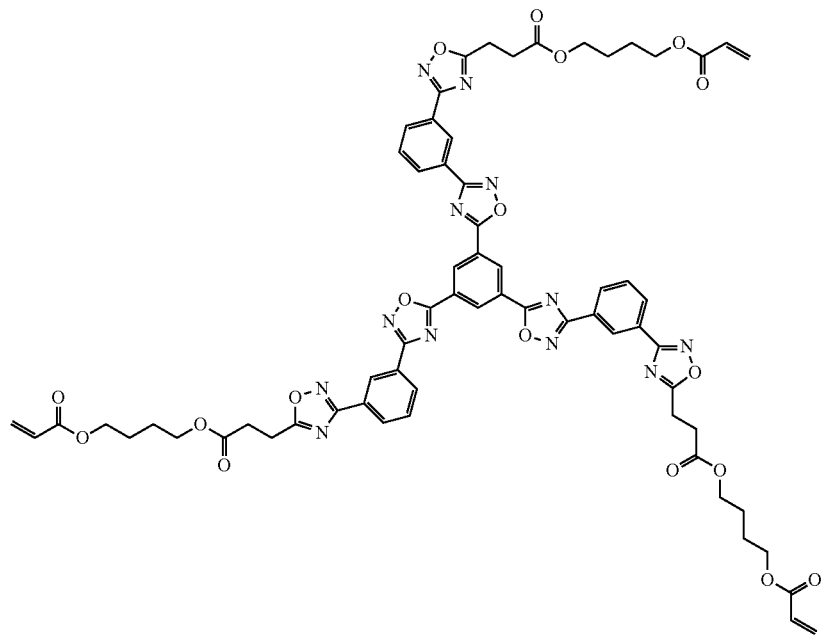

LCC-C

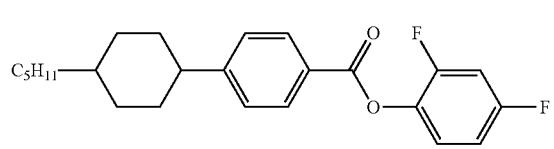

<Polymerization Initiator>
IRGACURE 184 (1-hydroxy-cyclohexyl-phenyl-ketone, manufactured by BASF SE, molecular weight: 204)
<Organic Solvent>
Toluene (manufactured by Wako Pure Chemical Industries, Ltd.)
<Organic Insulating Polymer>
SP-1: polyvinyl stearate (manufactured by Sigma-Aldrich Co. LLC., weight-average molecular weight: 90,000)
SP-2: polyvinyl acetate (manufactured by Sigma-Aldrich Co. LLC., weight-average molecular weight: 100,000)
SP-3: copolymer obtained by copolymerizing vinyl octanoate and vinyl stearate (all manufactured by Wako Pure Chemical Industries, Ltd.), copolymerization ratio=45 mol % of vinyl octanoate portion:55 mol % of vinyl stearate portion, weight-average molecular weight of 82,100
SP-4: polyvinyl butyral (MOWITAL B30HH manufactured by KURARAY CO., LTD., content of hydroxyl group: 11% to 15% by mass)

(SP-1)
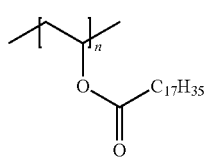

-continued (SP-2)
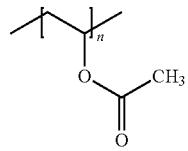

(SP-3)
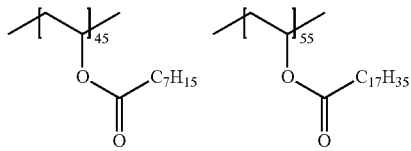

(SP-4)
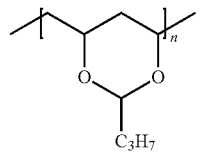

<Preparation of Coating Solution Containing Organic Semiconductor>

The components described in the following Table 1 were mixed together at a ratio described in Table 1, thereby preparing coating solutions T1 to T36 containing an organic semiconductor.

TABLE 1

| Coating solution | Organic semiconductor Type | Concentration of solid content | Liquid crystal compound Type | Concentration of solid content | Organic insulating polymer Type | Concentration of solid content | Polymerization initiator Type | Concentration of solid content | Organic solvent |
|---|---|---|---|---|---|---|---|---|---|
| T1 | OSC-1 | 0.15% by mass | LCC-A | 2.5% by mass | SP-1 | 0.1% by mass | IRGACURE 184 | 0.075% by mass | Toluene |
| T2 | OSC-2 | | | | | | | | |
| T3 | OSC-3 | | | | | | | | |
| T4 | OSC-1 | | LCC-B | | | | | | |
| T5 | OSC-2 | | | | | | | | |
| T6 | OSC-3 | | | | | | | | |
| T7 | OSC-1 | | LCC-A | | SP-2 | | | | |
| T8 | OSC-2 | | | | | | | | |
| T9 | OSC-3 | | | | | | | | |
| T10 | OSC-1 | | LCC-B | | | | | | |
| T11 | OSC-2 | | | | | | | | |
| T12 | OSC-3 | | | | | | | | |
| T13 | OSC-1 | | LCC-A | | SP-3 | | | | |
| T14 | OSC-2 | | | | | | | | |
| T15 | OSC-3 | | | | | | | | |
| T16 | OSC-1 | | LCC-B | | | | | | |
| T17 | OSC-2 | | | | | | | | |
| T18 | OSC-3 | | | | | | | | |
| T19 | OSC-1 | | LCC-A | | SP-4 | | | | |
| T20 | OSC-2 | | | | | | | | |
| T21 | OSC-3 | | | | | | | | |
| T22 | OSC-1 | | LCC-B | | | | | | |
| T23 | OSC-2 | | | | | | | | |
| T24 | OSC-3 | | | | | | | | |
| T25 | OSC-1 | 0.3% by mass | LCC-A | 5.0% by mass | SP-1 | | | 0.15% by mass | |
| T26 | | | | | | 0.3% by mass | | | |
| T27 | | 0.15% by mass | | | | 0.1% by mass | | | |
| T28 | | | | | | 0.3% by mass | | | |
| T29 | | 0.25% by mass | LCC-C | 2.0% by mass | | 0.1% by mass | N/A | N/A | |
| T30 | OSC-1 | 0.15% by mass | LCC-A | 2.5% by mass | N/A | N/A | IRGACURE 184 | 0.075% by mass | |
| T31 | OSC-2 | | | | | | | | |
| T32 | OSC-3 | | | | | | | | |
| T33 | OSC-1 | | LCC-B | | | | | | |
| T34 | OSC-2 | | | | | | | | |
| T35 | OSC-3 | | | | | | | | |
| T36 | OSC-1 | 0.25% by mass | LCC-C | 2.0% by mass | | | N/A | N/A | |

<Preparation of Substrate>

A silicon substrate (thickness: 0.7 mm) coated with thermally oxidized silicon having a thickness of 350 nm was spin-coated (2,000 rpm/20 sec.) with a 2% by mass polyimide (SE-130) solution (N-methylpyrrolidone) manufactured by NISSAN CHEMICAL INDUSTRIES, LTD., subjected to pre-drying for 5 minutes at 110° C., and then subjected to an imidation treatment by being thermally treated for 60 minutes at 240° C. On the polyimide film, a silver electrode (thickness: 100 nm) was vapor-deposited through a mask, thereby disposing a source electrode and a drain electrode.

<Preparation of Sample for Mobility Evaluation>

By spin-coating (for 2 minutes at 500 rpm) the substrate with the coating solution described in Table 1, a coating film was prepared. Then, the coating film was kept for 1 minute at the thermal treatment temperature described in Table 2 and then cooled down to a maturing temperature, and the crystal was matured for 2 minutes. After being cooled down to an ultraviolet (UV) irradiation temperature, the coating film was irradiated with ultraviolet rays having a wavelength of around 365 nm of an ultrahigh-pressure mercury lamp at 540 mJ/cm$^2$ such that the film was polymerized and fixed.

<Measurement of Mobility>

By using a semiconductor parameter analyzer (4156C manufactured by Agilent Technologies) connected to a semi-automatic prober (AX-2000 manufactured by Vector Semi-conductor Co., Ltd.), the carrier mobility of the top gate-top contact type element was evaluated under a normal pressure in nitrogen atmosphere.

Between the source electrode and the drain electrode of each element, a voltage of −80 V was applied, and the gate voltage was varied within a range of 20 V to −100 V In this way, a carrier mobility μ was calculated using the following equation showing a drain current Id.

$$Id = (w/2L)\mu C_i (Vg - Vth)^2$$

In the equation, L represents a gate length, W represents a gate width, Ci represents a capacity of the insulating layer per unit area, Vg represents a gate voltage, and Vth represents a threshold voltage.

The evaluation standard will be shown below. The sample evaluated to be 1 or 2 is unproblematic for practical use, and it is preferable that the sample is evaluated to be 1.

1: greater than 0.5 cm$^2$/Vs
2: 0.1 cm$^2$/Vs to 0.5 cm$^2$/Vs
3: less than 0.1 cm$^2$/Vs Example 1

According to the method described in the above Preparation of sample for mobility evaluation, the substrate was spin-coated with a coating solution T1, and a sample S1 was prepared at a heating temperature of 17° C., a maturing temperature of 100° C., and a UV irradiation temperature of 60° C. The mobility of the bottom gate-bottom contact type element of the sample S1 was 0.80 cm²/Vs.

Examples 2 to 29

The mobility was evaluated in the same manner as in Example 1, except that coating solutions T2 to T29 were used, and the heating temperature, the maturing temperature, and the UV irradiation temperature were changed as shown in Table 2. The evaluation results are described in Table 2.

Comparative Example 1

According to the method described in the above Preparation of sample for mobility evaluation, the substrate was spin-coated with a coating solution T30, and a sample S25 was prepared at a heating temperature of 170° C., a maturing temperature of 100° C., and a UV irradiation temperature of 60° C. The mobility of the bottom gate-bottom contact type element of the sample S30 was not measured.

Comparative Examples 2 to 7

The mobility was evaluated in the same manner as in Comparative Example 1, except that T31 to T36 were used as coating solutions, and the heating temperature, the maturing temperature, and the UV irradiation temperature were changed as described in Table 2. The evaluation results are described in Table 2.

TABLE 2

| | Sample | Coating solution | Heating temperature | Maturing temperature | UV irradiation temperature | Mobility |
|---|---|---|---|---|---|---|
| Example 1 | S1 | T1 | 170° C. | 100° C. | 60° C. | 1 |
| Example 2 | S2 | T2 | 175° C. | 100° C. | | 1 |
| Example 3 | S3 | T3 | 120° C. | 90° C. | | 1 |
| Example 4 | S4 | T4 | 180° C. | 110° C. | | 2 |
| Example 5 | S5 | T5 | 180° C. | 110° C. | | 2 |
| Example 6 | S6 | T6 | 140° C. | 90° C. | | 2 |
| Example 7 | S7 | T7 | 170° C. | 100° C. | | 1 |
| Example 8 | S8 | T8 | 175° C. | 100° C. | | 1 |
| Example 9 | S9 | T9 | 120° C. | 90° C. | | 1 |
| Example 10 | S10 | T10 | 180° C. | 110° C. | | 2 |
| Example 11 | S11 | T11 | 180° C. | 110° C. | | 2 |
| Example 12 | S12 | T12 | 140° C. | 90° C. | | 2 |
| Example 13 | S13 | T13 | 170° C. | 100° C. | | 1 |
| Example 14 | S14 | T14 | 175° C. | 100° C. | | 1 |
| Example 15 | S15 | T15 | 120° C. | 90° C. | | 1 |
| Example 16 | S16 | T16 | 180° C. | 110° C. | | 2 |
| Example 17 | S17 | T17 | 180° C. | 110° C. | | 2 |
| Example 18 | S18 | T18 | 140° C. | 90° C. | | 2 |
| Example 19 | S19 | T19 | 170° C. | 100° C. | | 1 |
| Example 20 | S20 | T20 | 175° C. | 100° C. | | 1 |
| Example 21 | S21 | T21 | 120° C. | 90° C. | | 1 |
| Example 22 | S22 | T22 | 180° C. | 110° C. | | 2 |
| Example 23 | S23 | T23 | 180° C. | 110° C. | | 2 |
| Example 24 | S24 | T24 | 140° C. | 90° C. | | 2 |
| Example 25 | S25 | T25 | 170° C. | 100° C. | | 1 |
| Example 26 | S26 | T26 | 170° C. | 100° C. | | 1 |
| Example 27 | S27 | T27 | 150° C. | 90° C. | | 1 |
| Example 28 | S28 | T28 | 150° C. | 90° C. | | 1 |
| Example 29 | S29 | T29 | 130° C. | 90° C. | | 1 |
| Comparative Example 1 | S30 | T30 | 170° C. | 100° C. | | Not measured |
| Comparative Example 2 | S31 | T31 | 175° C. | 100° C. | | |
| Comparative Example 3 | S32 | T32 | 120° C. | 90° C. | | |
| Comparative Example 4 | S33 | T33 | 180° C. | 110° C. | | |
| Comparative Example 5 | S34 | T34 | 180° C. | 110° C. | | |
| Comparative Example 6 | S35 | T35 | 140° C. | 90° C. | | |
| Comparative Example 7 | S36 | T36 | 130° C. | 90° C. | | |

EXPLANATION OF REFERENCES

10: substrate
20: gate electrode
30: gate insulating film
40: source electrode
42: drain electrode
50: organic semiconductor film
51: metal mask
52: mask portion
53, 54: opening portion
60: sealing layer
100, 200: organic thin film transistor
112: insulating layer 114: electrode (source electrode or drain electrode)
116: organic insulating polymer layer
118: organic semiconductor layer
120: liquid crystal compound layer

What is claimed is:

1. An organic semiconductor liquid composition comprising:
   an organic semiconductor;
   a liquid crystal compound; and
   an organic insulating polymer.

2. The organic semiconductor liquid composition according to claim 1,
   wherein the organic insulating polymer includes a resin having a constitutional unit represented by the following Formula 1a and/or a constitutional unit represented by the following Formula 1b,

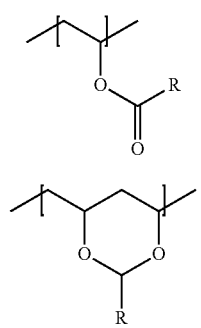

(1a)

(1b)

in the formulae, R's each independently represent a linear or branched alkyl group having 1 to 20 carbon atoms.

3. The organic semiconductor liquid composition according to claim 1,
   wherein the organic insulating polymer is polyvinyl carboxylate or polyvinyl acetal.

4. The organic semiconductor liquid composition according to claim 1,
   wherein the organic insulating polymer is polyvinyl carboxylate or polyvinyl butyral.

5. The organic semiconductor liquid composition according to claim 1,
   wherein the liquid crystal compound includes a liquid crystal compound having a polymerizable group.

6. The organic semiconductor liquid composition according to claim 5,
   wherein the liquid crystal compound includes a liquid crystal compound having an ethylenically unsaturated group.

7. The organic semiconductor liquid composition according to claim 5, further comprising:
   a polymerization initiator.

8. A method for preparing an organic semiconductor element, comprising:
   a film forming step of forming a film through coating by using an organic semiconductor liquid composition comprising an organic semiconductor, a liquid crystal compound, and an organic insulating polymer;
   a melting step of melting the film by heating; and
   a phase separation step of causing phase separation by cooling the melted film so as to form a laminated structure in which an organic insulating polymer layer, an organic semiconductor layer, and a liquid crystal compound layer are laminated in this order.

9. The method for preparing an organic semiconductor element according to claim 8, further comprising:
   a polymerization step of polymerizing a liquid crystal compound having a polymerizable group after the phase separation step,
   wherein the liquid crystal compound includes a liquid crystal compound having a polymerizable group.

10. The method for preparing an organic semiconductor element according to claim 8,
    wherein the obtained organic semiconductor element is an organic thin film transistor.

11. The method for preparing an organic semiconductor element according to claim 8,
    wherein the obtained organic semiconductor element is a bottom contact-type organic thin film transistor.

12. The method for preparing an organic semiconductor element according to claim 8,
    wherein the organic insulating polymer includes a resin having a constitutional unit represented by the following Formula 1a and/or a constitutional unit represented by the following Formula 1b,

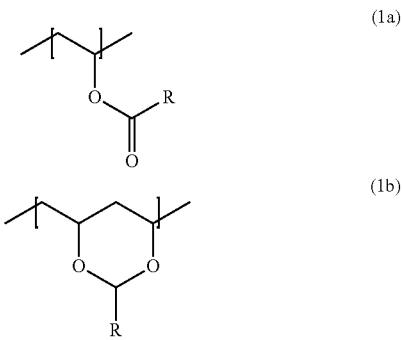

(1a)

(1b)

in the formulae, R's each independently represent a linear or branched alkyl group having 1 to 20 carbon atoms.

13. The method for preparing an organic semiconductor element according to claim 8,
    wherein the organic insulating polymer is polyvinyl carboxylate or polyvinyl acetal.

14. The method for preparing an organic semiconductor element according to claim 8,
    wherein the organic insulating polymer is polyvinyl carboxylate or polyvinyl butyral.

15. The method for preparing an organic semiconductor element according to claim 8,
    wherein the liquid crystal compound includes a liquid crystal compound having a polymerizable group.

16. The method for preparing an organic semiconductor element according to claim 8,
    wherein the liquid crystal compound includes a liquid crystal compound having an ethylenically unsaturated group.

17. The method for preparing an organic semiconductor element according to claim 8,
    wherein the organic semiconductor liquid composition further comprising a polymerization initiator.

* * * * *